US012655443B2

(12) United States Patent
Chen et al.

(10) Patent No.: US 12,655,443 B2
(45) Date of Patent: *Jun. 16, 2026

(54) ENHANCED EXPRESSION SYSTEM AND METHODS OF USE THEREOF

(71) Applicant: WuXi Biologics Ireland Limited, Dundalk (IE)

(72) Inventors: Ji Chen, Shanghai (CN); Yu Zhang, Shanghai (CN); Jung-hao Wang, Shanghai (CN); Yarong Li, Shanghai (CN); Bin Zhao, Shanghai (CN); Dujuan Lian, Shanghai (CN); Yuchen Zhang, Shanghai (CN); Cui Huang, Shanghai (CN); Zheng Zhang, Shanghai (CN); Jiexing Cai, Shanghai (CN)

(73) Assignee: WuXi Biologics Ireland Limited, Dundalk (IE)

( * ) Notice: Subject to any disclaimer, the term of this patent is extended or adjusted under 35 U.S.C. 154(b) by 894 days.

This patent is subject to a terminal disclaimer.

(21) Appl. No.: 17/801,038

(22) PCT Filed: Feb. 18, 2021

(86) PCT No.: PCT/CN2021/076719
§ 371 (c)(1),
(2) Date: Aug. 19, 2022

(87) PCT Pub. No.: WO2021/164704
PCT Pub. Date: Aug. 26, 2021

(65) Prior Publication Data
US 2023/0203530 A1 Jun. 29, 2023

(30) Foreign Application Priority Data

Feb. 19, 2020 (CN) .......................... 202010102211.1
Mar. 26, 2020 (WO) ................ PCT/CN2020/081464

(51) Int. Cl.
| | |
|---|---|
| *C12N 15/85* | (2006.01) |
| *C07K 14/705* | (2006.01) |
| *C07K 16/24* | (2006.01) |
| *C12N 15/62* | (2006.01) |

(52) U.S. Cl.
CPC ........ *C12N 15/85* (2013.01); *C07K 14/70532* (2013.01); *C07K 16/241* (2013.01); *C12N 15/62* (2013.01); *C07K 2319/30* (2013.01); *C12N 2800/90* (2013.01)

(58) Field of Classification Search
CPC .... C12N 15/85; C12N 15/62; C12N 2800/90; C12N 15/1051; C12N 15/63; C07K 2319/30; C07K 16/00
See application file for complete search history.

(56) References Cited

U.S. PATENT DOCUMENTS

| | | | |
|---|---|---|---|
| 6,218,185 | B1 | 4/2001 | Shirk et al. |
| 6,518,064 | B1 | 2/2003 | Miller et al. |
| 6,551,825 | B1 | 4/2003 | Shirk et al. |
| 6,773,914 | B1 | 8/2004 | Handler |
| 6,962,810 | B2 | 11/2005 | Fraser et al. |
| 7,005,296 | B1 | 2/2006 | Handler |
| 7,105,343 | B1 | 9/2006 | Fraser et al. |
| 7,129,083 | B1 | 10/2006 | Handler |
| 7,132,586 | B2 | 11/2006 | Craig et al. |
| 8,524,979 | B2 | 9/2013 | Charng |
| 8,546,135 | B2 | 10/2013 | Wu et al. |
| 8,592,211 | B2 | 11/2013 | Brivanlou et al. |
| 9,428,767 | B2 | 8/2016 | Minshull et al. |
| 9,534,234 | B2 | 1/2017 | Minshull et al. |
| 9,574,209 | B2 | 2/2017 | Minshull et al. |
| 9,580,697 | B2 | 2/2017 | Minshull et al. |
| 9,670,503 | B2 | 6/2017 | Craig |
| 9,783,790 | B2 | 10/2017 | Craig |
| 9,840,718 | B2 | 12/2017 | Solodushko et al. |
| 10,041,077 | B2 | 8/2018 | Minshull |
| 10,087,463 | B2 | 10/2018 | Fraser et al. |
| 10,174,309 | B2 | 1/2019 | Grawunder |
| 10,233,454 | B2 | 3/2019 | Minshull et al. |
| 10,344,285 | B2 | 7/2019 | Minshull et al. |
| 10,415,022 | B2 | 9/2019 | Craig |
| 10,435,696 | B2 | 10/2019 | Minshull et al. |
| 11,254,952 | B2 * | 2/2022 | Zhang .................... C12N 15/67 |
| 2006/0210977 | A1 | 9/2006 | Kaminski |
| 2007/0204356 | A1 | 8/2007 | Fraser |
| 2009/0042297 | A1 | 2/2009 | George et al. |

(Continued)

FOREIGN PATENT DOCUMENTS

| | | |
|---|---|---|
| CN | 101343638 A | 1/2009 |
| CN | 101297031 B | 6/2013 |

(Continued)

OTHER PUBLICATIONS

Cary, L. C., Goebel, M., Corsaro, B. G., Wang, H. G., Rosen, E., & Fraser, M. J. (1989). Transposon mutagenesis of baculoviruses: analysis of Trichoplusia ni transposon IFP2 insertions within the FP-locus of nuclear polyhedrosis viruses. Virology, 172(1), 156-169 (Year: 1989).*

(Continued)

*Primary Examiner* — Arthur S Leonard
*Assistant Examiner* — Erin V Paulus
(74) *Attorney, Agent, or Firm* — Fish & Richardson P.C.

(57) ABSTRACT

This disclosure relates to an efficient protein expression system that utilizes piggyBac transposons and/or regulatory elements.

22 Claims, 31 Drawing Sheets

Specification includes a Sequence Listing.

(56) References Cited

U.S. PATENT DOCUMENTS

| | | | |
|---|---|---|---|
| 2010/0077495 A1* | 3/2010 | Davis | C12N 15/635 |
| | | | 435/325 |
| 2010/0154070 A1 | 6/2010 | Xu et al. | |
| 2010/0221824 A1 | 9/2010 | Fraser et al. | |
| 2010/0311116 A1 | 12/2010 | Wurm et al. | |
| 2013/0209426 A1 | 8/2013 | Bradley et al. | |
| 2015/0218584 A1 | 8/2015 | Payne et al. | |
| 2015/0361451 A1 | 12/2015 | Le Fourn et al. | |
| 2016/0046959 A1 | 2/2016 | Landel et al. | |
| 2017/0101646 A1 | 4/2017 | Minshull et al. | |
| 2018/0258436 A1 | 9/2018 | Minshull et al. | |
| 2018/0265890 A1 | 9/2018 | Qian | |
| 2018/0305715 A1 | 10/2018 | Gray | |
| 2019/0002914 A1 | 1/2019 | Fraser et al. | |
| 2019/0040414 A1 | 2/2019 | Wu | |
| 2019/0055568 A1 | 2/2019 | Pule et al. | |
| 2019/0153433 A1 | 5/2019 | Grawunder | |
| 2019/0169637 A1 | 6/2019 | Hudecek et al. | |
| 2019/0185863 A1 | 6/2019 | Mcgrew et al. | |
| 2019/0185881 A1 | 6/2019 | McGrew et al. | |
| 2019/0224236 A1 | 7/2019 | Riddell et al. | |
| 2021/0324407 A1* | 10/2021 | Jensen | C12N 15/85 |

FOREIGN PATENT DOCUMENTS

| | | | |
|---|---|---|---|
| CN | 105073995 A | 11/2015 | |
| CN | 105481984 A | 4/2016 | |
| CN | 103834686 B | 5/2016 | |
| CN | 106414748 A | 2/2017 | |
| CN | 106755096 A | 5/2017 | |
| CN | 107312796 A | 11/2017 | |
| CN | 108384811 A | 8/2018 | |
| CN | 105154473 B | 3/2019 | |
| CN | 110177802 A | 8/2019 | |
| CN | 110267980 A | 9/2019 | |
| CN | 110462040 A | 11/2019 | |
| CN | 110577605 A | 12/2019 | |
| CN | 106414748 B | 5/2021 | |
| EP | 1896578 A1 | 3/2008 | |
| EP | 1222301 B2 | 5/2008 | |
| EP | 1546322 B1 | 1/2011 | |
| EP | 3129487 A2 | 2/2017 | |
| EP | 3352798 A1 | 8/2018 | |
| EP | 3019618 B1 | 10/2018 | |
| EP | 2951309 B1 | 1/2019 | |
| EP | 3361869 A4 | 4/2019 | |
| EP | 3433366 A4 | 8/2019 | |
| WO | WO 2001/14537 A1 | 3/2001 | |
| WO | WO 2001/29205 A3 | 9/2001 | |
| WO | WO 2001/29204 A3 | 11/2001 | |
| WO | WO 2004/009792 A3 | 5/2004 | |
| WO | WO 2006/122442 A1 | 11/2006 | |
| WO | WO 2007/100821 A3 | 9/2007 | |
| WO | WO 2008/079608 A1 | 7/2008 | |
| WO | WO 2008/098181 A8 | 8/2008 | |
| WO | WO 2010/085699 A3 | 7/2010 | |
| WO | WO 2010/099296 A1 | 9/2010 | |
| WO | WO 2010/099301 A3 | 9/2010 | |
| WO | WO 2012/025725 A1 | 3/2012 | |
| WO | WO 2013/012824 A3 | 1/2013 | |
| WO | WO 2014/013026 A8 | 1/2014 | |
| WO | WO 2014/118619 A3 | 8/2014 | |
| WO | WO 2014/196931 A1 | 12/2014 | |
| WO | WO 2015/006700 A1 | 1/2015 | |
| WO | WO 2015/157579 A3 | 10/2015 | |
| WO | WO 2017/050884 A1 | 3/2017 | |
| WO | WO 2017/054647 A1 | 4/2017 | |
| WO | WO 2017/062668 A3 | 4/2017 | |
| WO | WO 2017/066579 A1 | 4/2017 | |
| WO | WO 2017/132376 A1 | 8/2017 | |
| WO | WO 2017/161553 A1 | 9/2017 | |
| WO | WO 2017/192924 A1 | 11/2017 | |
| WO | WO 2018/189535 A1 | 10/2018 | |
| WO | WO 2019/051424 A9 | 3/2019 | |
| WO | WO 2019/219947 A1 | 11/2019 | |
| WO | WO 2020/034097 A1 | 2/2020 | |
| WO | WO 2020/034986 A1 | 2/2020 | |

OTHER PUBLICATIONS

Chang et al., "Scaffold/matrix attachment regions from CHO cell chromosome enhanced the stable transfection efficiency and the expression of transgene in CHO cells," Biotechnology and Applied Biochemistry, Sep. 2014, 61(5):510-516.

Cary et al., "Transposon mutagenesis of baculoviruses: analysis of Trichoplusia ni transposon IFP2 insertions within the FP-locus of nuclear polyhedrosis viruses," Virology, Sep. 1989, 172(1):156-169.

Deer et al., "High-Level Expression of Proteins in Mammalian Cells Using Transcription Regulatory Sequences from the Chinese Hamster EF-1r, Gene," Biotechnology Progress, Jun. 2004, 20(3):880-889.

Ding et al., "Efficient transposition of the PiggyBac (PB) transposon in mammalian cells and mice," Cell, Aug. 2005, 122(3):473-483.

Ebi.ac.uk [online], "Sequence: JU983868.1 TSA: Cunninghamia lanceolata Unigene 12198_C.lanceolata mRNA sequence," Mar. 2013, retrieved on Sep. 7, 2022, retrieved from URL <https://www.ebi.ac.uk/ena/browser/view/JU983868>, 3 pages.

Ebi.ac.uk [online], "Sequence: EF694965.1 TSA: *Homo sapiens* matrix attachment region 1-68 genomic sequence," Jul. 2008, retrieved on Sep. 7, 2022, retrieved from URL <https://www.ebi.ac.uk/ena/browser/view/EF694965>, 3 pages.

Ebi.ac.uk [online], "Sequence: JI872897.1 TSA: Cricetulus griseus contig16113 mRNA sequence," May 2011, retrieved on Sep. 7, 2022, retrieved from URL <https://www.ebi.ac.uk/ena/browser/view/JI872897>, 3 pages.

Fraser et al. "Assay for movement of Lepidopteran transposon IFP2 in insect cells using a baculovirus genome as a target DNA," Virology, Aug. 1995, 211(2):397-407.

Girod et al., "Genome-wide prediction of matrix attachment regions that increase gene expression in mammalian cells," Nature Methods, Sep. 2007, 4(9):747-753.

International Preliminary Report on Patentability in International Appln. No. PCT/CN2021/076719, mailed on Jul. 5, 2022, 14 pages.

International Search Report and Written Opinion in International Appln. No. PCT/CN2021/076719, mailed on Aug. 27, 2021, 7 pages.

Ivics et al., "Molecular reconstruction of Sleeping Beauty, a Tc1-like transposon from fish, and its transposition in human cells," Cell, Nov. 1997, 91(4):501-510.

Kang et al., "A novel regulatory element (E77) isolated from CHO-K1 genomic DNA enhances stable gene expression in Chinese hamster ovary cells," Biotechnology Journal, May 2016, 11(5):633-41.

Ley et al., "MAR elements and transposons for improved transgene integration and expression," PLoS One, Apr. 2013, 8(4):e62784.

Rajendra et.al., "Generation of stable CHO pools yielding antibody titers of up to 7.6 g/L using the piggyBac transposon system," Cell Culture and Tissue Engineering, 2016, 32(5):1301-1307.

Wilson et al., "PiggyBac transposon-mediated gene transfer in human cells," Molecular Therapy, Jan. 2007, 15(1):139-145.

Woodard and Wilson, "piggyBac-ing models and new therapeutic strategies," Trends in Biotechnology, 2015, 33(9):525-33.

Liu et al., "Construction and evaluation of high expression vectors in mammalian cells with Chinese hamster EF1-α gene," Bull Acad Mil Med Sci, Aug. 2006, 30(4):301-305 (with English Abstract).

Rad et al., "PiggyBac Transposon Mutagenesis: A Tool for Cancer Gene Discovery in Mice," Science, Nov. 19, 2010, 330(6007):1104-1107.

Zhang et al., "Construction and screening of hyperactive PiggyBac transposases," Journal of Northwest A&F University, Aug. 2015, 43(8), 10 pages (with English Abstract).

\* cited by examiner

*(1) PB transposase 5'-recognition site (TR<sub>L</sub> is indicated by single underline, IR<sub>L</sub> is indicated by double underlines)*

TTAACCCTAGAAAGATAATCATATTGTGACGTACGTTAAAGATAATCA<u>TGCGTAAAATTGACGCATGT</u>GTTTATCGGTCTGTATATCGAGGTTTATT
TATTAATTTGAATAGATATTAAGTTTTATTATTATTACACTTACATACTAATAATAAATTCAACAAACAATTATTTATTGTTATTATTATTAAAA
AAAAACAAAAACTCAAAATTCCTTCTATAAAGTAACAAAACT (SEQ ID NO: 31)

*(2) PB transposase 3'-recognition site (TR<sub>R</sub> is indicated by single underline, IR<sub>R</sub> is indicated by double underlines)*

TATCTATAACAAGAAAATATATATATATATAAGTTATCACGTAAGTAGAACATGAAATAACAATATAATTATCGTATGAGTTAAATCTTAAAAGTCACG
TAAAAGATAATCATGCGTCATTTGACTCACGCGGTCGTTATAGTTCAAAATCAGTGACCACTTACCGCATTGACAAGCACGCCTCACGGGAGCTCCAA
GCGGCGACTGAGATGTCCTAAATGCACAGCGACGGATTCGCGCTATTTAGAAAGAGAGCAATATTTCAAGAATGCATGCGTC<u>AATTTACGCAGAC</u>
<u>TATCTTTCTAGGG</u>TTAA (SEQ ID NO: 32)

*(3) PB transposase amino acid*

MGSSLDDEHILSALLQSDDELVGEDSDSEISDHVSEDDVQSDTEEAFIDEVHEVQPTSSGSEILDEQNVIEQPGSSLASNRILTLPQRTIRGKNKHCW
STSKSTRRSRVSALNIVRSQRGPTRMCRNIYDPLLCFKLFFTDEIISEIVKWTNAEISLKRRESMTGATFRDTNEDEIYAFFGILVMTAVRKDNHMST
DDLFDRSLSMVYVSVMSRDRFDFLIRCLRMDDKSIRPTLRENDVFTPVRKIWDLFIHQCIQNYTPGAHLTIDEQLLGFRGRCPFRMYIPNKPSKYGIK
ILMMCDSGTKYMINGMPYLGRGTQTNGVPLGEYYVKELSKPVHGSCRNITCDNWFTSIPLAKNLLQEPYKLTIVGTVRSNKREIPEVLKNSRSRPVGT
SMFCFDGPLTLVSYKPKPAKMVYLLSSCDEDASINESTGKPQMVMYYNQTKGGVDTLDQMCSVMTCSRKTNRWPMALLYGMINIACINSFIIYSHNVS
SKGEKVQSRKKFMRNLYMSLTSSFMRKRLEAPTLKRYLRDNISNILPNEVPGTSDDSTEEPVMKKRTYCTYCPSKIRRKANASCKKCKKVICREHNID
MCQSCF (SEQ ID NO: 33)

WXRE ID: A (SEQ ID NO: 35)

FIG. 6 (Continued)

GAACATTAATTTTATGTTATCTTGTTATTGACTTTATTGAAAATACTACAGAAAATTTGGTTTGAGGCTTTCCATAATAATTTACCCTTACACCTCACA
CCCTTCCATAAACATGTCAGTTAAAAATTGCAGTTAAAATTGAATTGTTCGGGCACTTCTACCTTGATACCTGGCCTACAGTGGGAAAGGTCTGTTCTTTCTTTGGAATA
AGCCCATCAGTGGCCTTGTGTACATTCGTATTTTGTTGTTTGTTTATTACTGTTTTTATTTTTACTTGGGACTAATAATCTGTTTGAAACTGACTGAGATAG
AAAGATGTGATGTTCCTTCCCACTCACTCCGATTTTGATAGAAGACTTGTTTATTTCAAAATTATATCGCAGGAAAACAAGCTGTTTAAAT
TCAGATTATGCTGAAGCAAAATGGTCCTGGTATGAGAAGCAACGTGCTGTTTTACGAGCACAGAGTCCCTTTCTCATAACTGATTGATAGTAAATAT
TTTCCTGAAGAATTATTGCCAACCATGAACAGTGCAACTGTTCACTTTTTTTCCCGTGCTACTTGCTGACCAGCCATTGTCGGTAATTAA

WXRE ID: B (SEQ ID NO: 36)

GATCTGAAGTTTGGATCTGCAGAACCCACACAAAGGCCTAGTAGTGTACCTGCAATTCAGCACTTGGAGGCTGAGAAAGGATCCCAAG
GGCAGCTGGCTAGCTAGGCTAGTGTTAGCTGGGTTCGTGGAGCGACTCTGGTTCAGTGAATAAGATAGAGAGCCAAAGTAGAGTGACATCAGCTTTGGGC
TTCCACACAGCAAATGAGCTCACTTGCATGCAAACACAGAGAAATGCAAACCAAAAGCAAAAACAAAAGGAACACAGGCCAAAGGTGGGTCATTCCTAT
ACCATCCCCTCAGCAGGTGCAGTCCCCACACCCTGACCCAGTTCCCTTCACGAACATTTCAGCTC
CAGAGAACCTGGCCCCACTTTGAAAGCTTTAATTAGAAAGCTTTAAAACACACAGTTTTTGGTAAGCTCCAACATGTTACCTAACATAGCAGTAAAGAATCAC
ACAGCAGTTTGCGTGGTTACAGAAAGGTTGCAAGTAACTTTAAAAACACAGTTTTTGGTAAGCTCCAACATGTTACCTAACATAGCAGTGGCCTCGATT
ACATGTAAGCAGTGAGTCTCCGGCTGCCTGGTTTGTGAGGGTAATGTACTTCAGCAATAGTGACTCAGTGTACAGTGGCTGAGCGTCATCACCCTAAAA
AAGTAAGCGAATTCCAGTCTTCAGAGTTAGCTTTCAGTAAAACCAAGTCAGTGGTGAAATGGCTCAGTAGGTAAGGGCACCCGCTGCCAAGCCCAAGAC
CTGTGTGTCCTGGGATCCCAGTTGGTGGAAAGAGAGAACGGACTCCTCACTCTTTGGTGTTCAAGCATACCA
AAAACAAAACGCAAAAAGGAAGTGGGCTCACGCATAAGGCACTCACTGGCTAATGCCCAGGGCTAATGTTGTGTGTTCAAGCATACCA
TACCTTGATCTACATGATTTTTTACTCCAAAGACACAGCCAGGGTAATGTTGTGTGATGGATCAGTCTTATTTGTTTACTTGTTTACTAGTACTTACTGA
GATTGTCGATGGCTTTAATGTCAACATGAGTGTGGA

WXRE ID: C (SEQ ID NO: 37)

GATCTTCTAGGTCTGGCTCTGAGTTGAAAGGCCTCTGATGCTGGGGCGAAACATCTCTCCCTCTGGGGCTCAGTTTTCTCATCTGTTAGAAAAGGACACAG
CTGACCTGTTGGCTTCTAATAGTTGGACAGAGGCTAGGATTCTGAGTCTCATTTGACTCAGTGGATTCAGGTTTCATTACACAAATATTCTTTAATTCTTAAGTCACTAAACAGCATC
AGCAAGGCAGGGGTCGAGACATGCCGAGCAAGAATGAGATTGGATTCTGACTTCAGGTTCCATATTACCAGTTACAGTAATGGTAAAGTTCATTCATCT
TATAGACTTTTGTAGAACTTTGTGTTTCTCCACTATAATTCGTTACTGTTCCATATTACAGTTAATTCGTTACAGTTAATGGTAAAGTTCTCACAGAAT
TCCTAGTCTTTTCTCTTCATATTTAATCTCCTTTCCCTTTCACGTGTCATATGTCGTAATTGGCATATTGCTGATAAAGTTTTCAACCATGGGAACATGGTC
CCTTGGGTGGTAAGGTAGTAAGGTAGTAGGAGAGACAATTTATTCACTTTTTCACTTTCACGTGTGATAAAGTTTTTCTGTATTTTTAATTCTTCTGTATTTTGCAGTTGTAG
GAGAATAACCCTGCAGCAGTCTGAGAGACCTAAGAGCCGAGTTTGTTGTTAAAGGCTAAAGTAATGTGTATTTGCATTTTAAAACAATTTATACATATGTCACTTTGT
CTTTCTAAAAAATAAAAATAAAAATACCTAAGAGCCGAGTTTGTTGTTAAAGGCTAAAGTAATGTGTATTTGCATTTTAAAACAATTTATACATATGTCACTTTGT
TCTCTTTACCTGAAGTTCCTGGTGCTTTTATTCATTCATTCCTACCTTCCTGTTTTAGGTTCACAGATAGCATTAGTCCTTCTTTGTCCCAAAATTT
TGACTGACTGATTACTCCCCAGACCAATGCTCCTTCCTGTTTTAGGTTCACAGATAGCATTAGTCCTTCTTTGTCCCTATAAAACTTGCAGAAG
TGAGTTCCTAGAGACAACCACAGAATTGCCTAGAAATGCTGGACAGAATTCATGCATCTGATTCCTGGTAAGACCGTCGATGCACTATAAACTTGCAGAAG

FIG. 6 (Continued)

```
CTGACAGCAGGACTGTTCTTCACTTCAACTCATTTATCCCTTCCTTTGGGTTCTGTCCAAATCACATCACCAGGATCACAAGGACTAACATCAGGATTG
AGACGTAAATAGAAGATATCACATTGGATTTCCACCATTGAGCCACCACCTGCCTGATAACTTTCACAGTCCCAGGAGATATTATACAA
GTTACTAGGGCAAAAAGAGATCAAAGTCTGAATCAGCTGTGAACCCTATGAATGGCAATACCTACTTATCAGGCAATACAAGCCCACCCGTGTGATAG
TGGAATAACAGTAATATGGGCAATCACTGGATTGAGTCCTGGCCCCACTGCAGAGAATCCATGCAAGCTGTAAATCCAGGAAGAAGAAAAAAAAAC
CTATCACTGAAGAAGACAATAAACCCTAGAAAGGAACTTACTACTTCTTAATTAGAGAATTCTCTCTAGTGAATTGGTTGTGGATTCAAAGACTCATAAATACCAAGGGTGCTAAGAA
TGCTCACAAATTATCCACTCATTCTTAATTAGACAAGATTTTTATACCTCATCTTGTATCATGAACTCACAAAAGCTGCAGTTTGTTAGTGCCAGGACTGTGTGACATTGTCACTAC
TGAGCGACAATTAAGAACTCAGCCCTAAACTCAGCCCTAAACACAATTTTTATACCTCATCTTGTATCATGAACTCACAAAAGCTGCAGTTTGTTAGTGCCAGGACTGTGTGACATTGTCACTAC
GTGAAAAGAGTGAGAAGGGCTGCCAATATCATCTTTGCTATCATGAACTCACAAAAGCTGCAGTTTGTTAGTGCCAGGACTGTGTGACAATTGTCACTAC
CAACACTCAGCCTTGGGTGGGAGGAGGGCATAAGTCCATTGGCCAGGTCCCATTGGCACAACTCTAGGAGAATCACTGGACACAATCAAA
TTATGTATCCATCCATGAATCTACAAGGCTCCATTGGCCAGTCCAAAAATTCACTGATGAAACATTATATACACATATGAA
AATATGAAAAGAGCTTTGTAGCCATCTTTTTTTTCTGACAAGGGTGGGAGGAGGCATAACAAGGAAGGTAAAATAATTGATTGCATTATATACACATATGAA
ACTGTCAAAGAACGCAATTTAAAAAGTACATAGTAAGTGGTTTCCATTGGTTTCTTTACAGTGTTCTTTACAGTATGTCTTGATTA
TCTCTATCCCTGACTCCCATGTCACCCCACAAACACCCTATCACCCCATTATATCTCCCCACCTTATCACCCCTTAATTTCTTTCATTTTACTATTTTATAG
ATAATCCACTGAATTCAATTAGTGCTTGGTCTGTTGGAAAGCCGAAGGAGACCGATATGTTGGCTTGATTTGACACAGGTCTTCTGCAGGTGACCAAGAT
GAAGTGACTTGAACTGCATCAGTTCTGTCAGTGGGGGGGTGGGGGAGTGTGTGTGTGTAACCACATCAAGTAGAGAAATGTGCTTCTCACAATGTGAGCTTCCTCTCAGTGTCT
CATATTCTTTCTGCGTCTTCTTCCTCTGTAACATAGTAAATTTGTACAGACGGTCACAAGTCACAAATTTGTAGACTACACATGATGAAATTTGCAAT
GACTTTTGGAGTACTTAACATGGATTTGAAATGTCCATTGGGCTCCCTCTAGCTCCTAGCTCCTAGCATCAGTTGCTATCTTACCATCTTCCTTCCTTG
TAGGAGTCGGCCACGTTTCCCACTCAGACCTTAGCTCCTCTCAGTCCTGGCCATCGGTGTCATCGGACTTAGGATTATTTGCCCTCTTCC
TAAGCTCATAAATCCAGACAAAGTGAAAGTCAAATCTCAGTTGGGGGGGGGTGGGAAGTGTCACATCTAAGTAGAGAATGTGCTTCTACAATGTGATCGAGCCCCTGAAAAGCCTGCAGTA
TGTTCCACTGCATCAGTTCTGTCAGTGGGGGGGTGGGAAGTGTCACATGAAGCCCGGTCTTTGTGAGGAAATGGCCATTGGGCCAGAATGGGGGGCTAAACAATTTAGG
CAAAGCTGTCATAATGATGAAACAGAGTATCAGTCACAGAGTATCAGTTTGAGGAAATGGCCATTGGGCCAGAATGGGGGGCTAAACAATTTAGG
CATGTCATCATAGAGGAGGAGCTTCTTTCCCAGTGCACACGAAGGCTTCAGGTCAGGTTTGAGGAAATGGCCATTGGGCCAGAATGGGGGGCTAAACAATTTAGG
CTCCTTGGTGCTGTGCTTGAACCCTCCGTTTTCTCTGCGCGGGTCAGGTTGAGGAAATGGCCATTATGCCTAATTCCTAATTCCTAATTCATACAGAGTTTCAGCTTTAA
GGAAGACAGAGATTAATAGCGGTTGAGATGATTTCAGCTGTGCCTTAGGAGACTATGCTGTGTTTAGATTTGCCTGTGTTTAGATTTGCCTGTGTTTAGATTTGCCTGTGTTTAGCTTAGATTTGCCTGTGTTTAGCTTAGATTTGCCTGTGTTTAGCTTAGCTTAGCTTAGGT
GCTCTAAAAACTCACTTCAGGCTCTAAGCCTAGCAGCACTCCACCAGTGGGAGGGGCCTAAACCAGAATGGGGGAGCTAAACCAGAATGGGGGAGCTAAACAACCTTACCAACT
CCAGTCGACAGCCAGGATCCTCCCTTGTCTGCTGCCAGCCAGTTGGAAGTTGGAAGTGGACTCCCCTGTATCTCATTATGAT
ACCAAAGTGAGGGATCCTCCCTTGTCTGCTGCCAGCCAGTTATTGCATAATATTCACATTGCATAAGAAACCACTCTCTTCATTTCTATTCTATCATAGGATTTCT
GCTGTTCACAAGTTGAAGTTGAAGTTGAACTCAGCCCTGTTGCTTAGGCTTTGCTTAGGCTTTGCTTAGGCTTTGCTTAGGCTTTGCTTAGGAAAGA
AACTTAACTTGTTGAAGGTGTGGATATTGACATCTTTGAGAAGAAGAAGA
```

*WXRE ID: D (SEQ ID NO: 38)*

```
GATCTGTGTAGCTGCCACAACACTTGATCTCGGAGTGAGGCCCTAACTCCATTGATGGGTGTCAGTCTCTCATCAGTGAGGCCCTAACTCCATTGATGGGTGTCAGTCTCTCATCAGTGTTAGCAACAGGAGAT
CCAGCTGACTGCCTCTCAAGTTATACAGTGTGTGCCACCAGCAGCTTGCACCAGCAGCTTGCACCAGCAGCTTTGGAAATAAAGTTCATTCCTACCTTGCA
```

AGGAATTCCTATAAAATTCTGTAACTTGACAAGTTTGTGAAGTCTATATCTACTCAATACAGTACTTGAAGTTCTAGATAGACCCATTAAACAGCTAAA
GGACAACAAGGAAGAGGAAGAAGAAGTAGAAGTGTTGTTACTTGGTGATGATATAGTGGTACCACCTAAGTGACTAAAAATTCATCAATGGAAGTACAGG
TGATTAAAACTTTCAGCAAGTGACGGGATACAAGAGTAACTAAAAACAACCATTAGCCCTCCTATGTAAAAATGGCAAACAGCTTGAGAATGAAATAA
AAGAAGCAGCAGCAATCACAATAGCTTCAAATAATATAAATACATTCTAGTAACTCTAACTTGTTGTTTAATTAAAAAAACTTTAAGTGTTTGAAGAAAG
AAATTGAAGAAGATATGAGGCGATGGAAA

WXRE ID: E (SEQ ID NO: 39)

GATCAGGAGTTCAAGGCCACACTGAGGTACACGAAAATTCAACCAGTCTGATAGATATAAGAGCTGGGTGCGTGTGGCTCGCACCTCAGGTGGAGACAG
GAGTATAAGGCTGGAGGAGGCAGTATTTAGGCTTATTCATATAGAGGATTTGTAAAGACACAGGACCTCCCAGCACTTCCATCTGAACATTTGGTACAG
GTAAGAAGTCCCTATAGAGTTGGCTCCTTAATTCTCTTATGTCTCAAACACACATAACCCAATTATCTGACAATTATCTGACAATCTCACTCAGCATCTCAC
AATTTGAAGAAATGCTACAGAGCACCTTTTAACCTCTACAAACACATAAACAGAGAGAAGAAGTCATGTCATGAGAACCCTGAGGGGGCAGAGAGAGACA
GAGACAGAGAGACAGAGACACAGAGGCCTAGAGGAGCCCTGTGACACAGGAAACAAATGTAATAACAAATGTAATAACAACTCTTCTACAACTGGCCCTTGTCCCGTGCCCACACCCATCT
GTGGCCAGGACACAGAGGCCTAGAGGAGCCCTGTGACACAGGAAACAAATGTAATAACAACTCTCTACAACTGGCCCTTGTCCCGTGCCCACACCCATCT
GTGCAGAAGCTTTATCATCAGCAGCACTCTGTCCTTCGCTGGGGTATTTTGGCAATGCGTTTCGCTGCAATTGAGCAGTGATGTTTCAAGTGCACTAGTTG
TATGGACCTGTCCCACAACACAATCTCCAACACAATCTCCAACAATCAATGCCACATTGTAAATCAAAACAACATTCAGGCTCCCCTGTGAATTGTAAGATTTTATTATTGGAATCCTGGT
TTCCCCCCATATTCTCCAACACAATCTCCAACAATCAATGCCACATTGTAAATCAAAACAACATTCAGGCTCCCCTGTGAATTGTAAGATTTTATTATTGGAATCCTGGT
TTTAGATACCTGGAGGGTAGGGTAGGGCTTGCTTCATCTATTCAGGTGTGTAGGCAAGTGGCTCCCTTGAGTCTATTGCCCAGATGGATTCATCAAC
AGAATTTGTTAGCATCTATTTCTGCTGCAAGAGAACCGGTGAGGTATCGGCATCATTCACTGAAGGACAHTCACTGAAGGACATACATGGGACAC
CTCATGGGAGGGACTGAAACCTGTCTGCCAGAGCACCTGGGTCTGACCAT

WXRE ID: F (SEQ ID NO: 40)

GATCTCTCAGCTTCCTGCTTCTTTTAAAAGTATTTTATTTTATTTTTTATACCCATTGATGTTTTTGTCGTGGGTGTCGGATACCCTGAAACTGGAGGTT
TTCATTTTATTTTATTTTATGTTAATCAATGTTTTGCCATGGGTGTTGCGTGCCCTGAAACTGGAGCTACAGACAGGTGTGAGCTGCCATGTGGGGCTGGGA
ACTGAACTTGAGTCCTCTGGAAGAGGAGTCAGTGCTTCTTAACTAGTGAACTGAAAACCAAAATAAACTTTTTAAAGTTGCTTTAGTTCATGGCATTTTTATCACAAC
CTCTCCCCACCATTAGTGAATGCCCCCCTCAGGAAACCTCTGGAACTCTCGGAACCTCGGAACTCTGGAACTTTTTAAAGTTGCTTTAGTTCATGGCATTTTTATCACAAC
AATAGACAAGAGAAACTAATACAGTAATACAGTAATACAGTAATGGCTTTTTAAAGATTTGACAGATTCATGTAAGTATATAGTGAAGTATATAGTGAATTGGGTCATTTTTTCACCCTTTAA
TACCATTGTCATCCTCCTTCCTCCTCCGCGCCCATGGTACACGTGCCAGCCCTTCTTCCTATGTTTATTTATTTATTTATTATAAAAAATAGCCCATTCTATCCTTCCACTTTTTACTACACCTTACTGGT
TGTGTGTGTGTGTATGTGTGCTCGCCATGTGCACAGTGCAGAGAGAACAAGGACAACTTTCCGGGAGTCATTTCTATCCTTCCACTATTTTAAAAATAATCTTTGATGCTTTCTATCAGT
TATATATGTATGTGTATGCCATTAGCCTTGCCAGCAGTGTACATGTGCAGAGAGAGAGAACAAGGACAACTTTCCGGGAGTCATTTCTATCCTTCCACTATTTTAAAAATAATCTTTGATGCTTTCTATCAGT
TAGAACTCAGTCAGTGATAAATCTATAATTATTTCTCTAAGACTATTTGTTTTCCACAAACAAAATGCTATAAGCTGGGAGATTTATAAGAAGAGATACAT
ATCTTGGCCACTGATAATCTATAATTATTTCTCTAAGACTATTTGTTTTCCACAAACAAAATGCTATAAGCTGGGAGATTTATAAGAAGAGATACAT
TTGGCTCACAGCTCTGGAAGTCCAAAAGCTCCAAAAGCCAAGTGTTCCAGGCTTGGTCTATGGTTTTCATCATTTAAGGCCGCCAATTCCATCACAAGTGTTCTCTTCC
TGACAAGAAATGTTACAAAAGGACAAGAGGACATTCTAAAACCCCACACCCAAATACTATTAGCACAAGACATTGGAGATTTTAGTTTCAATCTTAGCTTTAGG
CTATGATTTCATGTAATTCTAAAGCACATTCTAAAGCACATTGGAGATTTTAGTTTCAATCTTAGCTTTAGG

FIG. 6 (Continued)

GGAGAGAGACACTCAGTTCATAACAGTATCCCAAGATTCCAGTATCCAGTGCTGCTGTCTCAATGCAATACTACTCAGAAG

*WXRE ID: G (SEQ ID NO: 41)*

GATCTTTCCATTTCTGGTATCTCTTTCTTTAATTTCTTTCTTTTAAGACTCAAAGTTCTTGCTAGACAGTCTTTCACTTGTTTGGTTATCATTACCCCA
AGATATTTTATGTTGTTTGGCTATTGTAAAGATGATGATGTTTCTCTGATTTATTTCTCAGCCCATTTATCTCCTGTGTATAATAGGGCTAGTGATTTTT
TGAGTTAATCTTGTATCCTTCCACTTAGCTGAGTGCTGTTTATCAGCTGAGTAGTTCCCTGGTAGAGTTTTTGGGTTACTTATGTAACTATCATATC
ATCTGCAAACAGTAAAAATTTGACTTCTTCCTTCCCTTGTATCCCCTTGTTCTCTTGTTGGGGATGTTCAGGTCTTGCTGGCGTAGAGTCCTAGTGGTGTCATAATTCTCAAGTACA
AGCAGAAGTCATTCTCTTCCTTCTCGCTTCCATCTGTGTTCAGGTCTTCCTCAGTGGGTTCAGGTCGGCCGTCTCTTCCTCCCAGTGGTCGGTTATTGTTTTTTCTG
TTATTGAATGCGTTTTATATTGTTGTCTTCCTTCCACTCTCTTCCTTCCAGTGGGTTCAGGCTCCAGTGGGTGTATGGGTCCAAGGTTC
TCTTTGGTGGATGCGAAGAGGGTCTCGATCAGACTTGAGGTTGCTTGGTCTCCTACACATGTCTGATGGGTCTTATGGTGGGGTGGGGTGGGGGAACTGG
ACTAGCACAGTGATGTCATCAGGGGCCAGGGGCCAAGCTCTACAGACTTGAGTGAAGGTCATCAGATCATGTAGGCAGATGATAAGCTCAGGGAGAGACA
GGCAGAAGTCGGGCTCAAGGCAGGGGCCAAGCTCTACACGTGAAGATTGAGAGAAAGGTGGATTTTTAAAATGAGAGTTCATGTAGGGAGCTAAAAGGAGAAATTAA
ATGACCTATTTCTAAAAAACTGATGTCAAAGAAGGTGGATTTTTGTCCCATTGTTAGAGAGAGAAACATTGTTGAGTGGGATGT
GGATGAGACTCTCAGTTTTGGACTTGGAATGTTGGATTTTTAGAATCAAATCTCAGGGAACATCATTAGCACAGAGGGACCCCTGTTTGGGTCTTGCCAGATGCTGAGCTTCA
CACCTCATGACTTAAAGAATCTGAGGTTTTAGAATCAAATCTCCCACATTTCCTGTTTTTCCTGTTTTTTCCGTTTTTCCTAACTTGTATAGACTCTGGGAAAAGAAGTACCAG
GCTGTCTCCCTGTTTTCCCACATTTCCTGTTTTTCCTGTTTTTCCTAACTTGTATAGACTCTGGGAAAAGAAGTACCAG

*WXRE ID: H (SEQ ID NO: 42)*

GCAGTACAACATCTCTTGCTTTGCTCGGGAATGTGGGCACTCTGAATGTGATCCTGACCCTTTGGGAATAGAGCAGGTCCATCCGGGACTTCAACCC
ATAGAATCTAAACATGGGAAACCATATTTATCAAGGTCTTTCTAGCAGGTCATCTATCCTGCTACTAGAATCATCTATCCTACTAGAGGCTACAGGAG
GTGTCAGAGAACTCACTTTAGAGTCTTCAGTACAAGATAAGCTTCAGGCCAGCTCTCCTTCCAAGACCAAGTGGGTTG
GAGAGAGAACTCTGGCCTAGCAGGCTTGAAAGAAACTTGGTTGGGACTGTTAACTTCAGTCAATTGCTCCTTGCAGCAGTATTGTTAACATGAGGCAG
AGATGGGGAGGGTGAAATGAGAGGCATTGAGAACTGTTGATGCCCAAAGAGCTATTTAACTAATTAAACAATTAAACTGTTAAGAAATTTTT
GTGGTTTTATTGTATCATGAGGCATTGAAAACAAAATGAAACAAAAACAAAAACCGACAATCTTTGCATTACTTAAGTCTTTCCAAGGCATGCGCTGGTACAAC
GCAACTTGTCAGTAGATTAAAAACAAAATGAAACAAAAACAAAAACCGACAATCTTTGCATTACTTAAGTCTTTCCAAGGCATGCGCTGGTACAAC
ACAAAACTTCTCCCTGTCAGATGCAACTAGTCTAGCATCCAAACATCATGCACAACACCGTGGTGACAGAGGAGGAAAACAGCGTGAGGATCTCGGCCC
TGCTCATTTGTGTATGATATTTGGAGCATCTGGAGGGCAAGCTCTTTAATAGAAACCATCTGGCCAGGAATCGGTGGAAACCCATG
GTCAGCCGAAGTTGTGCAGGGCAAGCCTGAACATGTCAGTAAGAGGGCTAGGAACAGGAAGAAACGTTCAGTGGTAGAACATCTGGTGGGAACGAGAATACAG
ATGGGATCTTCATCGGCCTGTATGGAAGAAAAAATGATTCAGTAGAGGGCTAGGAACGTTCAGTGGTGTGAAGTGAAACATTGTTGATCATG
ACTCCAGGATCAGGCCACCTACTCTCTTAAACCTGCCAATGTATCATTGAAAAGGCAGCACATTTACCAGTAAGGCGACAGAGCAGAGACTTGCCTGTCT
CAAAAGTCAATAAATGGCTGCTCTCTGGGTAGATGTGATCAAAAGTAAAGACTCTTGTAGCACTTATTAATTTATAGTACCAAAAAACTGTAAGCAA
CTAAACTGGCCAATGTCTCTGGGTAGATGTGATCAAAAGTAAAGACTCTTGTAGCACTTATTAATTTATAGTACCAAAAAACTGTAAGCAA
TCTTAGTGTTCAAGAGAGAACTGACAGAGAGTAAGGCTGACTTGTGTAGGTAGTGCTTCTCGGGTCTAATAAAGAAGAGCTTTGGAAACATTAAGCAA
CCTATTGCCCGCCCCTCCCACACACGCCATATCGGATTCGGAAATCGGCCATATTTGTCCTGCTTTAGGAAGAAAGCTTTGGAAACATTAAGCAA

FIG. 6 (Continued)

GAACCAGAGACCACAGGGGACACACACCTTAAAAAAGAGACCCAAGGTTGTGCTCAAAGGGTAAAGGCCACTTGCCCTATAAGAGACTAGTGATCGAGTTGGAAGGAG
AGAGAGATTCCTCTCTGACCTTTACATGAGTGTTGTAGCATACACAGAATACACTCATCAGTAAACACATAACATATGCACAATGTTGCTTTTTCA
CTAAATTCTTTTCTTTCCTTTCTTTTTTGGTTTTTCGAGACCAGGGGTTTCTCTGTGTAGCTTTGGAGACTTTCCTGGAACCTATCCTGGCACTCGCCTCTAGAGACCCAG
GCTGGCCTCGAACTCACAGAGATC

*WXRE ID: I (SEQ ID NO: 43)*

GATCTGAAGTTTGGGATCTGCAGAACCCACACACAAAGGCCTACGGGCTTAGTAGTGTACCTGCCAATTTCAGCACTTGGAAGGCTGAGAAAGGATCCCAAG
GGCAGCTGGCTAGCTAGGCTAGTGTTAGCTGAGCAGCTCTGGGTTCGTTGGAGCGGACTCTGGTTCAGTGAATAAGATAGAGTGACATCAGCTTTGGGC
TTCCACAGCAAATGAGCTCACTTGCATGCAAACAGAAATGCAAACAAAGGAACACAGCCAAAGGTGGGTCATTCCTAT
ACCATCCCCCTCAGCCAGGGTGCAGTCCCCACACCCTGACCCAGTTCCCTCATGATGTTAGAGAACAGATGTCTGTTGTGATTGTGGGAACAGATAGGTTAAAGAAATCA
CAAGAGAACCTGGCCCACTTTGAAAGCTTTAATTAGAAAGTGCAATTACCCGGAACAGATGTCTGTTGTGATTGTGGGAACAGATAGGTTAAAGAAATCA
CACAGCAGTTTGCGTGGTTACAGAAGGTTCAAGTAACTTTAAAACACAGTTTTGTGAGTGTAAGTCTCCAACATGTTACCTAACATAGCCATGGCCTCGATT
ACATGTAAGCAGTGAGTCTCCGGCTGCCTGGTTTGTGAGGGTAATGTTACTTCAGCAATAGTGCTGTACAGTGAGTGCACCCGCTGCCAAGCCCAAGAC
AAGTATCGAATTCCAGTCTTCAGAGTTAGCTTTCAGTGGTGAAAACCAAGTCAGTGGGTAAAACCAAGTGGCTCAGTAGTGCCTTCCTACTTTTTGGTTGTTCAAGCATACCA
CTGTGTCCTGTCCCTGGGATCCAGTTCAGTGGTGGAAAGAGAGAAGTGGGCTCACGATCTCACTGACCTGGACTCTCGTACTCTCGTGTGGTTACTGTTTACTGA
AAAAAACAAACAAAAAGGAAGTGGGCTCACGATCTCACTGACTGGACTCTCGTACTCTCGTGTGGTTCAAGCATACCA
TACCTTGATCTACATGATTTTTACTCCAAAGACACAGCCAGGGTAATGTTGTGTGATGGATCAGTCTTATTTGTTTACTGTTTACTGTTTACTACTGA
GATTGTCGATGGCTTAATGTCAACATGAGTGTGGAGATC

*WXRE ID: J (SEQ ID NO: 44)*

GATCTTTTGTGGACTCAGAAGGTCGCTGCTTCTATGAGCAGCTCGGAGGAGGAGGAGGAGAAGGTCTTTTCTGGTCTTCTTCAGCAAGGTTGTCCCCTA
TCCACAGCCCTCATCCCGAGTCAAAGATGAGATGGTAGGAACTTACATATCCATCCTGGACCAATGGCCATTCAGGATATTTCATGCTCCAGCAAGCATCCAATAGTTCATTGA
TACTGTGGGGGCTCTGGGAGAATTGAGACCTGTCTTACCCTGGACTTTTCCACCTGGCTCAAGAAATTCAGGCAAAGCTCCTG
TATCCTCCCACCAAGGCAGAGAGTTTGGATGGACTTTGGGCTGGTCAACTGGTCAACTCTCCTTAGTGATGAACAATGGCATGTCCCTACCTCTGACTAAGCTGCC
AAGTTTGGAAAAACCCAGGCTGCTCGAGCCTGGGGTTTCTCAGGGATATGTCTCAGGTAAGTCCCCTACAGCTCTAGCATAAAAGCTTTGAGAA
ACAATGTTCCCTCTGCCTGCAGCCTTCATGCAATCTTTGGGGACAAGAGTGCATCATCAGACCCCAGAAGTGTCATGGCGTGGGGTCACATGGTAGTTGACAAGAAGAAGCCAAACCCT
CTGGACTCCATGCAAGGTCACCTGAACCGTCAACTTTGGGGACAAGAGTTGAAGCCCAGGCTGGGAAATGGACCCCAGCCCTAAGGCAGATTTCGT
TTGACCAATCTGTACCTGAAGCCTGATATGGCCAGGAATGGACCACCTGTTCATCCTTATCACTCTATCACTCTATTAGGTAATGAACACCACTTGCTTGCT
GTTGCCTCAGCCTGATATGGCCCCTGCTGAGAACTTACTGTGTGCATTGAGCCACTTAGGTAATGAACATCCTATTAGGTAACTCTTATCCCACCCCCC
CTAGCCTGACTTTCCCCCTGCTGAGAACTTACTGTGTGCATTGAGCCACTTACTGTATCACTCTATAGTTTCTTCATTCCCATCCTGCAACATCTAGT
CAGACTGTTAGCCAGTAGCCTAACATGGCTAGTGGTGGGTGGCAGGACCATAGGTAGGCATAGGTATGGCCCTGTGTATCGGTGTATCGGTGATCTAGT
GGGGCTACCAGTGGGCCTAACACTAGCTGCTTATAAGAATAGGTATGCCCCTTGCCTGTTTTCCATCTATAGTTTCTTCATTCCCATCCTGCAACATCTAGT
AGTAAAAGTTGCTTTGTTTTTGTTTTTGTTTTTGTTCAGTTGGGCAGGTCCAAAAGAAAGAGAAGAGGGCCCTCTGTGTTCAGTGGCCTCT

FIG. 6 (Continued)

CATACTCCTCAGGGCCCTCTTTCTCATGAGTGCCACCTACCCGATACCAACCTCCTCTCCTAGTACCTGGAGAAGCAAAAACCCAGAACAGGAAAATAAAGG
TCAAAATAGAGGTCATAGGGAAGAAGCAGGCCTAATATTAACACTTTTAAGAAATAACTGGGTTGACTGTCCAAAAGCCGCACATGTCTAATGG
TGTTGAATGTCCATTCTTATCTGAAAATTGCTTAGAAGTGAATC

*WXRE ID: K (SEQ ID NO: 45)*

CCCTTGCACATAAGCGGCATGGTGTCCCCAGCCTGGGAGGGCTACGTGTGATATTTCCCCCTGGCATGTGAAGAAGTCTTCAGTGGGCCAGCAAAATGCT
TTCTATGGAAAGTCTGTGACACTGGCCGTGCACTTACCCTGCTTGTGTAGAAAGTAAATTGGCCATGGCCCTGTTTAGTTGCAGCATTCC
TAGAGTAAAAGAAGAACTTTTGATGCCATTGAACCTAAAGCTCAGAAAGTGAAAGCTGTCAACACATTCTAAATCTTTACCCATG
TTTTGGAAAAATACAAATAAATTCAGAAATTGCTCAGTAACTGAATTGCTATGTCTTAAAAGCATTTACTATTGACATGTTTTTGGGAGAATTAAAGTTAGC
TTGGAAAATTAAAAAAAAAAATGAAGAATTCAAACATATTGAAAAAATAGATTCTTTTACATATAGAAGTGTCATAGTG
CCACTCTATTACATTGAATCATTAGACTTGTTATTTCAATAATTATTCTCAATATATATTGCTTTTATTTTTCTGCTAATCTTTTATTTTAAATTGGTTCTT
CACAATCTTAAGTGACAAAATATTCTCAATATTGGCTGTAGTCACTAATATGGCAGACATTCATCTTTCATCTTTCTGTAGTCCTGTACCCATTCTTGATG
TTACTGTAGGAATTATTGACCAACTCCCCTTTAATATACTGGTTCATTTGGTTTTGTCAGATTACAGGATTCATCTTTCACCATTGTAGTTCTGTACCCATTCTTGATG
AAAAAGGGTAGATTTGACCAACTCCCCTTTAATATACTGAGGCTGTAGTCACTAATATAAATCACATTAACATGGAAAAAGTAC
AATATTTATTTAGTTGCAATTTGTCAGTGTTCAGTAGTTCAGTAGTTCAGATTTTAGGATGTTCATGCCTTTCTTGG
GTAGACTTTAAAAAGTGACAAGTTGTGAGAAAAGCAACTACCATTTTGAGGATGTTCATGCCTTTCTTGG
TCTCTACCATTAGTAGAATCATTGTTTTCTAATGAAAGGATGGATTCTGTCACATCTCCCAAAAATTAGAATGGTCCTATATTGTCCATTTCTCAAA
TATCTTTAATTCATAAATAACCAAAGTGTCAGGTTGCATGACATGTTTTGGACTACTTGATTTTGGGACTACTTGATTTTGGGACTACTTTAAAATG
CAAGCACCATTCTAATTAGCTGGATC

*WXRE ID: L (SEQ ID NO: 46)*

GAAGTTTGGATCTGCAGAACCCACACAAAGGCCTACGGGCCTTAGTAGTGTACCTGCAATTTCAGCACTTGGAAGGCTGAGAAAGGATCCCAAGGGCAG
CTGGCTAGCTAGGCTAGTGTTAGCTGGAGCGACTCTGGGTTCGTGGAGCGAGCTCTGGGTTCAGTGAATAAGATAGAGACTTTGGGCTTCCA
CAGCAAATGAGCTCACTTGCATGCAACATGCAAACACACATGCACAGGCCAAAGGTGGGTCATTCCTATACCAT
CCCCTCAGCAGGGTGCAGTGGGCTCAGTCCCCACACCCTGACCCCAGTTCCCTCATGATGTTAGAGAAAATAACTTTGCCCCCTTCAACGAACATTTCAGCTCCAAGA
GAACCTGGCCCACTTTGAAAGCTTTAATTAGAAATGTGCAATTACCCGGAACAGAGATGTCTGTTGTGATTGTGGAGACATAGGTTAAAGAATCACACAG
CAGTTTTGCGTGGTTACAGAAGGTTGCAAGTAACTTTTGGTAAGTCTCCAACATGTTTACCTAACATAGCATGGCCTCGATTACATG
TAAGCAGTGAGTCTCCGGCTGCTGGTTTGTGAGGAATTAGTTACTTCAGCAATAGTGCTGAGGCTGTACAGTGAGGTAAGGCACCCGCTGCCAAGACCTGTG
TCGAATTCCAGTCTTCAGAGTTAGCTTTCAGTAAAACCAAGTCAGTGGTGAAATGGCCTCGACCTCCTGCAAGCATTAAGTAAAAAA
TCCTGTCCCTGGGATCCAGTTGGTGGAAAGAGAGAACGGAACTCCTGCAAGGTGGCCCTCTGAATTCTGCCAGACATTAAGTAAAAAA
CAAACGCAAAAAGGGAAGTGGGCTCACGCATAAGGCACTCACTGGGTAAGTTGTGTGATGGAGATCTTATTTGTTTACTTACTTGAGAATTG
TGATCTTACATGATTTTTACTCAAGACACAGCCCAGGGTAAGTTGTGTGATGGAGCAGTCTTATTTGTTTACTTACTTGAGAATTG
TCGATGGGCTTTAATGTCAACATGAGTGTGG

FIG. 7

Reverse complementary sequences for WXRE

WXRE ID: A (SEQ ID NO. 47)

TTAATTACCGACAATGGCTGGTACAGCAGCAAGTAGCACGGAAAAAAGTGAAACAGTTGCACTGTTCATGGTTGGCAATAATTCTTCAGGAAATATTTA
CTATCAATCAGTTATGAGAAAAAGGGACTCTCTGTGCTCGTAAAAACCAGCACGTTGCTTCTCATACCCAGGACCCATTTTGCTTCAGCATAATCTGAATTTAAA
CAGCTTGGTTCCTGCCGGATATAATTTTGGAAATAATAAAAAACCAAGTCTTCTATCAAAATCCGGAGTGAGTGGGAAGAACATCACATCTTTCTATCTC
AGTCAGTTTCAAACAGATTATTAGTTCCCAAGTAAAAAAAACAGTAATAACAACAACAAAAATACAGAAAAATACACAAGGCCACTGATGGGCTTATTCCA
AAGAAAGACAGACCTTTCCCACTGTAGGCCAGGTATCAAGGTAGAAGTGCCCGAACAAATTCAATTTAACTGCACATGTTTATTGGAAGGGGTGTGAGG
TGTAAGGGTAAATTATGGAAAAGCCTCAAACCAAAATTTTCTGTAGTATTTCAATAAAGTCAATAACAAGATAACATAAAAAATTAATGTTCTCAGTTT
TTTTCATAATTAAAAAACATGAAGTTGACAATTAGTTAGTTGACAAATGTGATTATAGAGTTTAAAGACTAAGCTCAATAACCGCTGTCCATTTAAA
GCTACAATAAAATATAGAGCTCATCATGTTCCCAAACAAATCCCATAAAGCACCCAGGGCTGTGAGCAGCAGCAGGCCTGGTTGATATGGCCAAAGTACATCGGACA
TGGCATGGTGGTGCATCAGCACTTGGGAGGCGGAGGCAGGTGGATTTCTGTGAGTTGTGAGATATTTCAAATACTTGGACCCCTCCCATTTTTATTTTAAATG
GACAGACAGACAAACAAAACAAAAAGCAAACTATATTCAAGACTGCCTAAGGTAGCTTATGGAAGGAGCAGCTGTGCTTCCTTACAGGAACTGAATAGTTACAGGGC
TTTCTTTCTTGAACTCTTTCTTTCTTCAGGAGACGTTTCATCCTCTGCTTTTGAGAAGGAGGACCAATGTCTTCTCTGTAAAATGCAAACAAGTAATAATTA
AAAGGTCTAAGACTACAATTAGTATTGATACCCAAACCAAAATTACTCTGACTGAAATTCAGTTGCTTTGAAATCAGTTGATTCAGAGACGGCCAGTTTCTGAAGGAAA
GTCCTCACAGCCACGTCAGTGTAGCCAGCAGACAAAACTACTGTTAAGAACTAAAGGTGAAGAACAAGAACTGAGAACAAGATATAACATGTTTAGCAATAAGAAAGG
CTTTGAGTCATTTCTTTTTAAAGGTCAAGCAGTAAATGAGGCCAGGAGGAGGCCACTGCAATAAACATTTTTTTCAGTTGTTGCTCAAATCTGAAGCAA
AAAACTCTCATTGTTGCCATGCTAGGCTAGAGGGCCAATAAAAGGAAGAGCAGCAGGAGGCCATTTAAAAACAAGGTCACCATCTGGGACGAGAGAATGGGACTGATG
TGAACTAGAAGACAGGATGTGGGCCAATAAAAGAGGTGTCAGAATAATGTTAAAACAAGCAAGGTCACCATCTGGGAGCAAGTGAAACAGACTGGTTA
AGGGGACAATGAGCAAACTTATTCCTCACCCAGGAGCATGGAAGGAATTATACCGTGCCGACGCGCCACACGATTTCTAACCGTGCACCACTGAAG
AGCAGCCAATGAGCAAACTTAATTCCTCAGAAGTACTTGTGATGAAGGAGGAGAGTAACTTGTGATCTATACTCAATGCTAG
TAGAGGGTAGAAAAACAGATCAAGGTAGCACTTGACAAACCGGAAATTCCACACACTATACCACACTACTCCCTCTTTTTTTTTGTAGCAAATTA
ACGTACAGGAAAACAAAAGGAACAAAGGAACAGATGCTCAGTTGGCCAGCTCTCAAATGAAAATCCATTAAAAATTGTCGCCTGTCCTTGGATTGGTGGTCATGCGGAA
ATTTGTGCCTTGTTTAGCCAGAAGTAACTTGTGATGAAGGAGGAGAGTAATTGAAAATTAAAAATGTAAACTTACACTATTCTTACATTTCTTACAATTTCTTACATGGCCAC
ATATAAAAACAGATCAAGGTCACAATTTGATGAACCTACCATTTGCAGCTACCACCATTTGCAGCCATGTGTATTTTGGGAAATATAATAAAAATTATTGTTGTCCTATGTCCCTATGTCCCTGATTGGATCA
AGATGTGAACTTAAGGCACAATTTGATGAACCTACCACCATTTGCAGCCATGTGTATTTTGGGAAATATAATAAAAATTATTGTTGTCCTATGTCCCTGATTGGATCA
AAGCTGTATGTTTGGCAGTAATAAAGCAAGGTCAGGAACTGCCCATGTATTTGGGAAATATAATAAAAATTATTGTTGTCCTATGTCCCTGATTGGATCA
TGTCCCTCCCTAACCACCTAAGTGTAAGAACTAGAGTCTTCCATGAACAGAGCTCTTCCATGAACAGAGCTATGCAATAAGTAATAAATGCAATATGCCAATTAGAACAGATTAATAAGAGAGA

FIG. 7 (Continued)

```
TCCCAGAGGGGCTTAGCTCATCCCTTCCATCCTGAGATTATATTATTATAGCAAGGATTCCATCTTATGAAGAGAGAGTCAACTTCCAACTAGACATTGAATCT
ACTGTCACCATGATCTTCCCATATCTAGAACTATAAAAATAAGTCACTGTTTATAAGCTACCTTGTTGTAATAACACAAAGAAAATT
AGCTCTTTCTTGAGATTTATAACAAAGATGGAGTTGACATGACATCAAGTCCTATCTCTAATAATGACAGTAAATAGGGGCCTATATAGGACACAAGAG
ATGAAGCAGAAAAGTTGGAAAAGTTGTAAAAACAGTCACCCCCCAAAAAAAGTTATCCCCAGTAAATAAAGAAAATTAAAGACAAACTCTAGAAATACA
ACTCATACTGAACGTTATCCTCAAGACGTAAAGTTATCCCCAGTCAATCTAGAAAATTGAAAGAAGAAAATTAAGATTTCTAATT
AAATTTTTGTGTATGGGTGTTTGTCTTATATGTCTGTAGAGGCCAGAAGAAGACACTGGGTCCTCTGGAACGGGAGCCTGCAGATGGTTGAGAGC
CGTCATACGGTGCTGACAGGTAACCCGGTCCTATCTAGAAAATATAACACACATTTATACATAAAAGACTAGGCTCATATGTCAGCTAAATACATGTTTCCACTCAAAATC
CTAATTTTAATATTTTTGTATCTAGAAATAACACAACCTAAGCTGGGACCCTGCAGCAGTCTCAGCAGTCTCGAGCCATGTGGCCATGTGGCTCACACTGTCACCCAGCAGGGTAT
ACCAAGTAAGACATTTCTCAAGAAAGAAGGGCACAACCTAAGCTGGGACCCTGCAGCAGTCTCAGCAGTCTCGAGCCATGTGGCTCACACTGTCACCCAGCAGGGTAT
TTCTGGCGGTGCTACACCTGCTACTTAAAGGAGGCCAGGCAGGCCAGGATCCAAGATCCAAACTTCAGATC

WXRE ID: B (SEQ ID NO: 48)

TCCACACTCATGTTGACATTAAAGCCATCGACAATCTCAGTAAGTACTAGTAACAAGTAACAAATAAGACTGATCCATCACACAACATTACCCTGGC
TGTGTCTTTGGAGTAAAATCATGTAGATCAAGGTATGGTATGCTTGAACACCAAAAAGTAACCACAGAGTAGAGTCCAGTGAGTCCCTT
ATGCGGTGAGCCCACTTCCCTTTTGCGTTGTTTGTTTTTTACTTAATGTCTGGCAGAATTCAGGCATGTAGTCAGGCCCACCTTGCAGGAGTCCGTTCTC
TCTTTCCACAACTGGATCCCAGGGACACAGGAGGTCTTGGGCTTGGCAGCGGGTGCCCTTACCTGTACAGCCCTCACTGAGCACTGGTTTTA
CTGAAAGCTAACTCTGAAGACTGGAATTCGATACTTTTTTAGGGTGATGAGTCACTCACTGTTAGGTAACATGTTGGAGACTTACCAACATCAAAAACTGTGTTTAAAGT
ACAAACCAGGCAGCCGGAGACTCACTGCTTACCACGCAAACTGCTGTGTAACCAAACTGCTGTGTGATTCTTTAACCTATGTCTTTAACCTATGTCCTTTTGGAGACTTAAAGT
TACTTGCAACCTTTCTGTAACCACCGCAAACTGCTGTGTGATTCTTTAACCTATGTCTTTAACCTATGTCCTGTTCCGGGTAATTGCACATT
TCTAATTAAAGCTTTCAAAGTGGGCCAGGTTCTCTGGAGCTGAAATGTTCGTTGAAGGGGCAAGTTATTTCTCTAACATCATGAGGGAACTGGGT
CAGGGTGTGGGACTGCACCCTGCTGAGGGGATGGTATAGGAAGCCCAAAGCTGAATGACCCAAAGCTGAATGACCTCCTTGGCCTGTGTTCCTTTTGGCCTGTGTTCCCCACGAACCCAGA
TCTGTTTGCATGCAAGTGAGCTCATTGCTGTGGAAGCTAACAGCTAGCCAGGATCCTTGGGATCCTTTCTCAGCCTTCCAAGTGCTGAAATTGCAGTGACTACACTACTAAGCCCGTAGG
GCTCTCTCTAACAGCTAACACTAGCCTAGCCAGCTGCCCTTGGCCAGCTGCCCTTGGGATCCTTTCTCAGCCTTCCAAGTGCTGAAATTGCAGTGACTACACTACTAAGCCCGTAGG
CCTTTGTGTGGGTTCTGCAGATCCAGATCCAAAACTTCAGATC

WXRE ID: C (SEQ ID NO: 49)

TCTTCTTCTTCTTCAAAGATGTCAAATATCCACACCTTCAAACAAGTTAAGTTAGAGAATCCTATGATAGAAAATGAAGAGAGTGGTTTCTAATGTGA
ATATTATGCAATGAGCTCATAGCTGGCTCTCTTACTTCAACTTGTGAACAGCATCATGATTGAGATACAGGGGTGGGGTAAGCAAAGCCTACAAGACAGT
AGGTGTGGTCTGGATTCACATGCAGAAGGGAGGATCCCCTCACTTTGGTCTGGACAGCAGTGGTAACCCTGCTGCTCACATGAGCAGCCTGTTTAGCTGCCATCTCCCCC
CTCCTTGGCAGTTTCACACTGGGTGAGTCATGCTGGCCTTAGAGCCTTAGAGCCGAAGTGAGTTTTTAGAGCCTAAAATTGTTTCACTTACCAGCATGGGAAATCTAACACACAGCACAA
TGGCCAGGTCACAGAGCTGAAATCATCTCAACAACCGCTATTAATCTGTCTTCTGTCTTCCTGATGAAAAAAAAGAGACCACCCAAATAGTTTATATCCATAGTCTCCC
CATTTCCTCAACCTGACATGTCTAGAATCAACAGTATACCTTCGTCGTTCCTTCCTGATGAAAAAAAAGAGACCACCCAAATAGTTTATATCCATAGTCTCCC
TACAAAAGACCGCGCCAGAGAAAACAGGAGGGTTCAAGCAACAGGAGTACTGCAGGGCTGATCCATAGTCCTATTCAAACTTAGT
```

*WXRE ID: D (SEQ ID NO: 50)*

FIG. 7 (Continued)

TCTTTATGCTAAATAAAAAAACAGACTTGGTCTGAGATGTGCTGACACCTGGTCGCTAAAGAACACAGGTAACTAGAATTTGAATCTAAGGTATGGTTACCAAA
TTGGTGAAAAATTCAGCAAGAAAAGAGTGTTTGCTTTGTATGAAGGAACTCATGTTCACCTTTTGGTTAAGGTATATGAGAGTGGTGAGAAATAAACT
TGTGGGTGTTCAGTATTAACTGGATCTGCCCTCCTGATTTTATTCTGTGTCTTTCTAGGCTTCCTTAGTCCACACTCTCCCTTTCAAGAACAAACCTC
AGGCTGCTTGGTTGGCTGCCAGCTCCAGCTCCAAAAAGTCAGCTTCTTCCACATTGCACAAGCATGTGAACTTCATAAATCTGCTTAGCTTCC
AATGTTTAAATCCAGTGAGGTCTACTTGATTATTTACAGGCTGATAATCCATTCAGAATAATGAAAACTAGTAGTGATGGATCTTCCTGAGGTGCA
AATAATCCCAAAGCAAATGCCAAAGTGCCTGCAAGGTAGGAATGAACTTTATTTCCAAACTGACAGCAGCAGCTGCTGTGGTGGAAGCGGTGCACAC
ACTGTATAAACTTGAGAGTGGGCAGCTACACAGATC
GATCAAGTGTTGTTGGCAGCTACACAGATC

*WXRE ID: E (SEQ ID NO: 51)*

ATGGTCAGACCCAGGTGCTCTGGCACGACAGGTTTCAGTCCCTCCCATGAGGTGTCCCATGTATGCTCAGTGAGATGTCCTTCACCTCTGACACCTCAG
ATACCTCACCGGGTTCTCTTTGCAGCGAGAAATAGATGCTAACAAATTCTGTTGATGAATCCATCTGGGCAATAAGACTCAAGGGAGCCACTTGCCTA
CACACCTGAATAGATGAAGCAAGCCCTACCCTCCAGGTATCTAAAAACCAGGATTCCAATAATAAAATCCTTACAATTCACAGGGGAGCCTGAA
TGTTTTGATTTACAATGTGGCATTGATTGTGTTGGAGAATATGGGGGAACAACTAGTGCACCTTGAAAACATCACTGCTCAATTGCAGCATTGCCAAA
ATACCCCAGCAGCAGAACGCATTAGGACAGAGTGTCTGTGATGCTAGCAGTCCCTGGGACAGGTCCATAGTGCACATACAAAAATCTGTCCTTTCTGCCCCCTGCACGGGACAAGGGCCAGTTGT
TGAAGGACAGAGAGGCCCAGTGTATGCTGCTAGCGTAAAGCTTCTGCACAACAAAAATCTGTCCTTTCTGCCCCCTGCACGGGACAAGGGCCAGTTGT
AGAGAGTGCTTGTGTCACAGGGCTCCTCTAGGCCTCTGTCTCTGTCTCTGTAGCCATTTCTTCAAATTGGTTAAATAGTAGAAAACGCTGAGTGAGTGGCTGGGGAGGTCCTGGTCTTTTACA
TGTTTGAGACAAGAATTAAGGAGCCAACTCTATAGGGACTTCTTACCTGTACCTGTCTCCCAGCCTTATACTCCTGAACCTTCCTGATC
AATCCTCTATATGAATAAGCCTAAATACTGCCTCCCTCCAGCCTTATACTCCTGAACCTTCCTGATC
TCAGACTGGTTGAATTCGTGTACCTCAGTGTGGCCTTGAACTCCTGATC

*WXRE ID: F (SEQ ID NO: 52)*

CTTCTGCAGTAGTATTGCATTGAGACAGCACTGGATACTGGAAAATCTTGGGGATACTGGAAAATCTGAGTGTCTCTCCCCTAAAGCTAAGATTGAAAC
TAAAATCTCCAATGTCTTGTGCTAATAGTATTTGGGGTGTGGGGTTTAGAAATGTCTTTAGAATTACATGGAAGAACACTTGTGATG
GAATTGGCGGCCTTAAATGATGAAAACCATAGACCAGCCTGGAACACTTGTCCTGTCCTTTGTAACATTCTTGTCATGTGCTCCTGATTTCT
TATGATACTGCCAGAAAGGCATTTGACAGCTTTGGGAACTTCCCAGTTCCAGGAGAAATAATTATAGATTATCAGTGGCCAAGATACTGATAGAAGCATCAAGGA
TCTCCCAGCTTATAGCATTTTGTTTGTGAAAACAAATAGTCTTAGAGAAATAATTATAGATTATCAGTGGCCAAGATACTGATAGAAGCATCAAGGA
TTATTTTAAAATGCCAGGCCAGGGAGATGGTTCAGAGGGTTAAGAGGCTTGCTGCCACATGTAACCAGTACGTAGTGAGTAAAA
GTGGAAGGATAGAAATGCCGCTATTTTTTATPATAAATAAACATAAGGACACAGCACGCGGAGCACACACATACACACACACACAAAAAAAA
GTTAGAGTCAATGCGCTATTTTTTATPATAAATAAACATAAGGACACAGCACGCGGAGCACACACATACACACACACACAAAAAAAA
AAAAAAAAATGAAAGTGAAAGTAGAAGAGAGGGCCCGCTGCTTAGGAAGAGAGGGTCCCAGCTGGTTAGGAAGGGTATTAAAGGGTGAAAAATGACC
CAAATTCACTATGATACTTACATGAATTCGTGTCAAATCATTTAAAAAGCCATGTATTAGTTTCTTGTGTATTGTTTGTGATAAAATGCCATGA

FIG. 7 (Continued)

ACTAAAGCAACTTTAAAAAGTTTATTTTGTTTTTCAGTTCCAGAGGTTCCTGAGGGGCATTCATAATGGTGGGAGAGGCATGTCAGCTGGTAGCCAA
AGCAGGAAGCTGAGGGCCTAGAGAGATGGCTCACTAGTTAAGAGACCACTGACTCCCTCTTCCAGAGGACTCAGTTCAGTTCCAGCCCCACATGGCAGC
TCACACCTGTCTGTGTAGCTCCAGTTTCAGGGGACGCAACACCCATGGCAAAACATTGATTAACATAAATATAAAAATGAAAAACCTCCAGTTTCAGGGTAT
CCGACACCCACGACAAAAAACATCAATGGGTATAAAAAATAAAATAAAATACTTTTAAAAAGCAGGAAGCTGAGAGATC

*WXRE ID: G (SEQ ID NO: 53)*

CTTGGTACCTTCTTTTCCCAGAGTCTATACAAGTTAGGAAAAAAACAGGAGAGACAGCTGAAGCTCAGCATCTGGCAAGACCCAAC
AGGGTCCCTCTGCTAATGATGTTCCCTGAGATTTGATTCTTAAGACCTCAAGTCATGAGGTGACATCCTCACCTCAGACTTCTAAATCAC
CTGTGTTCTCCTTTCTACAAATGGGACAAACATCCAATCCAACATTCAAGTCCAAAACCTGAGAGTCATCCTTAATTTCTCTTTTCCTTTTAGCTCCC
TACCGATTCTTTTTTCAAAAATCCACCCTTTCTCTCAATCTTCAATCTTCACGTCAGTGTTTTAGAAAATAGGTCATTCTCTCTCCTGGGAACTCCTGTCCTGGG
CATGAATCGGCAAATCTCATTTTAAAAAATCACATGTAGAGCTTGGCCCCTGCCTTGACATCAGAGCTCAAGCAACCTCAGAGTATCAGACCCCTCTTGCATCCCACCAAAGAGAACCCTTGGACCCCATACACACCAGGAGA
GGAAGAGACGGGCACCTGAACCCCACTGGAAGAATGGGAAGAACACCCAACACAGATGAAGCAGAGAATGACTTCTGTACTTGAAGTTCTATCTGGGCAATA
TGACAACAAAGGAGAAACAAGGGGATACAAATTGGAAAAGGCAAGTCAAATTTTTACTGTTTGCAGATGATAGTTACATAAGTAACCCAAA
AAACTCTACCAGGGAACTACTACAGCTGATAAACACCTTCAGCTAAGTGGAGGATACAAGATTAAACTCAAAAAAATCACTAGCCTATTATACACAGG
AGATAAATGGGCTGAGAAATAAATCAGAGAAATAAAGAAATAAAGAAGAAATTAAAGAAGATACCAGAAAAATGGGGTAATGATAACCAAACAAGTGAAA
GACCTGTCTAGCAAGAACTTTGAGTCTTTAAAAGAAAGAAATTAAAAGAAAGATGGAAAGATC

*WXRE ID: H (SEQ ID NO: 54)*

GATCTTCTGTGAGTTCGGAGGCCAGCCTGGTCTCTAGAGCGGAGTGCCAGGATAGGTTCCAAAGCTTCCAAGAGAGAAACCCTGTCTCTCGAAAAAACCAAAAAAAAAA
GAAAAGGAAAAGAAAGAATTTAGTGAAAAGCAACATTGTGAAAAAGCAACATTGTGCATTATGTTATGTGTTTTACATGAGTGAGTTTTACACTCAT
GTAAAGGTCAGAGGAAATCTCTTCTTTTTCCTTCCAACTCGTATCCACTAGTCTTATAGGCAACCTTGGTCTTTTAA
GGTGTGTGTCCCTGTGTCTGTCCTTCCTTCGTAGTTTGATAGTGTTTCCAAAGCTTCTTCCTAAAGCAGGACAAATTGGCTGAGCCTGAAATCCGATAATGC
GTGTGGAGGGGGGCGGGGCAATAGTAGGTGTGTGGAAAAGAGAGTGTCTTGTGCCTCTTTATTAGAGCTTAAAATTAAATAATAAGTGCTACAAGAGTCTTTACATTCTTTGATCACATCT
GTCAGTTCCTCTCTGAACACTAAGACTAAGACTAAGAGGCAAGTTTTTTTGGTACTAAATTAAATAATAAGTGGTGTAAAATGTCTGCCTTTTCAATGATACATGGCAGTG
ACCCAGAGACATTGCCGAGTTTAGAACTAGGCAAGTCTTCTGCTCGGCCAGTTCACACATTGCACTGGCAGTTCACATTCAACAGTACCTGTTCTGTACTGGCATTCGGGTTTAAG
AGAGTAGGTGCCTGATCCTGGAGTCTGTATTCTCTGTGTTCTCACCACTGAACGTTCTGTTCTATTAAAGAACATCAACGATGCTTGGGTTTGCACCGATGTTCAGGC
CATACAGGCCGATGAAGATCCCATCATGGGTTTCCACCCTCGTTCCAGAATCCTCCCCCTCCTCCACCGGTTGTTGTGCATGATGTTTGGATGCTAGACTAG
CCAAATATCATACACAAATGAGCAGGGCCGAGGTGGGAGTAGGTGCAGTGCGCTTCGCTTCCAATACTATCTCACTCCTCCAGATGCT
TTGCATCTGACAAGAACTTTGTGTGTTTGTACCAGCGCATGCCCTTGGTACCAGGACTTTAAGTAAATGCAAAAGATTGTCGGTTTTGTTTTGTTTTCATTTTG

FIG. 7 (Continued)

```
TTTTTTAATTCTACTGACAAGTTGCTCTAGTAACCCAAAGAAGAAGTGAAGGAGAAAGCAGCTGCCTCACCGCGCCAGATATTGATTTGGTTCAGATGTTTCAA
TGCCTCAATGATGACAATAAAACCACAAAAATTTTCTTAACAGTTTAATTGTTTAATTAGTTAAATAGCTCTTTGGGCATCAACAGTTCTGACCAATT
GTCTCTCATTTCACCCTCCCATCTCTGCCTCATGTTAACAATACCTGCTGCAAGGAGCAAATTGACTGACAGTTAACAGTCCCAACCAAGTTCTTTCA
AGCCTGCTAGGCCAGAGTTCTCTCCAACCCACTTGGTCTCTTTGGAAAGCCTGGAAGCAGGTCTGGCCTGAAGCTTATCTTGTACTGAAGAC
TCTAAAGTGAGTTCTGTCTGACACCCTCCTGTAGCCTCTGCCTCTGAGTCTCAGTAGCCAGGATAGATGATTCTGTAGCTGCTAGAAAGACCTTGATAAATA
TGGTTTCCCATGTTTAGATTCTATGGGTTGAAGTCCCGGACGCCCGGATGGACCTGCTCTATTCCCAAAAGGGTCAGGATCACATTCAGAGTGCCCACATTCCCGA
GCAAAGCAAGAAGATGTTGTACTGC
```

*WXRE ID: I (SEQ ID NO: 55)*

```
GATCTCCACACTCCATGTTGACATTAAAGCCATGCAACAATCTCAGTAAGTACTAGTAAACAAGTAACAAATAAGACTGATCCATCACACAACATTACCC
TGGCTGTGTCTTTGGAGTAAAAATCATGTAGATCAAGGTATGCTTAGCTTGAACACCACAAAAGTAACCACAGAGTAGAAGAGTAGAGTCCAGTGAGTG
CCTTATGCGTGAGCCCACTTCCCTTTTGCGTTGTTTTACTTAATGTCTGGCAGAATTCAGGCATGTAGGTCAGGAGGCCACCTTGCGAGGAGTCCGT
TCTTCTTTCCACCAACTGGATCCCAGGGACAGGACACAGGTCTTGGGCTTGGCAGCGGGTGCCCTTACCTACTGAGCCATTTCACCCACTGACTTGGT
TTTACTGAAAGCTAACTCTGAAGACTGGAATTCGATACTTTTTTAGGGTGATGAGTCACTCACTGTACAGCCTCAGCACTAGTTGCTGAAGTACATTAC
CCTCACAAACCAGGCAGCCGGAGACTCACTGCTTACATGTAATCGAGGCCATGCTATGTTAGGTAACATGTTGGAGACTTACCAAAAACTGTGTTTTA
AAGTTACTTGCAACCTTCTGTAACCACCGCAAACTGTTCTCTTGGGACTGCTGAGGGATGGCAGGTTCATTTGCCTTGTTCCTTTGTTGTTGCATGTGTTTG
ATTTCTAATTAAAGCTTTCAAGTGGGGACTGCACCCTGCTGAGGGGATGGTATAGGAAGCCCAAAGCTGATGTCACTTTATTTCTCTAACATCATGAGGGAACT
GGGTCAGGGTGTGGGACTGGCATGCAAGTGAGCTCATTTGCTGAGCTCAGCCTAGCACTAGCCTAGCCAGCTGCCTCTCTATTGCTTCGATTTCCCTGGGATCCTGCCCCGAACC
CATTTCTGTTTGCATGCAAGTGAGCTCATTTGCTGAGCTCAGCCTAACACTAGCCTAGCCAGCTGCCTCTCTATTGCTTCGATTTCCCTGGGATCCTGCCCCGAACC
CAGAGCCTCTCAGCTAACACTAGCCTAGCACTAGCCTAGCCAGCTGCCTCTCTATTGCTTCCAAGTGGCTGAAATTGCAGGTACACTACTAAGCCCCG
TAGGCCCTTTGTTGGGTTCTGCAGATCCAGATC
```

*WXRE ID: J (SEQ ID NO: 56)*

```
GATCACTTCTAAGCAATTCTGAGATAAGAATGGACATTCAACACCATTAGACATGTGCGGCTTTTGGACAGTCAACCAGTTAGTTATTCTTAAAAGT
GTTAAATATTAGGCCTGCTTCTTCCCTATGACCTTTATTTTCGACCTTTATTTTCCTGGGTTTTGCTTCTCGGGTTTGCTTTCTCGGGTTTGCTTCTCGGGTTATTCTTCCAGGTACTAGGAGAGGTTGGT
ATCGGGTAGGTGCACTCATGAGAAGAGAGGCCCTGAGGAGTATGAGAAGCTACACAGTAAAAATTCCAAGGAGAAAATGAAGGAATGAAGAAACTATAGAAACAGGCAAGGGCA
AACAAAAACCCAAAACAAACAAACAAACAAAGCAACTTTACTAAAATTCCAAGGGAAAGCATAGAAACAGGCCAAGGAATGAAGAAACTATAGACACAGGCAAGGGCA
TACCTATTCTTATAGGCAGTGGTTAGGCCACTAGTGTTAGGCCCACTAGTTGCAGTGTTGCAGTCCCACTGGTAGCGTTGCAGTGTTGCAGTCAACTATGCTCCTC
TGGTCCTGCCACCCACTCAGTAAGTTCTCAGCCAGGGAAAGTCAGGCCTGAGGCAACAAGGAAAGCAAAGGGTTGGCTTACCCTTAGGATGAAGAATGGTCAGTAAGTGCT
CAATGCACACAGGTGCTTCCCTTCCCTTCTTCTTGGCTTTTCTTCAGTCAGGTTACAGATTGGTCAAGGAAATCTCTTAGGGTCCATTTCCCAGCCCTGGC
TCCTCCCCAAAGTGGCTTCCCTTCTTTGGTTCTCAGGTTCTGACCTTGCATGGAGTCCAGGCAGGGCATGGGTCTATGTGGGCTTCAAC
TTCTGTGCCCCAAAGTTGCCTTCACTGTCTGACCTTGCATGGAGTCCAGGCAGGCAGGGCATGGGTCTTATGTGGGCTTCAAC
GTTCCCCAAAGATTGCATGAAGCCTCTAAACTCTCAGTCTTGTTCTCCAAAGCTTTTATGCGTAGACAGTAGTCTTGGGAGCTGTGAGGGACTTACCTAG
```

FIG. 7 (Continued)

```
ACATATCCCTGAGAAACCAGGCTGCAGGCAGAGGAGGAACATTGTGGCAGCTTAGTCAGAGGGATGGGAGGACATGCCATTGTCATCACTAAGGAGATGT
AGACCAGTTGACCAGCCCAGTAAGGCCTGGGTTTCCAAACTTCAGGAGCTTTGCCTGAATTTCAGGTATGAAAGTTTGCCACACTGAAAGGCCATAC
AGGTGGAAAAGTCCATCCAAAACTCTGCCTTGGTGGGAGGATATCAATGAACTATTGGATGCTTGCTGGAGCATGAAATATCCTGAAATGGCCATTGGT
CCAGGGTAAGACAGGTCTCAATTCTCCCAGAGCCCCCACAGTACTTAAGGAAACCTGGCTTAGCTGACGTCCCCTGCCTTGTGATATGTA
AGTTCCTACCATCTCATCTTTGACTCGGATGGGGCTGTGGATAGGGGACAACCTTGCTGAAGAAGACCAGAAAGACCTTCTCCTTCCTTCCTCTCTCC
AGCTGCTCATAGAAGCAGCGACCTTCTGAGTCCACAAAGATC
```

*WXRE ID: K (SEQ ID NO: 57)*

```
GATCCAGCTATTAGAATGGTGCTTGCATTTAAAGGGTAACCAGGGAATATTAGGCTCCTAAAAATCAAGTAGTCCAAAACATGTCATGCAACCTGACAC
TTTGGTTATTTATGAATTAAAGATATTTGAGAAAATGGACAAATAGGACCAATTCTCTAATTTTTGGGAGAGTGTGACAGCAGAATCCATCCTTTCATTAGGAAA
ACAATGATTCTACTAATTGGTAGAGACCAAGAAAGGCATGAAAATCCTAAAAGTTGTTCATCCTTAAGCCTTAAGCCTTCATCGTTTTTCTCA
CAACTTGTCACTTTTTAAAGTCTACATCTAATATCTAATAATTGCTTTCATTCATCAGTTCTTTAAGTATTTGTTTATCTGTCTTTGGGTGGCACT
GACAAAATTGCACTAAATAAATATTGTACTTTTTCCATGTTAATGTGATTTATGCTACTTTAATCTCTGACAAAACCAAAATGAAAACCCTATTAAAGG
GGAGTTGGTCAAATCTACCCTTTTTCATCAAGAATGGGTACAGAACTACAATGGTGAAAGATGAATCCTGTAAATCTACAGTGACTACAGCCAGT
ATATTTCAAATAATTCCTACAGTAATCAACAAAATTAAATTTGTATCCTATTTTATGTATCCTATTTAAAAATAAAAAATTTATAAAATAACAAGTC
GAATATTTTGTCACTTAGAGATTGTGAAGAAACCAATTTAAAATAAAAGATTAGCAGAAAAATAAATTTATTAACTAATATCTATTTTTCAATATGTTTGAATT
TCTGAATTTATTGTATTTTCCAAAACATGGGTAAAGATTAGAAAACATGTGTTGTTGCAATGGCTAAAACAGGCCAATTTACTTTCTAGCTTTCAAT
GGCATCAAAAGTTCTTTTTTACTCTAGGAAATGCTGCAACTAAAACAGCATTTGCTGGCCCCACTGAAGACTTCTTACACGTAGCCCTCCAGGCTGGG
GACACATGCCGCTTATGTGCAAGGG
```

*WXRE ID: L (SEQ ID NO: 58)*

```
CCACACTCATGTTGACATTAAAGCCATCGACAAATCTCAGTAAGTACTAGTAAACAAGTAACAAATAAGACTGATCCATCACACAACATTACCCTGGCT
GTGTCTTTGGAGTAAAAATCATGTAGATCAAGGTATGGTATGCTTGAACACCAAAAAGTAACACAGAGTAGGAGAGTCAGTGAGTGCCTTA
TGCGTGAGCCCACTTCCCTTTTTGCGTTTGTTTTTTACTTAAATGTCTGGCAGAATTCAGGCATGTAGGTCAGGATCAGAGGAGTCCGTTCTCT
CTTTCCACCAACTGGATCCCCAGGGACAGGACACACAGGTCTTGGGCGGTGCCCTTACCTACTGACCCCATTTCACCACTGAAGTACATTACCCTCA
TGAAAGCTAACTCTGAAGACTGGAATTCGATACTTTTTTAGGGTGATGAGTCACTGTACAGCCTATGTTGGAGTAACATGTTGGAGACTTACCAAAAAACTGTGTTTTAAAGTT
CAAACCAGGCAGCCGGAGACTCACTGCTTACACCGCAAACTGCTGCTTACCAAAACTGTGTTTTAAAGTTACTTGCAACCTTCTGTAACCACGCAAACTTCT
TAATTAAAGCTTTGCAAAGTGGGCCAGGTTCTCTTGGAGCTGAAATGTTCGTTGAAGTGGTATAGGAAGTGTTATTTCTCTAACATCATGAGGGAACTGGGTC
AGGGTGTGGGGACTGCACCCTGCGAGGGGATGGTGGGAAGCCCAAAGCCCACCCTTTGGCCTTGGTTCCTTTTGTTTGCTTTGTGTTTGTGCATTT
CTGTTTGCCAAGTGCAAGTGAGCTCATTTGCTGTGGGAAGCCCAAGCTGATGTCACTCTCTATTATTCACTGAAGCTAATGTCTGAACCCAGAG
```

FIG. 7 (Continued)

CTCTCAGCTAACACTAGCCTAGCTAGCCAGCTGCCCTTGGGATCCTTTCTCAGCCTTCCAAGTGCTGAAATTGCAGGTACACTACTAAGCCCGTAGGC
CTTTGTGTGGGTTCTGCAGATCCAAACTTC

*Human CMV promoter (SEQ ID NO: 59)*

GTTGACATTGATTATTGACTAGTTATTAATAGTAAATCAATTACGGGGTCATTAGTTCATAGCCCATATATGGAGTTCCGC
GTTACATAACTTACGGTAAATGGCCCGCCTGGCTGACCGCCCAACGACCCCGCCATTGACGTCAATAATGACGTATG
TCCCATAGTAAACGCCAATAGGGACTTTCCATTGACGTCAATGGGTGGAGTATTTACGGTAAACTGCCCACTTGGCAGT
ACATCAAGTGTATCATATGCCAAGTACGCCCCCTATTGACGTCAATGACGGTAAATGGCCCGCCTGGCATTATGCCCAG
TACATGACCTTATGGGACTTTCCTACTTGGCAGTACATCTACGTATTAGTCATCGCTATTACCATGGTGATGCGGTTTTG
GCAGTACATCAATGGGCGTGGATAGCGGTTTGACTCACGGGGATTTCCAAGTCTCCACCCCATTGACGTCAATGGGAGT
TTGTTTTGGCACCAAAATCAACGGGACTTTCCAAAATGTCGTAACAACTCCGCCCCATTGACGCAAATGGGCGGTAGGC
GTGTACGGTGGGAGGTCTATATAAGCAGAGCTCGTTTAGTGAACCGTCAGATCGCCTGGAGACGCCATCCACGCTGTT
TGACCTCCATAGAAGACACCGGGACCGATCCAGCCTCCGACTCTA

*Human EF-1α gene intron 1 (SEQ ID NO: 34)*

GTAAGTGCCGTGTGTGGTTCCCGCGCGGCCTGCCTGCCTCTTTACGGGTTATGGCCCTTGCCGTGCCTTGAATTACTTCCACGCC
CCTGGCTGCAGTACGTGATTCTTGATCCCGAGCTTCGGGTTGGAAGTGGGTGGGAGAGTTCGAGGCCTTGCGCTTAAGG
AGCCCCTTCGCCTGCCTGCGCTTGAGGTTGAGGCGCCTGGGGCGCCTGGGCGTGCGAATCTGGTGGCACCTTCGC
GCCTGTCTCGCTGCTTTCGATAAGTCTCTAGCCATTAAAATTTTGATGACCTGCTGCGACGCTTTTTTCTGGCAAGAT
AGTCTTGTAAATGCGGGCCAAGATCTGCACACTGGTATTTCGGTTTTTGGGGCCGAGGCCACCGAGAATCGGACGGGGGTCCGTGGCGT
CCCAGCGCACATGTTCGGCGAGGCCTCGCGCCGCGTGTATCGCCCCGCGCCCTGCCAGGGAGCTCAAAATGGAGGACGCGGCGCTCGGGAGAGC
GGCCTGCTCGTCGGTGCCTGGCCTCGCGCCGCCAGT
GGGCGGGGGGTGAGTGCAGTCACCACACAAAGGAAAAGGGCCTTTCCGTCCGTCTCCAGCCGTCTCATGTGACTCCCACGGAGTACC
GGGCGCCGTCCAGCCACCTCGATTAGTTCTCGAGTACGTCGTCTTTAGGTTGGGGGGAGGGGTTTATGC
GATGGAGTTTCCCCACACTGAGTGGGTGGAGACTGAAGTTAGGCCAGCTTGGCACTGATTGAATTCTCCTTGGAATTT
GCCCTTTTTGAGTTTGGATCTTGGTTCATTCTCAAGCCTCAGACAGTGGTTCAAAGTTTTTTTCTTCCATTTCAG

FIG. 8

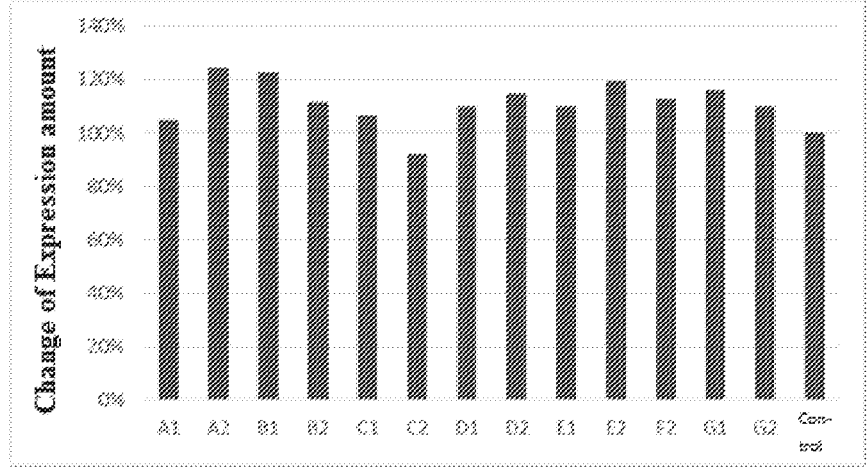
Fig. 11

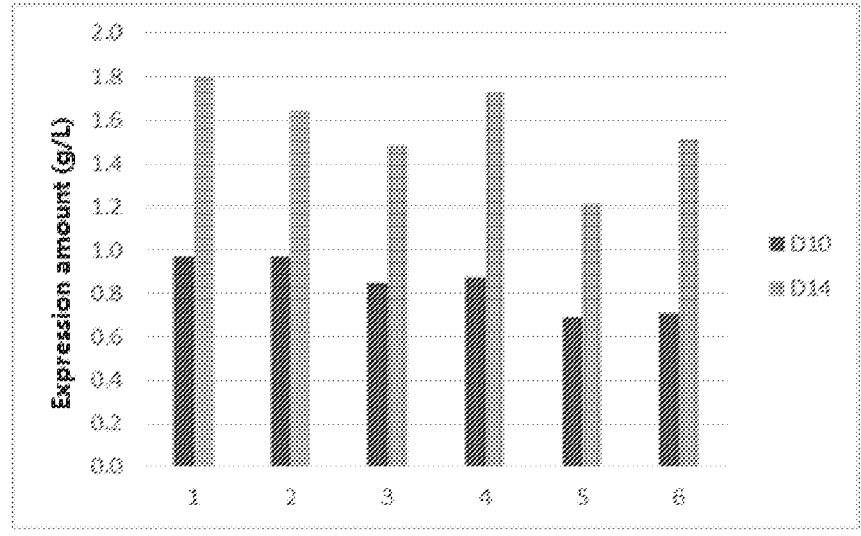
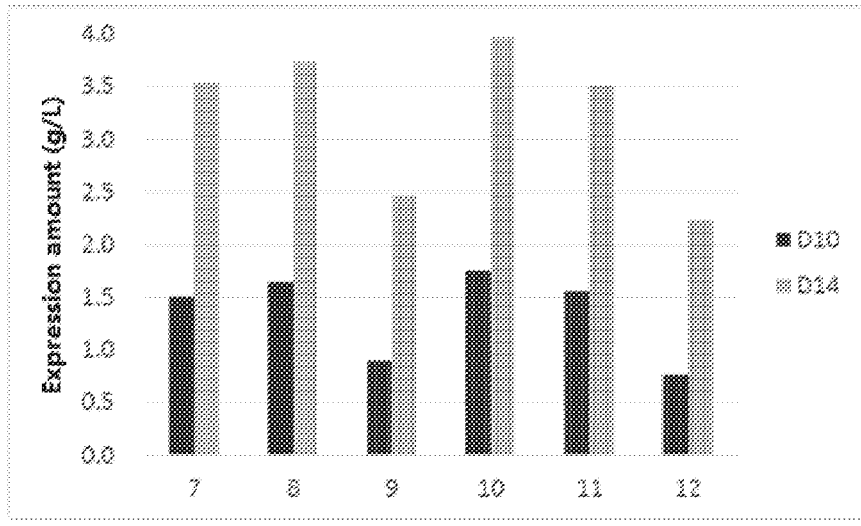
Fig. 15

(1) Amino acid sequence of the A chain of PD-L1 (SEQ ID NO: 71)

FTVTVPKDLYVVEYGSNMTIECKFPVEKQLDLAALIVYWEMEDKNIIQFVHGEEDLKVQHSSYRQRARLLKDQLSLGNAAL
QTDVKLQDAGVYRCMISYGGADYKRITVKVNAPYNKINQRILVVDPVTSEHELTCQAEGYPKAEVIWTSSDHQVLSGKTTT
TNSKREEKLFNVTSTLRINTTNEIFYCTFRRLDPEENHTAELVIPELPLAHPPNERTPRDCGKPCICTVPEVSSVFIFPPKPKD
VLTITLTPKVTCVVVDISKDDPEVQFSWFVDDVEVHTAQTQPREEQFNSTFRSVSELPIMHQDWLNGKEFKCRVNSAAFPAPI
EKTISKTKGRPKAPQVYTIPPPKEQMAKDKVSLTCMITDFFPEDITVEWQWNGQPAENYKNTQPIMDTDGSYFVYSKLNVQK
SNWEAGNTFTCSVLHEGLHNHHTEKSLSHSPGK (2) Amino acid sequence of the heavy chain (HC) of Adalimumab (SEQ ID NO: 72)

EVQLVESGGGLVQPGRSLRLSCAASGFTFDDYAMHWVRQAPGKGLEWVSAITWNSGHIDYADSVEGRFTISRDNAKNSLYL
QMNSLRAEDTAVYYCAKVSYLSTASSLDYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK (3) Amino acid sequence of the light chain (LC) of Adalimumab (SEQ ID NO: 73)

DIQMTQSPSSLSASVGDRVTITCRASQGIRNYLAWYQQKPGKAPKLLIYAASTLQSGVPSRFSGSGSGTDFTLTISSLQPEDVA
TYYCQRYNRAPYTFGQGTKVEIKRTVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

Fig. 16

ENHANCED EXPRESSION SYSTEM AND METHODS OF USE THEREOF

CROSS-REFERENCE TO RELATED APPLICATIONS

This application is a National Stage Application under 35 U.S.C. § 371 and claims the benefit of International Application No. PCT/CN2021/076719, filed Feb. 18, 2021, which claims priority under 35 U.S.C. § 365(b) to International Application No. PCT/CN2020/081464, filed Mar. 26, 2020 and CN202010102211.1, filed on Feb. 19, 2020. The disclosure of the foregoing is incorporated herein by reference.

TECHNICAL FIELD

This disclosure relates to an efficient protein expression system that utilizes piggyBac transposons and/or regulatory elements.

BACKGROUND

Many expression systems for recombinant proteins are available and include e.g., bacteria, yeast, fungi, insect, plant and mammalian cells. The protein expression systems differ significantly and may affect both the product formation and subsequent isolation/purification of the protein. Expression systems such as bacteria are incapable of producing specific classes of proteins, which require post-translational modifications such as glycosylation for bioactivity. Furthermore, many therapeutic proteins require complex post-translational modifications such as glycosylation in order to be biologically active.

Mammalian expression systems for producing therapeutic recombinant proteins are commonly used by pharmaceutical companies. Mammalian cells have the ability to carry out proper protein folding and complex post-translational modifications, which are necessary for the therapeutic activity of many proteins. Many mammalian cell expression systems have been approved for use in the production of therapeutic proteins. However, creating a stable mammalian cell expression system for therapeutic recombinant proteins is time-consuming, and the expression level is often not optimized, thus is not ideal for large-scale production.

As such, there is a need for an improved expression system, which can be used as a flexible platform to generate stable cell lines that can express various therapeutic recombinant proteins at an increased level. The ability to produce stable cell lines for expressing recombinant proteins in the same host cells that would likely be used in the manufacturing process in a timely manner would be particularly useful during early stage drug development. There is also a need for an expression system having enhanced transcription and translation efficiencies.

SUMMARY

This disclosure relates to an efficient protein expression system that utilizes piggyBac transposons and/or regulatory elements. This expression system provides a versatile tool that can efficiently integrate a nucleic acid of interest into the genome of a cell and can dramatically increase protein expression in the cell (e.g., Chinese Hamster Ovary cells). In one aspect, the expression system can efficiently move the vector sequence (e.g., a sequence between the two piggyBac ITRs) in the transposon vector into a target genome. The system can be used to create stable cell lines for expressing various proteins (e.g., antibody heavy chains and light chains). In one aspect, the piggyBac expression systems can be used with Chinese Hamster Ovary (CHO) cells to produce recombinant proteins for both research and biopharmaceutical manufacturing purposes.

In one aspect, provided herein is a nucleic acid comprising a 5'-ITR (inverted terminal repeat) sequence; a 3'-ITR sequence; and a regulatory element sequence that is at least 80%, 85%, 90%, 95% or 100% identical to a sequence selected from the group consisting of SEQ ID NOs: 1-30 and SEQ ID NOs: 35-58.

In some embodiments, the 5' ITR sequence comprises or consists of a sequence that is at least 80%, 85%, 90%, 95% or 100% identical to SEQ ID NO: 68, and the 3' ITR sequence comprises or consists of a sequence that is at least 80%, 85%, 90%, 95% or 100% identical to SEQ ID NO: 60.

In some embodiments, the 5' ITR sequence comprises SEQ ID NO: 68 and the 3' ITR sequence comprises SEQ ID NO: 60.

In some embodiments, the nucleic acid as described herein, further comprising a 5'-internal domain and a 3'-internal domain. In some embodiments, the 5'-internal domain comprise a sequence that is at least 80%, 85%, 90%, 95% or 100% identical to SEQ ID NO: 66. In some embodiments, the 3'-internal domain comprise a sequence that is at least 80%, 85%, 90%, 95% or 100% identical to SEQ ID NO: 67. In some embodiments, the 5'-internal domain is immediately adjacent to the 5'-ITR, and the 3'-internal domain is immediately adjacent to the 3'-ITR.

In some embodiments, the nucleic acid comprises one or more regulatory element sequences selected from the group consisting of SEQ ID NOs: 1-15 (e.g., SEQ ID NO: 2).

In some embodiments, the nucleic acid comprises one or more regulatory element sequences selected from the group consisting of SEQ ID NOs: 35-46 (e.g., SEQ ID NO: 36).

In some embodiments, the nucleic acid as described herein, further comprises a promoter and a sequence encoding a polypeptide. In some embodiments, the sequence encoding the polypeptide is operably linked to the promoter. In some embodiments, the sequence encoding a polypeptide is located between two regulatory element sequences.

In some embodiments, the nucleic acid as described herein, further comprises a promoter and a sequence encoding two or more polypeptides. In some embodiments, the sequence encoding the two or more polypeptides is operably linked to the promoter. In some embodiments, the sequence encodes an antibody heavy chain and an antibody light chain.

In some embodiments, the nucleic acid further comprises a WXRE sequence that is at least 80%, 85%, 90%, 95% or 100% identical to a sequence selected from the group consisting of SEQ ID NOs: 35-46. In some embodiments, the nucleic acid comprises two or more expression cassettes. In some embodiments, the nucleic acid comprises a selection marker. In some embodiments, the selection marker is an antibiotic resistance gene, a sequence encoding a fluorescent protein, or lacZ.

In one aspect, provided herein is a vector comprising the nucleic acid as described herein.

In one aspect, provided herein is a transposon vector comprising from 5' to 3': a 5' ITR sequence consisting of a sequence that is at least 95% identical to SEQ ID NO: 68; a non-transposon heterologous DNA sequence; and a 3'-ITR sequence consisting of a sequence that is at least 95% identical to SEQ ID NO: 60.

In some embodiments, the 5' ITR sequence consists of SEQ ID NO: 68 and the 3' ITR sequence consists of SEQ ID NO: 60.

In some embodiments, the transposon vector as described herein further comprises a 5'-internal domain and a 3'-internal domain. In some embodiments, the 5'-internal domain comprises a sequence that is at least 80%, 85%, 90%, 95% or 100% identical to SEQ ID NO: 66. In some embodiments, the 3'-internal domain comprises a sequence that is at least 80%, 85%, 90%, 95% or 100% identical to SEQ ID NO: 67. In some embodiments, the 5'-internal domain is immediately adjacent to the 5'-ITR, and the 3'-internal domain is immediately adjacent to the 3'-ITR.

In some embodiments, the non-transposon heterologous DNA sequence comprises a promoter and a sequence encoding one or more polypeptides. In some embodiments, the sequence encoding one or more polypeptides is operably linked to the promoter. In some embodiments, the promoter is a cytomegalovirus (CMV) promoter.

In some embodiments, the non-transposon heterologous DNA sequence further comprises a regulatory element sequence that is at least 80%, 85%, 90%, 95% or 100% identical to a sequence selected from the group consisting of SEQ ID NOs: 1-30 and 35-58.

In some embodiments, the non-transposon heterologous DNA sequence further comprises a WXRE sequence that is at least 80%, 85%, 90%, 95% or 100% identical to a sequence selected from the group consisting of SEQ ID NOs: 35-46.

In some embodiments, the non-transposon heterologous DNA sequence comprises a multiple cloning site.

In one aspect, provided herein is an expression system comprising: (a) a first nucleic acid comprising a 5'-ITR sequence, a non-transposon heterologous DNA sequence comprising a regulatory element sequence that is at least 80%, 85%, 90%, 95% or 100% identical to a sequence selected from the group consisting of SEQ ID NOs: 1-30 and 35-58, a 3'-ITR sequence; and (b) a second nucleic acid encoding a piggyBac transposase.

In some embodiments, the second nucleic acid encoding a piggyBac transposase having an amino acid sequence that is at least 80%, 85%, 90%, 95% or 100% identical to SEQ ID NO: 33.

In some embodiments, the non-transposon heterologous DNA sequence comprises a promoter and a sequence encoding one or more polypeptides. In some embodiments, the sequence encoding one or more polypeptides is operably linked to the promoter.

In some embodiments, the sequence encodes an antibody heavy chain and/or an antibody light chain. In some embodiments, the sequence encodes a monoclonal antibody, a bispecific antibody, a recombinant protein, or a fusion protein.

In some embodiments, the promoter is a CMV promoter. In some embodiments, the promoter is an inducible promoter (e.g., a heat shock promoter, a metallothionein promoter, or a glucocorticoid response element).

In some embodiments, the non-transposon heterologous DNA sequence further comprises a regulatory element sequence that is at least 80%, 85%, 90%, 95% or 100% identical to a sequence selected from the group consisting of SEQ ID NOs: 1-30 and 35-58.

In some embodiments, the non-transposon heterologous DNA sequence further comprises a WXRE regulatory element sequence that is at least 80%, 85%, 90%, 95% or 100% identical to a sequence selected from the group consisting of SEQ ID NOs: 35-46.

In one aspect, provided herein is an isolated nucleic acid comprising a regulatory element sequence that is at least 80%, 85%, 90%, 95% or 100% identical to a sequence selected from the group consisting of SEQ ID NOs: 1-30 and 35-58.

In some embodiments, the nucleic acid further comprises a promoter and a protein-coding sequence.

In some embodiments, the regulatory element sequence is located between the promoter and the protein-coding sequence.

In some embodiments, the regulatory element sequence is located at the 3' of the protein-coding sequence.

In some embodiments, the regulatory element sequence can be transcribed to a 5'-UTR or a 3'-UTR. In some embodiments, the isolated nucleic acid further comprises a 5'-ITR and a 3'-ITR, and the regulatory element sequence is located between the 5'-ITR and the 3'-ITR.

In one aspect, provided herein is a vector comprising the nucleic acid as described herein.

In one aspect, provided herein is a vector comprising a piggyBac transposon, the piggyBac transposon comprising the following genetic elements in a 5' to 3' direction: a 5'-ITR comprising a $TR_L$, a 5'-ITR spacer, a $IR_L$; a promoter; a regulatory element sequence that is at least 80%, 85%, 90%, 95% or 100% identical to a sequence selected from the group consisting of SEQ ID NOs: 1-30 and 35-58; a protein-coding sequence; and a 3'-ITR comprising a $IR_R$, a 3'-ITR spacer, a $TR_R$.

In one aspect, provided herein is a vector comprising a piggyBac transposon, the piggyBac transposon comprising the following genetic elements in a 5' to 3' direction: a 5'-ITR comprising a $TR_L$, a 5'-ITR spacer, a $IR_L$; a promoter; a protein-coding sequence; a regulatory element sequence that is at least 80%, 85%, 90%, 95% or 100% identical to a sequence selected from the group consisting of SEQ ID NOs: 1-30 and 35-58; and 3'-ITR comprising a $IR_R$, a 3'-ITR spacer, a $TR_R$.

In one aspect, provided herein is a vector comprising a piggyBac transposon, the piggyBac transposon comprising the following genetic elements in a 5' to 3' direction: a 3'-ITR comprising a $TR_R$, a 3'-ITR spacer, a $IR_R$; a promoter; a regulatory element sequence that is at least 80%, 85%, 90%, 95% or 100% identical to a sequence selected from the group consisting of SEQ ID NOs: 1-30 and 35-58; a protein-coding sequence; and a 5'-ITR comprising a $IR_L$, a 5'-ITR spacer, a $TR_L$.

In one aspect, provided herein is a vector comprising a piggyBac transposon, the piggyBac transposon comprising the following genetic elements in a 5' to 3' direction: a 3'-ITR comprising a $TR_R$, a 3'-ITR spacer, a $IR_R$, a promoter; a protein-coding sequence; a regulatory element sequence that is at least 80%, 85%, 90%, 95% or 100% identical to a sequence selected from the group consisting of SEQ ID NOs: 1-30 and 35-58; and a 5'-ITR comprising a $IR_L$, a 5'-ITR spacer, a $TR_L$.

In some embodiments, the 5'-ITR comprises or consists of a sequence that is at least 80%, 85%, 90%, 95% or 100% identical to a reverse sequence or a reverse complementary sequence of SEQ ID NO: 68.

In some embodiments, the 3'-ITR comprises or consists of a sequence that is at least 80%, 85%, 90%, 95% or 100% identical to a reverse sequence or a reverse complementary sequence of SEQ ID NO: 60.

In some embodiments, the $TR_L$ comprises or consists of a sequence that is at least 80%, 85%, 90%, 95% or 100% identical to a reverse sequence or a reverse complementary sequence of SEQ ID NO: 61.

In some embodiments, the 5'-ITR spacer comprises or consists of a sequence that is at least 80%, 85%, 90%, 95% or 100% identical to a reverse sequence or a reverse complementary sequence of SEQ ID NO: 62.

In some embodiments, the $IR_L$ comprises or consists of a sequence that is at least 80%, 85%, 90%, 95% or 100% identical to a reverse sequence or a reverse complementary sequence of SEQ ID NO: 63.

In some embodiments, the $TR_R$ comprises or consists of a sequence that is at least 80%, 85%, 90%, 95% or 100% identical to a reverse sequence or a reverse complementary sequence of SEQ ID NO: 64.

In some embodiments, the $IR_R$ comprises or consists of a sequence that is at least 80%, 85%, 90%, 95% or 100% identical to a reverse sequence or a reverse complementary sequence of SEQ ID NO: 65.

In some embodiments, the vector comprises two or more regulatory element sequences, each of which is at least 80%, 85%, 90%, 95% or 100% identical to a sequence selected from the group consisting of SEQ ID NOs: 1-30 and 35-58.

In some embodiments, the vector further comprises a 5'-internal domain sequence and a 3'-internal domain sequence.

In some embodiments, the 5'-internal domain sequence comprises or consists of a sequence that is at least or about 80%, 85%, 90%, 95% or 100% identical to SEQ ID NO: 66 and the 3'-internal domain sequence comprises or consists of a sequence that is at least or about 80%, 85%, 90%, 95% or 100% identical to SEQ ID NO: 67.

In some embodiments, the regulatory element sequence can be transcribed to a 5'-UTR or a 3'-UTR.

In some embodiments, the vector further comprises a sequence encoding a piggyBac transposase. In some embodiments, the sequence encoding the piggyBac transposase is outside a region between the 5'-ITR and the 3'-ITR.

In one aspect, provided herein is a method of generating a cell for expressing a polypeptide of interest, comprising: (a) introducing into a cell: a transposon vector comprising: a 5'-ITR (inverted terminal repeat) sequence; a 3'-ITR sequence; a regulatory element sequence that is at least 80%, 85%, 90%, 95% or 100% identical to a sequence selected from the group consisting of SEQ ID NOs: 1-30 and 35-58; and a sequence encoding the polypeptide of interest; and (b) culturing the cell under an appropriate condition. In some embodiments, the piggyBac transposon is integrated into the genome of the cell, thereby generating a cell for expressing the polypeptide of interest.

In some embodiments, the method further comprises introducing a vector comprising a sequence encoding a piggyBac transposase to the cell.

In some embodiments, the transposon vector comprises a sequence encoding a piggyBac transposase.

In some embodiments, the transposon vector is introduced into the cell by microinjection, high velocity propulsion, permeabilization, fusion, or electroporation. In some embodiments, the cell is a Chinese hamster ovary (CHO) cell. In some embodiments, the cell is a mammalian cell or an insect cell.

In one aspect, provided herein is a cell comprising the nucleic acid as described herein, the vector as described herein, or the expression system as described herein.

In some embodiments, the cell is a Chinese hamster ovary (CHO) cell.

In one aspect, provided herein is a method of expressing a protein, comprising: culturing the cell as described herein under conditions that allow the cell to express the protein; and collecting and purifying the protein.

In one aspect, provided herein is a protein expressed by the cell as described herein, or produced by the method as described herein.

In one aspect, provided herein is a pharmaceutical composition comprising the protein as described herein and a pharmaceutically acceptable carrier.

In one aspect, provided herein is a nucleic acid comprising a 5'-ITR sequence; a 3'-ITR sequence; and one or more regulatory element sequences derived from CHO.

In one aspect, provided herein is an expression system comprising: (a) a first nucleic acid comprising a piggyBac transposon comprising the following genetic elements in a 5' to 3' direction: a first TTAA sequence; a 5'-ITR comprising a $TR_L$, a 5'-ITR spacer and an $IR_L$; a 5'-internal domain (ID); a sequence of interest; a 3'-ID; a 3'-ITR comprising an $IR_R$, a 3'-ITR spacer and a $TR_R$; and a second TTAA sequence; and (b) a second nucleic acid encoding a piggyBac transposase.

In one aspect, provided herein is a method of generating a cell for expressing a polypeptide of interest, comprising: (a) introducing into a cell: a transposon vector comprising the following genetic elements in a 5' to 3' direction: a first TTAA sequence; a 5'-ITR comprising a $TR_L$, a 5'-ITR spacer and an $IR_L$; a 5'-internal domain (ID); a sequence of interest; a 3'-ID; a 3'-ITR comprising an $IR_R$, a 3'-ITR spacer and a $TR_R$; and a second TTAA sequence; and (b) culturing the cell under an appropriate condition.

In one aspect, provided herein is a cell line whose genome is stably integrated with a piggyBac transposon comprising the following genetic elements: a 5'-ITR sequence; a regulatory element sequence that is at least 80%, 85%, 90%, 95% or 100% identical to a sequence selected from the group consisting of SEQ ID NOs: 1-15; and a 3'-ITR sequence.

In one aspect, provided herein a cell line whose genome is stably integrated with a piggyBac transposon comprising the following genetic elements: a 5'-ITR comprising a $TR_L$, a 5'-ITR spacer and an $IR_L$; a 5'-internal domain (ID); a sequence of interest; a 3'-ID; a 3'-ITR comprising an $IR_R$, a 3'-ITR spacer and a TR.

In one aspect, the disclosure provides a transposon vector comprising a first PB transposase recognition site sequence comprising or consisting of a sequence that is at least 95% identical to SEQ ID NO: 31; a non-transposon heterologous DNA sequence; and a second PB transposase recognition site sequence comprising or consisting of a sequence that is at least 95% identical to SEQ ID NO: 32.

In one aspect, the disclosure is also related to a vector comprising the polynucleotide molecule as described herein. In some embodiments, the vector is a recombinant expression vector.

In some embodiments, provided herein is the vector that further comprises one or more genes encoding one or more proteins.

In some embodiments, the protein is an antibody, a fusion protein, an enzyme, a soluble protein, a membrane protein, a structural protein, a ribosome protein, a zymogen, a cell surface receptor protein, a transcriptional regulatory protein, a translational regulatory protein, a chromatin protein, a hormone, a cell cycle regulatory protein, a G protein, a neuroactive peptide, an immunomodulatory protein, a blood component protein, an ion gate protein, a heat shock protein, dihydrofolate reductase, an antibiotic resistance protein, a functional fragment of any one of the proteins, an epitope fragment of any one of the proteins, and any combination thereof.

In one aspect, the disclosure is related to a recombinant host cell comprising the vector as described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 5 shows the sequence of (1) piggyBac 5'-ITR; (2) piggyBac 3'-ITR; and (3) piggyBac transposase amino acid.

FIG. 6 shows the sequence of WXRE IDs: A-L.

FIG. 7 shows the reverse complementary sequence of WXRE IDs: A-L.

FIG. 8 shows the sequence of human CMV promoter and human EF-1α gene intron 1.

FIG. 11 illustrates the influence on the expression level of the fusion protein after adding transcriptional regulatory elements A~K, wherein A1 and A2 illustrate the forward and reverse directions of transcriptional regulatory element A respectively, and so forth.

FIG. 15 illustrates the comparison of the expression level of Adalimumab on 14th day under different combined conditions of the transcriptional regulatory elements, wherein in sample 1 to sample 12, the components of the transcriptional regulatory element in the upstream of the heavy chain and the transcriptional regulatory element in the upstream of the light chain are found in Table 8.

FIG. 16 illustrates the amino acid sequences of the A chain of PD-L1, the heavy chain (HC) of Adalimumab and the light chain (LC) of Adalimumab.

DETAILED DESCRIPTION

Figure 1A:
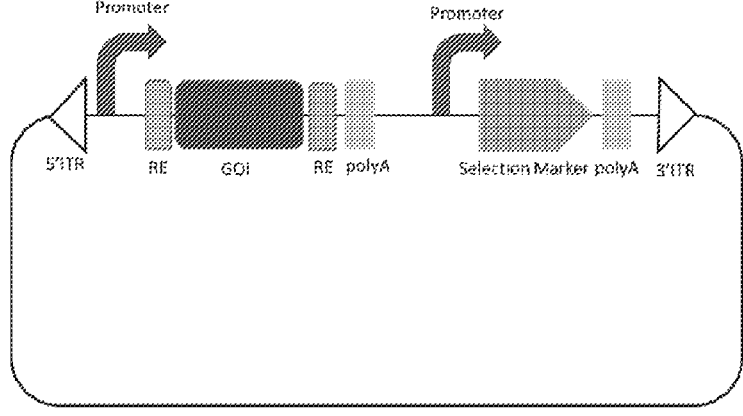
FIG. 1A is a schematic diagram showing a piggyBac transposon plasmid.

DNA transposon is a type of repeat sequence naturally exists in animal genomes. The piggyBac transposon was first discovered in insect genomes, and the sequence contains key elements including transposases and inverted terminal repeat sequences. The piggyBac transposon system can "cut and paste" between the genome and plasmids to replace DNA sequences. As compared to other transposon systems, the piggyBac transposase is capable of precisely replacing the terminal inversely repeat sequences and the sequence located between the repeat sequences into the genomic DNA comprising the "TTAA" nucleotide sequence, without any other modifications or loss of the genomic DNA. The transposon systems have been used in stem cell studies, gene modifications and many cell-engineering areas.

Faster and more efficient protein expression technology is one of the major interests in academia and industry. The transient expression technology can deliver gram-scale recombinant proteins in about two weeks, but with significant compromise in productivity as opposed to classical stable cell pool. On the other hand, the stable cell pool suffers from low possibilities of exogenous DNA integration into the genome, as the integration of exogenous DNA into the genome usually occurs in random fashion. This inefficient DNA integration issue can cause slow recovery during antibiotic selection. While the recombinant protein expression level is fairly high, the time-consuming preparation of stable pool generation limits the use of this classical technology to meet the demand of industry.

Some existing transposon systems can be used to generate stable cell line that can produce recombinant proteins. However, these systems (e.g., the Tol2 transposon) usually take more than one month to establish an acceptable stable cell line, rendering its limited advantage over classical stable cell pool approach unappealing. Other transposon systems (e.g., Sleeping Beauty, and Mos1) are much less efficient as compared to the piggyBac system for CHO cell lines as described in the present disclosure.

In addition, exogenous protein expression can be regulated by regulatory elements (REs). Many factors that regulate transcription as well as translation can have an impact on protein expression level. This disclosure also provides many DNA regulatory elements that have been identified by RNA abundance analysis. Experiments were further performed to demonstrate that they can improve exogenous protein expression.

The present disclosure provides a highly efficient expression system that utilizes piggyBac transposons and/or regulatory elements. The expression system can create stable cell lines that can express recombinant proteins at an increase level in a relatively short time.

PiggyBac Transposons and Transposase

DNA-based transposon systems first emerged as efficient tools for genome engineering of mammalian cells after the Sleeping Beauty transposon system was resurrected from the genome of the medaka fish. Transposon DNA vectors can be engineered for a variety of purposes, including transgenesis, gene therapy, gene trapping, or insertion of other DNA elements into the genomes of cells. The piggyBac (PB) transposon system is naturally active and was first discovered in insect cells while propagating Baculo-virus in the TN-386 cell line, from the cabbage looper moth *Trichoplusia ni*.

PiggyBac-based gene transfer or mobilization is carried out through a 'cut and paste' mechanism. When the piggy-Bac transposase protein is expressed in mammalian cells, it binds to the inverted repeats of the transposon, nicking the DNA and freeing a 3' hydroxyl group at both ends of the transposon. This results in hydrophilic attack of the flanking TTAA sequence and hairpin formation, freeing the transposon from its plasmid backbone. The plasmid backbone is then repaired by host cell factors by ligation of the complementary TTAA overhangs. PiggyBac transposase locates TTAA sequences in the genomic DNA of the mammalian cells. Through hairpin resolution of the transposon and hydrophilic attack of the genomic DNA by 30 hydroxyl groups on the transposon, a staggered four base-pair (bp) cut in the genomic DNA is produced, creating a transient double strand (ds) break with TTAA overhangs on both sides of the break. The transposon is then inserted into the genomic DNA at the TTAA site, resulting in a duplication of this TTAA, such that a TTAA is found on both sides of the transposon. The sequence will be inserted into the genome, and the sequence will be passed on to all of the progeny cells. Upon excision of the transposon by piggyBac transposase, which can be induced and selected for to rid the cells of the transgene, the single-stranded TTAAs are religated to reform a single TTAA. Thus, the unique mechanism of piggyBac transposition results in a unique advantage: seamless excision of the transposon sequence. After piggyBac excises the transposon from DNA, it seamlessly generates the original piggyBac target site. A detailed description of piggyBac can be found e.g., in Woodard, et al., "piggyBacing models and new therapeutic strategies." Trends in biotechnology 33.9 (2015): 525-533; Cary et al. "Transposon mutagenesis of baculoviruses: analysis of *Trichoplusia ni* transposon IFP2 insertions within the FP-locus of nuclear polyhedrosis viruses." Virology 172.1 (1989): 156-169; both of which are incorporated herein by reference in the entirety.

The wildtype piggyBac is a 2472-bp transposon with inverted terminal repeats (ITRs) and a 594-amino acid transposase within ITRs. The PB transposase recognizes the PB 5'-ITR and the PB 3'-ITR. The wildtype 5'-ITR includes the left terminal repeat (TR$_L$), a 31-bp spacer (5'-ITR spacer), and left internal repeat (IR$_L$). The sequence of the wildtype 5'-ITR is CCCTAGAAAGATAATCATAT-TGTGACGTACGTTAAAGATAATCATGCGTAAAAT-TGA CGCATG (SEQ ID NO: 68). In the wildtype 5'-ITR, the sequence of the TR$_L$ is CCCTAGAAAGATA (SEQ ID NO: 61); the sequence of the 31-bp spacer is ATCATAT-TGTGACGTACGTTAAAGATAATCA (SEQ ID NO: 62); and the sequence of the IR$_L$ is TGCGTAAAATTGACG-CATG (SEQ ID NO: 63).

Similarly, the wildtype 3'-ITR includes the right terminal repeat (TR$_R$), a short spacer (GAC; the 3'-ITR spacer), and the right internal repeat (IR$_R$). The sequence of the wildtype 3'-ITR is CATGCGTCAATTTTACGCAGAC-TATCTTTCTAGGG (SEQ ID NO: 60). In wildtype 3'-ITR, the sequence of the TR$_R$ is TATCTTTCTAGGG (SEQ ID NO: 64); the sequence of the IR$_R$ is CATGCGTCAATTT-TACGCA (SEQ ID NO: 65). As shown in FIG. 5, the terminal repeats are indicated by single underline, and the internal repeats are indicated by double underlines.

As used herein, the term "5'-ITR" refers to a sequence that is recognized by the piggyBac transposase for the transposon activity, including TR$_L$, IR$_L$, and optionally with a spacer therebetween (e.g., the 31-bp spacer). As used herein, the term "3'-ITR" refers to a sequence that is recognized by the piggyBac transposase for the transposon activity, including TR$_R$, IR$_R$, and optionally with a spacer therebetween.

Figure 1B:
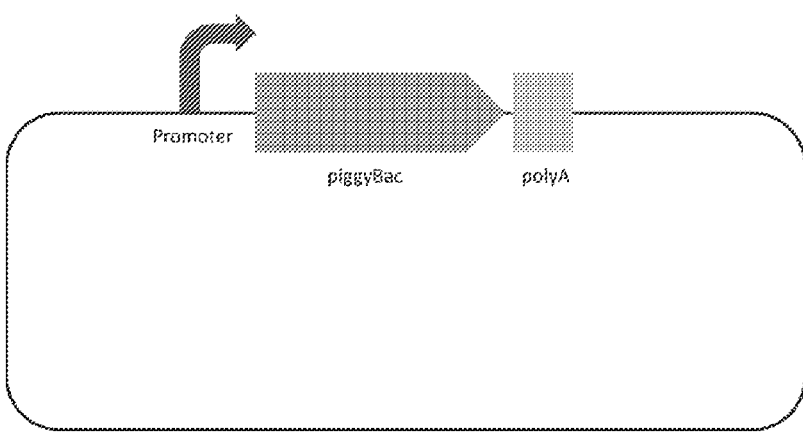
FIG. 1B is a schematic diagram showing a piggyBac transposase plasmid.

The present disclosure provides a piggyBac expression system. In some embodiments, the piggyBac transposase and piggyBac transposon are carried on two separate plasmids (e.g., the transposon vector and the transposase vector) (FIGS. 1A-1B). It is also possible to deliver the transposase and transposon on the same plasmid (cis) with the transposase gene outside of the transposon inverted terminal repeat elements (ITRs).

In some embodiments, the transposon vector has piggyBac (PB) 5'- and 3'-inverted terminal repeats (ITRs). The 5'-ITR can comprise or consist of e.g., TR$_L$, and IR$_L$, and optionally a spacer sequence (e.g., the 31-bp spacer). The 3'-ITR can comprise or consist of e.g., TR$_R$, and IR$_R$, and optionally a spacer sequence (e.g., GAC). The sequence of interest (e.g., gene of interest or GOI) can be inserted into the vector between the 5'-ITR and the 3'-ITR or between PB transposase recognition site sequences. In some embodiments, the GOI is operably linked to a promoter. In some embodiments, the GOI is operably linked to one, two, three, four, five, or more regulatory elements. The regulatory element can be located at 5' of GOI or at 3' of GOI. In some embodiments, the regulatory element is between the promoter and GOI or between GOI and a polyA signal sequence. The poly A signal sequence provides the signal for polyadenylation on the transcribed mRNA. In some embodiments, the transposon vector can further comprise a selection marker. The selection marker can be operably linked to the same promoter or a different promoter. In some embodiments, the selection marker and GOI can be under the control of the same promoter. In some embodiments, the selection marker can have its own promoter. Usually, the host cell's genome does not itself provide a selection marker functionality. Thus, the cells with the correct modification can be screened for the selection marker.

In some embodiments, the sequence of interest comprises various genetic elements, e.g., restriction sites, loxP sites, regulatory elements, promoters, enhancers, expression cassettes, genetic operons, etc. In some embodiments, the sequence of interest does not have any protein coding sequences.

In some embodiments, a PB transposase vector is provided. The PB transposase vector is designed to express the PB transposase. During the experiments, host cells (e.g., CHO-K1 cells) are transfected with both vectors. The PB transposase expressed from the PB transposase vector recognizes the PB 5'-ITR and the PB 3'-ITR located on the transposon vector and efficiently moves and integrates the nucleic acid sequence between the PB 5'- and 3'-ITRs (including both the PB 5'- and 3'-ITRs) into a chromosomal TTAA site in the cells. In some embodiments, the cells are then selected by the selection marker (e.g., an antibiotic resistance gene) and protein expression activity.

In some embodiments, the 5'- and 3'-internal domains can be used in connection with 5'-ITR and 3'-ITR to increase the integration efficiency of the PB transposon (e.g., by at least 10%, 20%, 30%, 40%, 50% as compared a PB transposon without the 5'- or 3'-internal domain sequences). In some embodiments, the PB transposon recognition site comprises a 5'-internal domain sequence that is at least 80%, 85%, 90%, 91%, 92%, 93%, 94%, 95%, 96%, 97%, 98%, 99%, or 100% identical to the 5'-internal domain sequence as shown in FIG. 5. The 5'-internal domain in sequence FIG. 5 is: TGTTTTATCGGTCTGTATATCGAGGTTTATTTAT-TAATTTGAATAGATATTAAGTTTT    ATTATATTTA- CACTTACATACTAATAATAAATTCAACAAACAATTT-
ATTTATGTTTAT
TTATTTATTAAAAAAAAACAAAAACTCAAAAT-
TTCTTCTATAAAGTAACAAAACT (SEQ ID NO: 66).

In some embodiments, the PB transposon recognition site comprises a 3'-internal domain sequence. The 3'-internal domain sequence can be at least 80%, 85%, 90%, 91%, 92%, 93%, 94%, 95%, 96%, 97%, 98%, 99%, or 100% identical to the 3'-internal domain sequence as shown in FIG. 5. The 3'-internal domain sequence in FIG. 5 is: TATC-TATAACAAGAAAATATATATATAATAAGTTAT-CACGTAAGTAGAACATGAAAT AACAATATAAT-TATCGTATGAGTTAAATCTTAAAAGTCACGTAAAA-GATAATCATGC GTCATTTTGACTCACGCGGTCGT-TATAGTTCAAAATCAGTGACACTTACCGCATTGA CAAGCACGCCTCACGGGAGCTCCAAGCGGCGACT-GAGATGTCCTAAATGCACAGCG ACGGATTCGCGCT-ATTTAGAAAGAGAGAGCAATATTTCAAGAATG (SEQ ID NO: 67).

In some embodiments, the PB transposon comprises a 5'-internal domain sequence that has at least or about 50, 100, 110, 120, 130, 140, 150, 160, 170 or 172 contiguous nucleotides of SEQ ID NO: 66. In some embodiments, the PB transposon comprises a 3'-internal domain sequence that has at least or about 50, 100, 110, 120, 130, 140, 150, 160, 170, 180, 190, 200, 210, 220, 230, 240, 250, 260, 270, or 272 contiguous nucleotides of SEQ ID NO: 67.

In some embodiments, the PB transposon does not have 5'-internal domain sequence. In some embodiments, the PB transposon does not have 3'-internal domain sequence.

As used herein, the term "PB transposase 5'-recognition site" refers one of the pair of the two sites that the PB transposase recognizes and interacts with, which is located on the 5'-direction of a nucleic acid (e.g., based on the 5' to 3' direction on the sense strand of the coding sequence or a reference sequence). The term "PB transposase 3'-recognition site" refers one of the pair of the two sites that the PB transposase recognizes and interacts with, which is located on the 3'-direction of a nucleic acid (e.g., based on the 5' to 3' direction on the sense strand of the coding sequence or a reference sequence). In some embodiments, the PB transposase 5'-recognition site sequence comprises or consists of $TR_L$. In some embodiments, the PB transposase 3'-recognition site sequence comprises or consists of $TR_R$. In some embodiments, the PB transposase 5'-recognition site comprises or consists of $TR_L$ and $IR_L$, and optionally with a spacer and/or the internal domain sequence. In some embodiments, the PB transposase 3'-recognition site comprises or consists of $TR_R$ and $IR_R$, and optionally with a spacer and/or the internal domain sequence.

The location for 5'-ITR and 3'-ITR can be exchanged on the transposon vector. Thus, in some embodiments, the PB transposase 3'-recognition site sequence comprises or consists of $TR_L$. In some embodiments, the PB transposase 5'-recognition site sequence comprises or consists of $TR_R$. In some embodiments, the PB transposase 3'-recognition site comprises or consists of $TR_L$ and $IR_L$, and optionally with a spacer and/or the internal domain sequence. In some embodiments, the PB transposase 5'-recognition site comprises or consists of $TR_R$ and $IR_R$, and optionally with a spacer and/or the internal domain sequence.

In some embodiments, the PB transposase 5'-recognition site comprises or consists of a sequence that is at least 80%, 85%, 90%, 91%, 92%, 93%, 94%, 95%, 96%, 97%, 98%, 99%, or 100% identical to SEQ ID NO: 31. In some embodiments, the PB transposase 3'-recognition site comprises or consists of a sequence that is at least 80%, 85%, 90%, 91%, 92%, 93%, 94%, 95%, 96%, 97%, 98%, 99%, or 100% identical to SEQ ID NO: 32. In some embodiments, the PB transposase 5'-recognition site comprises or consists of a sequence that has at least or about 50, 100, 110, 120, 130, 140, 150, 160, 170, 180, 190, 200, 210, 220, or 230 contiguous nucleotides or the entire sequence of SEQ ID NO: 31. In some embodiments, the PB transposase 3'-recognition site comprises or consists of a sequence that has at least or about 50, 100, 110, 120, 130, 140, 150, 160, 170, 180, 190, 200, 210, 220, 230, 240, 250, 260, 270, 280, 290, 300, or 310 contiguous nucleotides or the entire sequence of SEQ ID NO: 32.

In some embodiments, the length of the sequence between ITRs or PB transposase recognition sites is at least or about 1, 2, 3, 4, 5, 6, 7, 8, 9, 10, 20, 30, 40, 50, 60, 70, 80, 90, or 100 kb. In some embodiments, the transposon comprises an insert of ranging between 1.5-3 kb, 1.5-5 kb, 1.5-10 kb, 1.5-20 kb, 1.5-30 kb, 1.5-50 kb, 1.5-75 kb, 2-5 kb, 2-10 kb, 2-20 kb, 2-30 kb, 2- 50 kb, 2-75 kb, 3-5 kb, 3-10 kb, 3-20 kb, 3-30 kb, 3-50 kb, 3-75 kb, 5-10 kb, 5-20 kb, 5-30 kb, 5-50 kb, 5-75 kb, 10-20 kb, 10-30 kb, 10-50 kb, or 10-75 kb.

The present disclosure also provides a vector for making a transposon vector containing a gene of interest or a sequence of interest. In some embodiments, the vector comprises a 5'-ITR and a 3'-ITR as described herein, and a linker sequence between 5'-ITR and 3'-ITR. In some embodiments, the vector comprises a PB transposase 5'-recognition site and a PB transposase 3'-recognition site as described herein, and a linker sequence between the two recognition sites. In some embodiments, the linker sequence is a short length of DNA (e.g., less than 20, 30, 40, 50, 60, 70, 80, 90, 100 or 200 nucleotides) that contains numerous different endonuclease restrictions sites located in close proximity. The presence of the linker sequence is advantageous because it allows various exogenous sequences, such as expression cassettes, to be easily inserted and removed, thus simplifying the process of making a vector containing a particular targeted DNA fragment. As used herein, an expression cassette is a distinct component of a vector or a sequence having a gene to be expressed by a transfected cell and regulatory sequences for the gene. In some embodiments, the transposon vector can have various regulatory elements or genetic elements, such as promoters (e.g., inducible promoters), enhancers, or insulators, and the like.

When this transposon vector is introduced into a host cell, in the presence of transposase activity specific for the flanking inverted repeats, the targeted DNA sequence will be excised from the introduced vector and will be inserted into a location in the genome. Transposition of the targeted DNA is facilitated in the presence of transposase activity. The gene encoding the transposase can either be physically linked to the transposon vector, already present in the host cell's genome, or introduced into the cell as part of a separate vector. In some embodiments, inducible promoters can be used as a means of triggering the production or transposase activity.

Regulatory Elements

The present disclosure also provides various regulatory elements. As used herein, the term "regulatory element" in the present disclosure refers to a sequence that is involved in the regulation of gene transcription and/or translation. In some embodiments, the regulatory element is a transcription regulatory element or a translation regulatory element. In some embodiments, the regulatory element can stabilize mRNA. In some embodiments, these regulatory elements are derived from CHO-K1 cells. In some embodiments, these regulatory elements can increase expression level of gene of interest.

The present disclosure demonstrates that the regulatory elements as listed in Table 1 can increase the expression level of the gene of interest. Without wishing to be bound by theory, it has been hypothesized that these regulatory elements can increase the transcription efficiency and stabilize the transcribed mRNA. In some embodiments, these regulatory elements can make the mRNA resistant to degradation.

SEQ ID NOs: 1-15 are the sequences for the regulatory elements. The reverse complementary sequences are provided in SEQ ID NOs: 16-30. In one aspect, the disclosure provides an isolated polynucleotide molecule comprising (i) a sequence of any of SEQ ID NOs: 1-15; (ii) a reverse complementary sequence of the sequence of any of SEQ ID NOs: 1-15; (iii) a reverse complementary sequence of a sequence capable of hybridizing with the sequence of (i) or (ii) under a high stringency hybridization condition or a very high stringency hybridization condition; and (iv) a sequence having at least or about 80%, 85%, 90%, 91%, 92%, 93%, 94%, 95%, 96%, 97%, 98%, 99% identical to SEQ ID NOs: 1-30. As used herein, the term "reverse complementary sequence" in the present disclosure is a sequence which is opposite to the direction of the sequence of the original polynucleotide and is also complementary to the sequence of the original polynucleotide. Illustratively, if the original polynucleotide sequence is ACTGAAC, then the reverse complementary sequence thereof is GTTCAGT.

In one aspect, the disclosure also provides a sequence comprising a promoter and a gene of interest. The regulatory element sequence can be located at the 5' of the gene of interest (e.g., between the promoter and the gene of interest) or at the 3' of the gene of interest (e.g., between the gene of interest and a poly A signal sequence).

In some embodiments, the regulatory element has a sequence identity of at least or about 80%, 81%, 82%, 83%, 84%, 85%, 86%, 87%, 88%, 89%, 90%, 91%, 92%, 93%, 94%, 95%, 96%, 97%, 98%, 99%, or 100% (including all the ranges and percentages between these values) with the sequence of any of SEQ ID NOs: 1-30. In some embodiments, the sequence differs from a sequence selected from SEQ ID NOs: 1-30 by at least or about 1, 2, 3, 4, 5, 6, 7, 8, 9, or 10 nucleotides. In some embodiments, the sequence differs from a sequence selected from SEQ ID NOs: 1-30 by no more than 1, 2, 3, 4, 5, 6, 7, 8, 9, or 10 nucleotides.

The sequence can have a forward direction or a reverse direction. In some embodiments, the regulatory element sequence can increase the expression amount of a heterologous protein by about or at least 1%, 2%, 3%, 4%, 5%, 6%, 7%, 8%, 9%, 10%, 20%, 30%, 40%, 50%, 60%, 70%, or 80% (e.g., as compared to a control sequence without the regulatory element sequence).

The regulatory element sequence can be located after the promotor (e.g., from 5' to 3' on the sense strand of the coding sequence) or after the polynucleotide encoding a polypeptide (e.g., from 5' to 3' on the sense strand of the coding sequence). In some embodiments, the regulatory element is located before the polynucleotide encoding a polypeptide (e.g., transcribed to a 5'-untranslated region (5'-UTR)). In some embodiments, there are at least or about 0, 1, 2, 3, 4, 5, 6, 7, 8, 9, 10, 100, 200, 300, 400, 500, 600, 700, 800, 900, or 1000 nucleotides between the regulatory element sequence and the promoter or between the regulatory element sequence and the polynucleotide encoding a polypeptide. In some embodiments, there are no more than 1, 2, 3, 4, 5, 6, 7, 8, 9, 10, 100, 200, 300, 400, 500, 600, 700, 800, 900, or 1000 nucleotides between the regulatory element sequence and the promoter or between the regulatory element sequence and the polynucleotide encoding a polypeptide.

In some embodiments, the regulatory element is located after (e.g., immediately after) the polynucleotide encoding a polypeptide (e.g., transcribed to a 3'-UTR). In some embodiments, there are at least or about 0, 1, 2, 3, 4, 5, 6, 7, 8, 9, 10, 100, 200, 300, 400, 500, 600, 700, 800, 900, or 1000 nucleotides between the regulatory element sequence and the end of the sequence encoding the polypeptide or between the regulatory element sequence and the polyA signal sequence. In some embodiments, there are no more than 0, 1, 2, 3, 4, 5, 6, 7, 8, 9, 10, 100, 200, 300, 400, 500, 600, 700, 800, 900, or 1000 nucleotides between the regulatory element sequence and the end of the sequence encoding the polypeptide or between the regulatory element sequence and the poly A signal sequence.

The present disclosure also provides methods of screening regulatory element sequence. In some embodiments, RNA sequencing (RNA-seq) can be used to sequence and quantify mRNAs in cells (e.g., CHO cells). Total RNA is extracted. In some embodiments, cDNA is generated from the extracted RNA. The amount of RNA is ranked by abundance. And the sequence at the untranslated regions of the top ranked RNA is selected. In some embodiments, experiments as described herein are performed to verify the effects of the regulatory elements on protein expression. In one aspect, mRNA of a desired host cell (e.g., CHO-K1 cell) at different stages are sequenced and quantified by a high throughput sequencing method (e.g., RNA-seq). In some embodiments, transient transfection as well as stable transfection can be performed. Total RNA can be extracted from an appropriate number of (e.g., at least or about 10, 20, or 30) samples after an appropriate time (e.g., on day 6, day 8, day 10, day 12, or day 14) by transient transfection, or from an appropriate number (e.g. at least or about 10, 20, or 30) of stable transfection samples (e.g., stable protein expressing cell lines) after an appropriate time (e.g., on day 6, day 8, day 10, day 12, or day 14) of a traditional fed-batch process (e.g., 14-day fed-batch process).

In some embodiments, cDNA can be generated accordingly (e.g., by reverse transcription) and used for sequencing (e.g., high throughput sequencing). With sequencing data and the relative reads number, mRNA can be extracted and ranked by average abundance across all samples. In some embodiments, regulatory element (RE) sequences can be extracted from the untranslated regions of top ranked mRNAs (e.g., at least or about the top 5, 10, 15, 20, 25, 30, 35, 40, or more).

In some embodiments, the regulatory element sequences as described herein can be incorporated into a fusion protein expression plasmid (e.g., immediately before, or immediately after the recombinant protein expressing gene). In some embodiments, a control sample that does not contain any regulatory element sequences can be used to determine the effects of the regulatory elements.

WXRE Regulatory Elements

Figure 6:
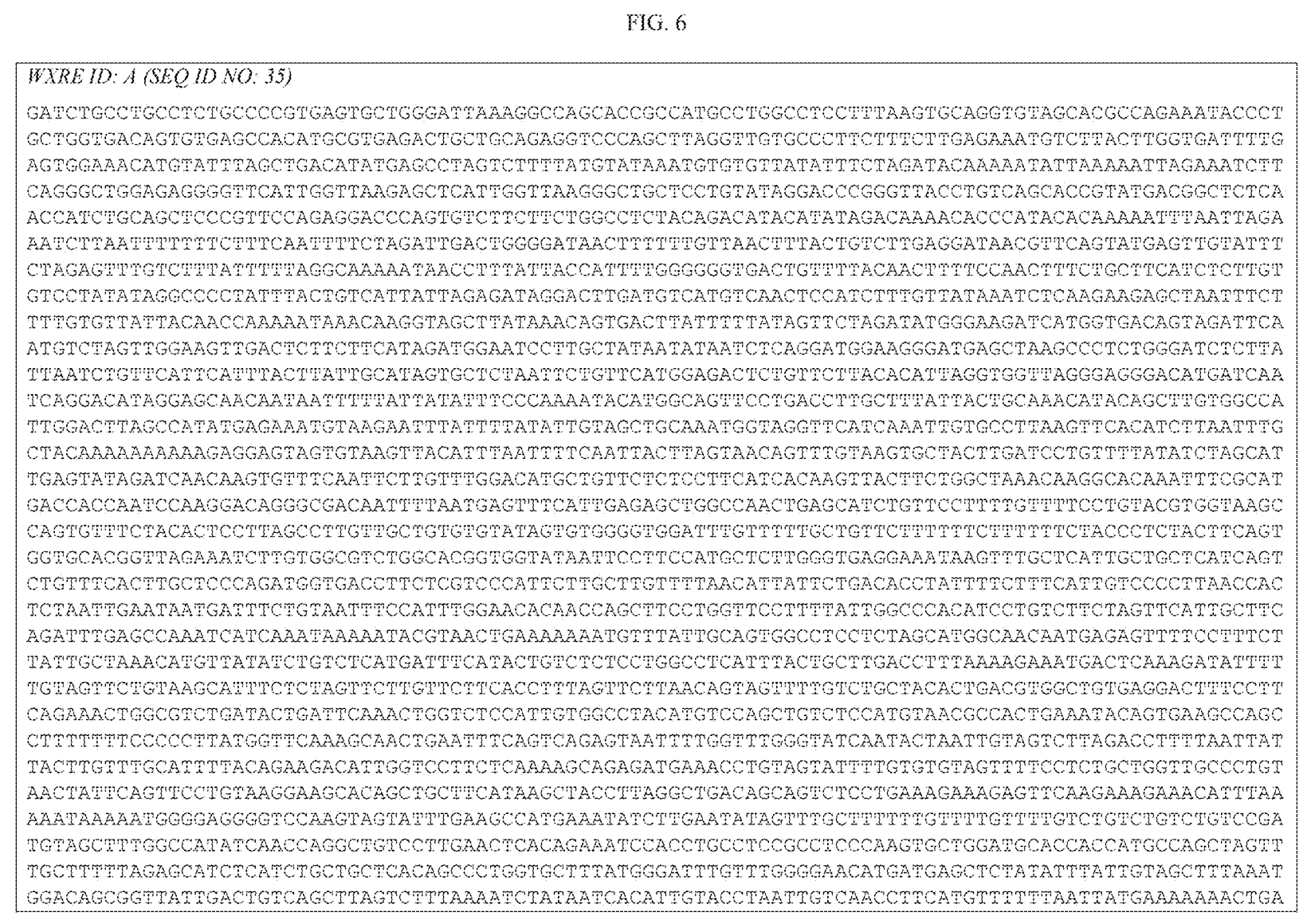
Figure 6:
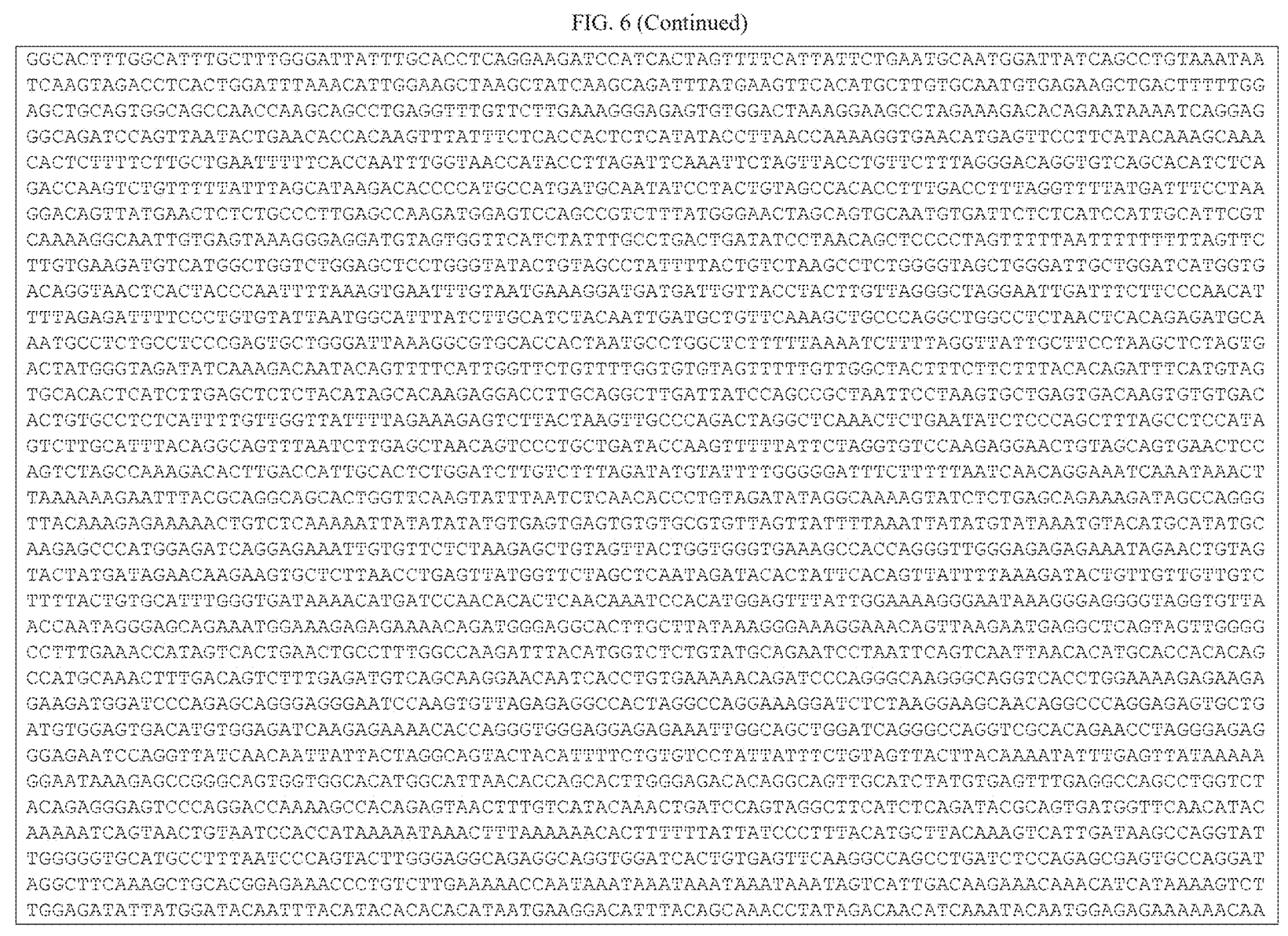
Figure 7:
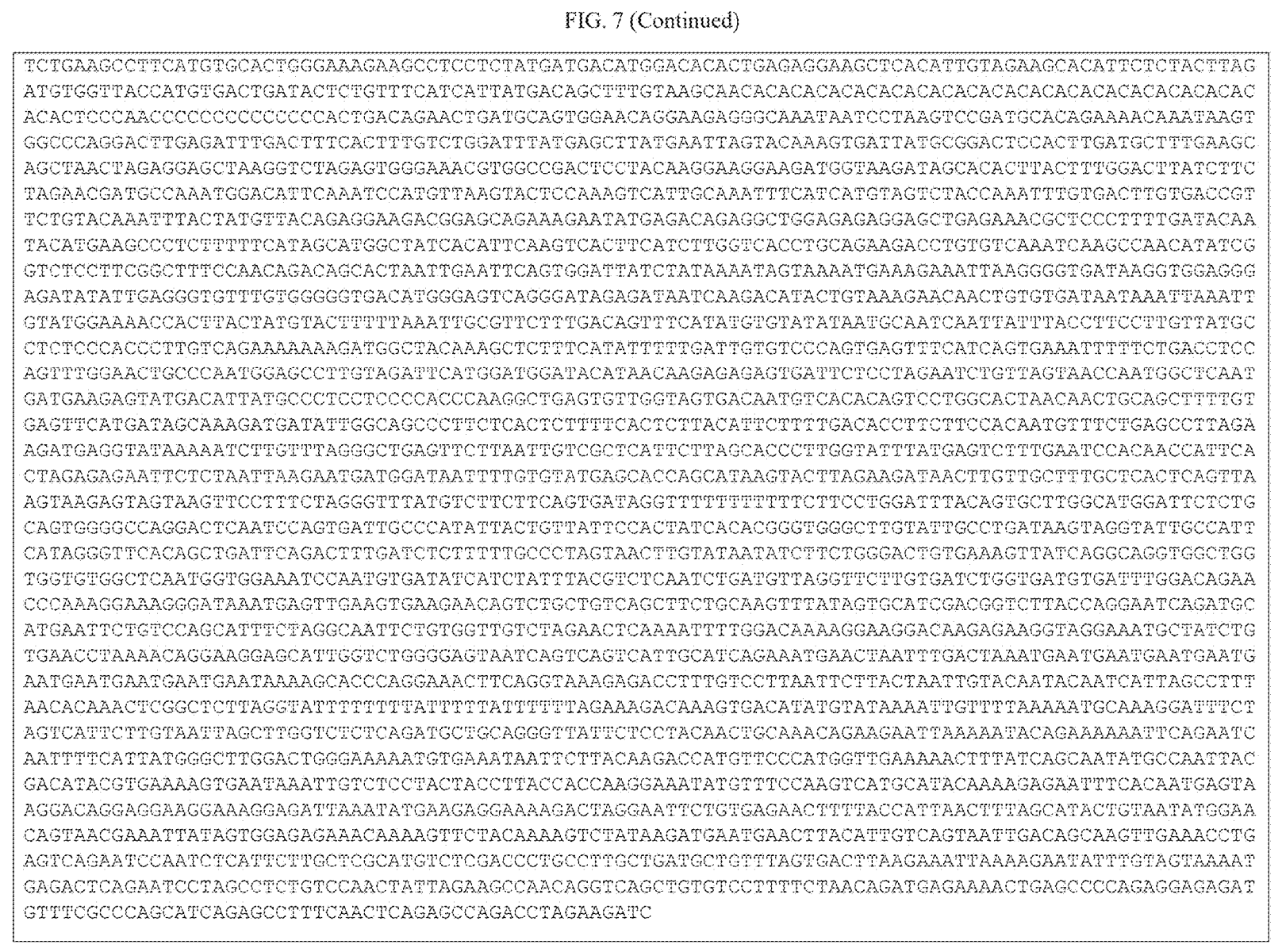
Figure 7:
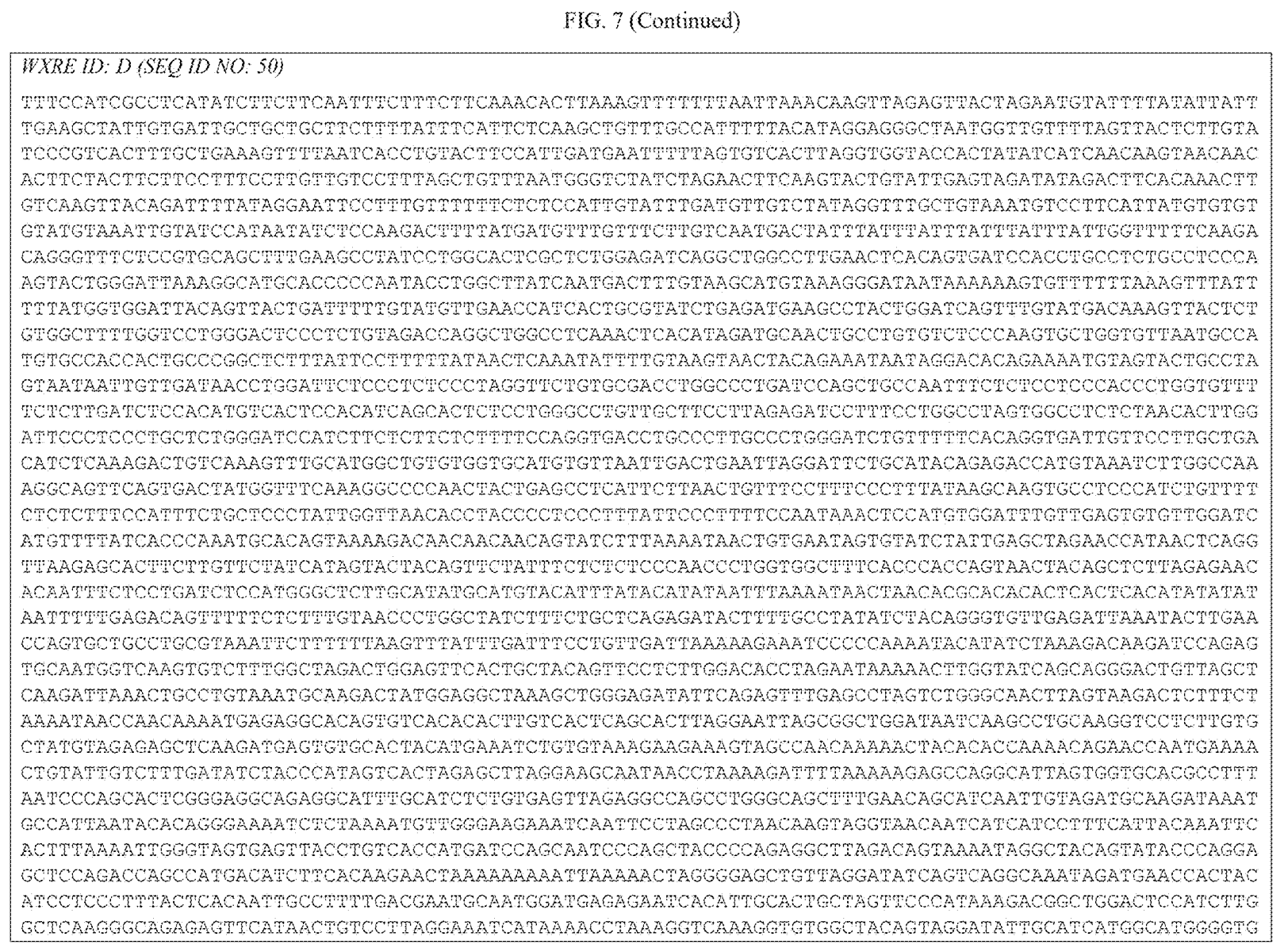

A regulatory element can regulate gene transcription and/or translation. In some embodiments, the regulatory element is a transcription regulatory element, e.g., a WXRE regulatory element. As shown in FIG. 6, the WXREs in the present disclosure include transcription regulatory element A (SEQ ID NO: 35), transcription regulatory element B (SEQ ID NO: 36), transcription regulatory element C (SEQ ID NO: 37), transcription regulatory element D (SEQ ID NO: 38), transcription regulatory element E (SEQ ID NO: 39), transcription regulatory element F (SEQ ID NO: 40), transcription regulatory element G (SEQ ID NO: 41), transcription regulatory element H (SEQ ID NO: 42), transcription regulatory element I (SEQ ID NO: 43), transcription regulatory element J (SEQ ID NO: 44), transcription regulatory element K (SEQ ID NO: 45), and transcription regulatory element L (SEQ ID NO: 46). Accordingly, as shown in FIG. 7, the reverse complementary sequence of the WXREs in the present disclosure include the reverse complementary sequence of transcription regulatory element A (SEQ ID NO: 47), the reverse complementary sequence of transcription regulatory element B (SEQ ID NO: 48), the reverse complementary sequence of transcription regulatory element C (SEQ ID NO: 49), the reverse complementary sequence of transcription regulatory element D (SEQ ID NO: 50), the reverse complementary sequence of transcription regulatory element E (SEQ ID NO: 51), the reverse complementary sequence of transcription regulatory element F (SEQ ID NO: 52), the reverse complementary sequence of transcription regulatory element G (SEQ ID NO: 53), the reverse complementary sequence of transcription regulatory element H (SEQ ID NO: 54), the reverse complementary sequence of transcription regulatory element I (SEQ ID NO: 55), the reverse complementary sequence of transcription regulatory element J (SEQ ID NO: 56), the reverse complementary sequence of transcription regulatory element K (SEQ ID NO: 57), and the reverse complementary sequence of transcription regulatory element L (SEQ ID NO: 58).

In some embodiments, the WXRE sequence has a sequence identity of at least or about 80%, 81%, 82%, 83%, 84%, 85%, 86%, 87%, 88%, 89%, 90%, 91%, 92%, 93%, 94%, 95%, 96%, 97%, 98%, 99%, or 100% (including all the ranges and percentages between these values) with the sequence of any of SEQ ID NOs: 35-58. In some embodiments, the WXRE sequence differs from a sequence selected from SEQ ID NOs: 35-58 by at least or about 1, 2, 3, 4, 5, 6, 7, 8, 9, or 10 nucleotides. In some embodiments, the WXRE sequence differs from a sequence selected from SEQ ID NOs: 35-58 by no more than 1, 2, 3, 4, 5, 6, 7, 8, 9, or 10 nucleotides.

The WXRE sequence can have a forward direction or a reverse direction. As used herein, a sequence of interest has a forward direction when the sense strand (from 5' to 3') has a sequence that is identical to the sequence of interest. A sequence of interest has a reverse direction when the sense strand has a sequence that is reverse complementary to the sequence of interest. The sequences that are reverse complementary to SEQ ID NOs: 35-46 are set forth in SEQ ID NO: 47-58, respectively.

In some embodiments, the WXRE sequence can increase the expression amount of a heterologous protein by about or at least 10%, 20%, 30%, 40%, 50%, 60%, 70%, or 80% (e.g., as compared to a control sequence without the WXRE sequence).

In some embodiments, the WXRE sequence, the promotor, and the polynucleotide encoding a polypeptide are operably linked together. In some embodiments, the WXRE sequence, the promotor, the polynucleotide encoding a polypeptide, and one or more additional regulatory elements are operably linked together. In some embodiments, the additional regulatory elements are regulatory elements as described herein (e.g., SEQ ID NOs: 1-30). In some embodiments, an intron of EF-1α (e.g., the first intron of human EF-1α) can be used to increase the expression. The WXRE sequence, the promotor, and the polynucleotide encoding a polypeptide that are operably linked together can have various orders. For example, the WXRE sequence can be located before the promotor (e.g., from 5' to 3' on the sense strand of the coding sequence) or after the polynucleotide encoding a polypeptide (e.g., from 5' to 3' on the sense strand of the coding sequence). In some embodiments, there are at least or about 0, 1, 2, 3, 4, 5, 6, 7, 8, 9, 10, 100, 200, 300, 400, 500, 600, 700, 800, 900, 1000, 2000, 3000, 4000 or 5000 nucleotides between the WXRE sequence and the promoter or between the WXRE sequence and the polynucleotide encoding a polypeptide. In some embodiments, there are no more than 1, 2, 3, 4, 5, 6, 7, 8, 9, 10, 100, 200, 300, 400, 500, 600, 700, 800, 900, 1000, 2000, 3000, 4000 or 5000 nucleotides between the WXRE sequence and the promoter or between the WXRE sequence and the polynucleotide encoding a polypeptide. In some embodiments, the one or more additional regulatory elements are located between the promoter and the sequence encoding a polypeptide.

In some embodiments, the use of the transcription regulatory element (WXRE) listed in the present disclosure can enable a heterologous protein to still maintain its biological activity while the expression level is greatly increased (e.g., by at least 1, 2, 3, 4, 5, 6, 7, 8, 9, 10, 15, 20, 25, or 30 folds).

In some embodiments, the transcription regulatory element (WXRE) listed in the present disclosure can be used together with other regulatory elements as a whole, and maintains its biological activity while enabling the expression level of the heterologous protein to increase greatly.

Thus, in one aspect, the disclosure is related to an isolated polynucleotide molecule comprising a nucleotide sequence selected from the group consisting of (i) to (iv): (i) a sequence of any of SEQ ID NOs: 35-46; (ii) a reverse complementary sequence of the sequence of any of SEQ ID NOs: 35-46; (iii) a reverse complementary sequence of a sequence capable of hybridizing with the sequence of (i) or (ii) under a high stringency hybridization condition or a very high stringency hybridization condition; and (iv) a sequence having at least 80% sequence identity, or at least 90% sequence identity, alternatively at least 95% sequence identity, preferably at least 97% sequence identity, more preferably at least 98% sequence identity, most preferably at least 99% sequence identity with the sequence of (i) or (ii).

Various WXRE sequences and the methods of use thereof are described e.g., in WO2020/034097A1 and WO2020/034986A1, which are incorporated herein by reference in the entirety.

In some embodiments of the present disclosure, the WXRE sequence can be inserted into two vectors. They can be the same or different, and may have forward direction or reverse direction. The exemplary combinations of WXREs in two vectors are listed in Table 2.

TABLE 2

| Exemplary combinations of WXREs in two vectors | | |
|---|---|---|
| # | WXRE in a first vector | WXRE in a second vector |
| 1 | SEQ ID NO: 35 | SEQ ID NO: 35 |
| 2 | SEQ ID NO: 35 | SEQ ID NO: 36 |
| 3 | SEQ ID NO: 35 | SEQ ID NO: 37 |
| 4 | SEQ ID NO: 35 | SEQ ID NO: 38 |
| 5 | SEQ ID NO: 35 | SEQ ID NO: 39 |
| 6 | SEQ ID NO: 35 | SEQ ID NO: 40 |
| 7 | SEQ ID NO: 35 | SEQ ID NO: 41 |
| 8 | SEQ ID NO: 35 | SEQ ID NO: 47 |

TABLE 2-continued

Exemplary combinations
of WXREs in two vectors

| # | WXRE in a first vector | WXRE in a second vector |
|---|---|---|
| 9 | SEQ ID NO: 35 | SEQ ID NO: 48 |
| 10 | SEQ ID NO: 35 | SEQ ID NO: 49 |
| 11 | SEQ ID NO: 35 | SEQ ID NO: 50 |
| 12 | SEQ ID NO: 35 | SEQ ID NO: 51 |
| 13 | SEQ ID NO: 35 | SEQ ID NO: 52 |
| 14 | SEQ ID NO: 35 | SEQ ID NO: 53 |
| 15 | SEQ ID NO: 35 | SEQ ID NO: 42 |
| 16 | SEQ ID NO: 35 | SEQ ID NO: 43 |
| 17 | SEQ ID NO: 35 | SEQ ID NO: 44 |
| 18 | SEQ ID NO: 35 | SEQ ID NO: 45 |
| 19 | SEQ ID NO: 35 | SEQ ID NO: 54 |
| 20 | SEQ ID NO: 35 | SEQ ID NO: 55 |
| 21 | SEQ ID NO: 35 | SEQ ID NO: 56 |
| 22 | SEQ ID NO: 35 | SEQ ID NO: 57 |
| 23 | SEQ ID NO: 36 | SEQ ID NO: 36 |
| 24 | SEQ ID NO: 36 | SEQ ID NO: 37 |
| 25 | SEQ ID NO: 36 | SEQ ID NO: 38 |
| 26 | SEQ ID NO: 36 | SEQ ID NO: 39 |
| 27 | SEQ ID NO: 36 | SEQ ID NO: 40 |
| 28 | SEQ ID NO: 36 | SEQ ID NO: 41 |
| 29 | SEQ ID NO: 36 | SEQ ID NO: 47 |
| 30 | SEQ ID NO: 36 | SEQ ID NO: 48 |
| 31 | SEQ ID NO: 36 | SEQ ID NO: 49 |
| 32 | SEQ ID NO: 36 | SEQ ID NO: 50 |
| 33 | SEQ ID NO: 36 | SEQ ID NO: 51 |
| 34 | SEQ ID NO: 36 | SEQ ID NO: 52 |
| 35 | SEQ ID NO: 36 | SEQ ID NO: 53 |
| 36 | SEQ ID NO: 36 | SEQ ID NO: 42 |
| 37 | SEQ ID NO: 36 | SEQ ID NO: 43 |
| 38 | SEQ ID NO: 36 | SEQ ID NO: 44 |
| 39 | SEQ ID NO: 36 | SEQ ID NO: 45 |
| 40 | SEQ ID NO: 36 | SEQ ID NO: 54 |
| 41 | SEQ ID NO: 36 | SEQ ID NO: 55 |
| 42 | SEQ ID NO: 36 | SEQ ID NO: 56 |
| 43 | SEQ ID NO: 36 | SEQ ID NO: 57 |
| 44 | SEQ ID NO: 37 | SEQ ID NO: 37 |
| 45 | SEQ ID NO: 37 | SEQ ID NO: 38 |
| 46 | SEQ ID NO: 37 | SEQ ID NO: 39 |
| 47 | SEQ ID NO: 37 | SEQ ID NO: 40 |
| 48 | SEQ ID NO: 37 | SEQ ID NO: 41 |
| 49 | SEQ ID NO: 37 | SEQ ID NO: 47 |
| 50 | SEQ ID NO: 37 | SEQ ID NO: 48 |
| 51 | SEQ ID NO: 37 | SEQ ID NO: 49 |
| 52 | SEQ ID NO: 37 | SEQ ID NO: 50 |
| 53 | SEQ ID NO: 37 | SEQ ID NO: 51 |
| 54 | SEQ ID NO: 37 | SEQ ID NO: 52 |
| 55 | SEQ ID NO: 37 | SEQ ID NO: 53 |
| 56 | SEQ ID NO: 37 | SEQ ID NO: 42 |
| 57 | SEQ ID NO: 37 | SEQ ID NO: 43 |
| 58 | SEQ ID NO: 37 | SEQ ID NO: 44 |
| 59 | SEQ ID NO: 37 | SEQ ID NO: 45 |
| 60 | SEQ ID NO: 37 | SEQ ID NO: 54 |
| 61 | SEQ ID NO: 37 | SEQ ID NO: 55 |
| 62 | SEQ ID NO: 37 | SEQ ID NO: 56 |
| 63 | SEQ ID NO: 37 | SEQ ID NO: 57 |
| 64 | SEQ ID NO: 38 | SEQ ID NO: 38 |
| 65 | SEQ ID NO: 38 | SEQ ID NO: 39 |
| 66 | SEQ ID NO: 38 | SEQ ID NO: 40 |
| 67 | SEQ ID NO: 38 | SEQ ID NO: 41 |
| 68 | SEQ ID NO: 38 | SEQ ID NO: 47 |
| 69 | SEQ ID NO: 38 | SEQ ID NO: 48 |
| 70 | SEQ ID NO: 38 | SEQ ID NO: 49 |
| 71 | SEQ ID NO: 38 | SEQ ID NO: 50 |
| 72 | SEQ ID NO: 38 | SEQ ID NO: 51 |
| 73 | SEQ ID NO: 38 | SEQ ID NO: 52 |
| 74 | SEQ ID NO: 38 | SEQ ID NO: 53 |
| 75 | SEQ ID NO: 38 | SEQ ID NO: 42 |
| 76 | SEQ ID NO: 38 | SEQ ID NO: 43 |
| 77 | SEQ ID NO: 38 | SEQ ID NO: 44 |
| 78 | SEQ ID NO: 38 | SEQ ID NO: 45 |
| 79 | SEQ ID NO: 38 | SEQ ID NO: 54 |
| 80 | SEQ ID NO: 38 | SEQ ID NO: 55 |
| 81 | SEQ ID NO: 38 | SEQ ID NO: 56 |
| 82 | SEQ ID NO: 38 | SEQ ID NO: 57 |

TABLE 2-continued

Exemplary combinations
of WXREs in two vectors

| # | WXRE in a first vector | WXRE in a second vector |
|---|---|---|
| 83 | SEQ ID NO: 39 | SEQ ID NO: 39 |
| 84 | SEQ ID NO: 39 | SEQ ID NO: 40 |
| 85 | SEQ ID NO: 39 | SEQ ID NO: 41 |
| 86 | SEQ ID NO: 39 | SEQ ID NO: 47 |
| 87 | SEQ ID NO: 39 | SEQ ID NO: 48 |
| 88 | SEQ ID NO: 39 | SEQ ID NO: 49 |
| 89 | SEQ ID NO: 39 | SEQ ID NO: 50 |
| 90 | SEQ ID NO: 39 | SEQ ID NO: 51 |
| 91 | SEQ ID NO: 39 | SEQ ID NO: 52 |
| 92 | SEQ ID NO: 39 | SEQ ID NO: 53 |
| 93 | SEQ ID NO: 39 | SEQ ID NO: 42 |
| 94 | SEQ ID NO: 39 | SEQ ID NO: 43 |
| 95 | SEQ ID NO: 39 | SEQ ID NO: 44 |
| 96 | SEQ ID NO: 39 | SEQ ID NO: 45 |
| 97 | SEQ ID NO: 39 | SEQ ID NO: 54 |
| 98 | SEQ ID NO: 39 | SEQ ID NO: 55 |
| 99 | SEQ ID NO: 39 | SEQ ID NO: 56 |
| 100 | SEQ ID NO: 39 | SEQ ID NO: 57 |
| 101 | SEQ ID NO: 40 | SEQ ID NO: 40 |
| 102 | SEQ ID NO: 40 | SEQ ID NO: 41 |
| 103 | SEQ ID NO: 40 | SEQ ID NO: 47 |
| 104 | SEQ ID NO: 40 | SEQ ID NO: 48 |
| 105 | SEQ ID NO: 40 | SEQ ID NO: 49 |
| 106 | SEQ ID NO: 40 | SEQ ID NO: 50 |
| 107 | SEQ ID NO: 40 | SEQ ID NO: 51 |
| 108 | SEQ ID NO: 40 | SEQ ID NO: 52 |
| 109 | SEQ ID NO: 40 | SEQ ID NO: 53 |
| 110 | SEQ ID NO: 40 | SEQ ID NO: 42 |
| 111 | SEQ ID NO: 40 | SEQ ID NO: 43 |
| 112 | SEQ ID NO: 40 | SEQ ID NO: 44 |
| 113 | SEQ ID NO: 40 | SEQ ID NO: 45 |
| 114 | SEQ ID NO: 40 | SEQ ID NO: 54 |
| 115 | SEQ ID NO: 40 | SEQ ID NO: 55 |
| 116 | SEQ ID NO: 40 | SEQ ID NO: 56 |
| 117 | SEQ ID NO: 40 | SEQ ID NO: 57 |
| 118 | SEQ ID NO: 41 | SEQ ID NO: 41 |
| 119 | SEQ ID NO: 41 | SEQ ID NO: 47 |
| 120 | SEQ ID NO: 41 | SEQ ID NO: 48 |
| 121 | SEQ ID NO: 41 | SEQ ID NO: 49 |
| 122 | SEQ ID NO: 41 | SEQ ID NO: 50 |
| 123 | SEQ ID NO: 41 | SEQ ID NO: 51 |
| 124 | SEQ ID NO: 41 | SEQ ID NO: 52 |
| 125 | SEQ ID NO: 41 | SEQ ID NO: 53 |
| 126 | SEQ ID NO: 41 | SEQ ID NO: 42 |
| 127 | SEQ ID NO: 41 | SEQ ID NO: 43 |
| 128 | SEQ ID NO: 41 | SEQ ID NO: 44 |
| 129 | SEQ ID NO: 41 | SEQ ID NO: 45 |
| 130 | SEQ ID NO: 41 | SEQ ID NO: 54 |
| 131 | SEQ ID NO: 41 | SEQ ID NO: 55 |
| 132 | SEQ ID NO: 41 | SEQ ID NO: 56 |
| 133 | SEQ ID NO: 41 | SEQ ID NO: 57 |
| 134 | SEQ ID NO: 47 | SEQ ID NO: 47 |
| 135 | SEQ ID NO: 47 | SEQ ID NO: 48 |
| 136 | SEQ ID NO: 47 | SEQ ID NO: 49 |
| 137 | SEQ ID NO: 47 | SEQ ID NO: 50 |
| 138 | SEQ ID NO: 47 | SEQ ID NO: 51 |
| 139 | SEQ ID NO: 47 | SEQ ID NO: 52 |
| 140 | SEQ ID NO: 47 | SEQ ID NO: 53 |
| 141 | SEQ ID NO: 47 | SEQ ID NO: 42 |
| 142 | SEQ ID NO: 47 | SEQ ID NO: 43 |
| 143 | SEQ ID NO: 47 | SEQ ID NO: 44 |
| 144 | SEQ ID NO: 47 | SEQ ID NO: 45 |
| 145 | SEQ ID NO: 47 | SEQ ID NO: 54 |
| 146 | SEQ ID NO: 47 | SEQ ID NO: 55 |
| 147 | SEQ ID NO: 47 | SEQ ID NO: 56 |
| 148 | SEQ ID NO: 47 | SEQ ID NO: 57 |
| 149 | SEQ ID NO: 48 | SEQ ID NO: 48 |
| 150 | SEQ ID NO: 48 | SEQ ID NO: 49 |
| 151 | SEQ ID NO: 48 | SEQ ID NO: 50 |
| 152 | SEQ ID NO: 48 | SEQ ID NO: 51 |
| 153 | SEQ ID NO: 48 | SEQ ID NO: 52 |
| 154 | SEQ ID NO: 48 | SEQ ID NO: 53 |
| 155 | SEQ ID NO: 48 | SEQ ID NO: 42 |
| 156 | SEQ ID NO: 48 | SEQ ID NO: 43 |

TABLE 2-continued

Exemplary combinations
of WXREs in two vectors

| # | WXRE in a first vector | WXRE in a second vector |
|---|---|---|
| 157 | SEQ ID NO: 48 | SEQ ID NO: 44 |
| 158 | SEQ ID NO: 48 | SEQ ID NO: 45 |
| 159 | SEQ ID NO: 48 | SEQ ID NO: 54 |
| 160 | SEQ ID NO: 48 | SEQ ID NO: 55 |
| 161 | SEQ ID NO: 48 | SEQ ID NO: 56 |
| 162 | SEQ ID NO: 48 | SEQ ID NO: 57 |
| 163 | SEQ ID NO: 49 | SEQ ID NO: 49 |
| 164 | SEQ ID NO: 49 | SEQ ID NO: 50 |
| 165 | SEQ ID NO: 49 | SEQ ID NO: 51 |
| 166 | SEQ ID NO: 49 | SEQ ID NO: 52 |
| 167 | SEQ ID NO: 49 | SEQ ID NO: 53 |
| 168 | SEQ ID NO: 49 | SEQ ID NO: 42 |
| 169 | SEQ ID NO: 49 | SEQ ID NO: 43 |
| 170 | SEQ ID NO: 49 | SEQ ID NO: 44 |
| 171 | SEQ ID NO: 49 | SEQ ID NO: 45 |
| 172 | SEQ ID NO: 49 | SEQ ID NO: 54 |
| 173 | SEQ ID NO: 49 | SEQ ID NO: 55 |
| 174 | SEQ ID NO: 49 | SEQ ID NO: 56 |
| 175 | SEQ ID NO: 49 | SEQ ID NO: 57 |
| 176 | SEQ ID NO: 50 | SEQ ID NO: 50 |
| 177 | SEQ ID NO: 50 | SEQ ID NO: 51 |
| 178 | SEQ ID NO: 50 | SEQ ID NO: 52 |
| 179 | SEQ ID NO: 50 | SEQ ID NO: 53 |
| 180 | SEQ ID NO: 50 | SEQ ID NO: 42 |
| 181 | SEQ ID NO: 50 | SEQ ID NO: 43 |
| 182 | SEQ ID NO: 50 | SEQ ID NO: 44 |
| 183 | SEQ ID NO: 50 | SEQ ID NO: 45 |
| 184 | SEQ ID NO: 50 | SEQ ID NO: 54 |
| 185 | SEQ ID NO: 50 | SEQ ID NO: 55 |
| 186 | SEQ ID NO: 50 | SEQ ID NO: 56 |
| 187 | SEQ ID NO: 50 | SEQ ID NO: 57 |
| 188 | SEQ ID NO: 51 | SEQ ID NO: 51 |
| 189 | SEQ ID NO: 51 | SEQ ID NO: 52 |
| 190 | SEQ ID NO: 51 | SEQ ID NO: 53 |
| 191 | SEQ ID NO: 51 | SEQ ID NO: 42 |
| 192 | SEQ ID NO: 51 | SEQ ID NO: 43 |
| 193 | SEQ ID NO: 51 | SEQ ID NO: 44 |
| 194 | SEQ ID NO: 51 | SEQ ID NO: 45 |
| 195 | SEQ ID NO: 51 | SEQ ID NO: 54 |
| 196 | SEQ ID NO: 51 | SEQ ID NO: 55 |
| 197 | SEQ ID NO: 51 | SEQ ID NO: 56 |
| 198 | SEQ ID NO: 51 | SEQ ID NO: 57 |
| 199 | SEQ ID NO: 52 | SEQ ID NO: 52 |
| 200 | SEQ ID NO: 52 | SEQ ID NO: 53 |
| 201 | SEQ ID NO: 52 | SEQ ID NO: 42 |
| 202 | SEQ ID NO: 52 | SEQ ID NO: 43 |
| 203 | SEQ ID NO: 52 | SEQ ID NO: 44 |
| 204 | SEQ ID NO: 52 | SEQ ID NO: 45 |
| 205 | SEQ ID NO: 52 | SEQ ID NO: 54 |
| 206 | SEQ ID NO: 52 | SEQ ID NO: 55 |
| 207 | SEQ ID NO: 52 | SEQ ID NO: 56 |
| 208 | SEQ ID NO: 52 | SEQ ID NO: 57 |
| 209 | SEQ ID NO: 53 | SEQ ID NO: 53 |
| 210 | SEQ ID NO: 53 | SEQ ID NO: 42 |
| 211 | SEQ ID NO: 53 | SEQ ID NO: 43 |
| 212 | SEQ ID NO: 53 | SEQ ID NO: 44 |
| 213 | SEQ ID NO: 53 | SEQ ID NO: 45 |
| 214 | SEQ ID NO: 53 | SEQ ID NO: 54 |
| 215 | SEQ ID NO: 53 | SEQ ID NO: 55 |
| 216 | SEQ ID NO: 53 | SEQ ID NO: 56 |
| 217 | SEQ ID NO: 53 | SEQ ID NO: 57 |
| 218 | SEQ ID NO: 42 | SEQ ID NO: 42 |
| 219 | SEQ ID NO: 42 | SEQ ID NO: 43 |
| 220 | SEQ ID NO: 42 | SEQ ID NO: 44 |
| 221 | SEQ ID NO: 42 | SEQ ID NO: 45 |
| 222 | SEQ ID NO: 42 | SEQ ID NO: 54 |
| 223 | SEQ ID NO: 42 | SEQ ID NO: 55 |
| 224 | SEQ ID NO: 42 | SEQ ID NO: 56 |
| 225 | SEQ ID NO: 42 | SEQ ID NO: 57 |
| 226 | SEQ ID NO: 43 | SEQ ID NO: 43 |
| 227 | SEQ ID NO: 43 | SEQ ID NO: 44 |
| 228 | SEQ ID NO: 43 | SEQ ID NO: 45 |
| 229 | SEQ ID NO: 43 | SEQ ID NO: 54 |
| 230 | SEQ ID NO: 43 | SEQ ID NO: 55 |
| 231 | SEQ ID NO: 43 | SEQ ID NO: 56 |
| 232 | SEQ ID NO: 43 | SEQ ID NO: 57 |
| 233 | SEQ ID NO: 44 | SEQ ID NO: 44 |
| 234 | SEQ ID NO: 44 | SEQ ID NO: 45 |
| 235 | SEQ ID NO: 44 | SEQ ID NO: 54 |
| 236 | SEQ ID NO: 44 | SEQ ID NO: 55 |
| 237 | SEQ ID NO: 44 | SEQ ID NO: 56 |
| 238 | SEQ ID NO: 44 | SEQ ID NO: 57 |
| 239 | SEQ ID NO: 45 | SEQ ID NO: 45 |
| 240 | SEQ ID NO: 45 | SEQ ID NO: 54 |
| 241 | SEQ ID NO: 45 | SEQ ID NO: 55 |
| 242 | SEQ ID NO: 45 | SEQ ID NO: 56 |
| 243 | SEQ ID NO: 45 | SEQ ID NO: 57 |
| 244 | SEQ ID NO: 54 | SEQ ID NO: 54 |
| 245 | SEQ ID NO: 54 | SEQ ID NO: 55 |
| 246 | SEQ ID NO: 54 | SEQ ID NO: 56 |
| 247 | SEQ ID NO: 54 | SEQ ID NO: 57 |
| 248 | SEQ ID NO: 55 | SEQ ID NO: 55 |
| 249 | SEQ ID NO: 55 | SEQ ID NO: 56 |
| 250 | SEQ ID NO: 55 | SEQ ID NO: 57 |
| 251 | SEQ ID NO: 56 | SEQ ID NO: 56 |
| 252 | SEQ ID NO: 56 | SEQ ID NO: 57 |
| 253 | SEQ ID NO: 57 | SEQ ID NO: 57 |

Expression System

The present disclosure provides an efficient protein expression system that utilizes piggyBac transposons and/or one or more regulatory elements as described herein. As used herein, the term "protein expression system" or "expression system" refers to a system comprising a host and a vector containing a heterologous sequence (e.g., exogenous gene), and the expression of the heterologous sequence in the host can be achieved by this system. The protein expression system generally comprises the following parts: (1) a host, i.e., an organism expressing proteins, which can be selected from bacteria, yeast, plant cells, animal cells, and the like; (2) one or more vectors. The type of the vector matches with the host. According to the different hosts, the vectors can be prokaryotic (bacterial) expression vectors, yeast expression vectors, plant expression vectors, mammalian expression vectors, insect expression vectors, and the like. The vector contains a fragment of a heterologous gene. The heterologous gene can be expressed in the host via the mediation of the vector. In some embodiments, the expressed protein products are secreted. In some embodiments, the vectors are integrated into host cell DNA.

A vector can be a delivery vehicle for a polynucleotide. In some embodiments, the vector includes a polynucleotide sequence encoding a certain protein operatively inserted therein and allows the expression of this protein in a genetic engineering recombinant technique. The vector can be used to transform, transduce or transfect a host cell. The vector in the present disclosure can be any suitable vector, which includes chromosomal, non-chromosomal and synthetic nucleic acid vectors (including a group of suitable nucleic acid sequences which express the various elements). For example, a vector can be a recombinant plasmid vector, a recombinant eukaryotic viral vector, a recombinant phage vector, a recombinant yeast minichromosome vector, a recombinant bacterial artificial chromosome vector, or a recombinant yeast plasmid vector.

In some embodiments, the vector in the present disclosure can include the derivatives of SV40, bacterial plasmids, phage DNAs, baculovirus, yeast plasmid, vectors derived from a combination of a plasmid and a phase DNA, and vectors such as virus nuclear acids (RNA or DNA). In some embodiments, the vector is an adeno-associated virus (AAV) vector.

As used herein, the term "host cell" in the present disclosure refers to a cell that receives a heterologous polynucleotide and/or a vector introduced therein. The host cell can be a eukaryotic host cell or a prokaryotic host cell, wherein the eukaryotic host cell can be a mammalian host cell, an insect host cell, a plant host cell, a fungal host cell, a eukaryotic algae host cell, a nematode host cell, a protozoan host cell, and a fish host cell. Illustratively, the host cell in the present disclosure is a eukaryotic host cell, e.g., a mammalian host cell. In some embodiments, the mammalian host cell is a Chinese hamster ovary (CHO) cell, a COS cell, a Vero cell, a SP2/0 cell, a NS/O myeloma cell, an immature hamster kidney cell, a HeLa cell, a human B cell, a cv-1/ EBNA cell, an L cell, a 3T3 cell, a HEPG2 cell, a PerC6 cell, a human embryonic kidney 293 (HEK 293) cell, or an MDCK cell. In some embodiments, the cell is a human embryonic retinal cell (PER.C6) with the transforming early region (E1) of adenovirus type 5 (ad5). CHO cells are routinely used for the production of biopharmaceutical proteins. In some embodiments, CHO cell is a CHO-K1 cell, a CHO-DG44 cell, or a CHO-S cell. In a preferred embodiment, the CHO cell is a CHO-K1 cell.

A key step in protein expression is the selection of recombinant host cells which have been successfully transfected with the vector comprising the heterologous gene coding the protein of interest. Most commonly a selection marker is included in the vector. The selection marker can be a gene or DNA sequence that allows separation of recombinant host cells containing the marker and those not containing it. The combination of a selection marker and a selection medium allows growth of recombinant host cells that have been transfected with the vector, while in some embodiments, inhibiting the growth of host cells that have not been successfully transfected.

Antibiotic resistance genes are the most commonly used markers for recombinant host cell selection. An antibiotic resistance gene as a selection marker, in combination with a selection medium containing the antibiotic, can be used in order to achieve selection. Exemplary antibiotic selection markers include but are not limited to ampicillin resistance gene, chloramphenicol resistance gene, kanamycin resistance gene, tetracycline resistance gene, polymyxin B resistance gene, erythromycin resistance gene, carbenicillin resistance gene, streptomycin resistance gene, spectinomycin resistance gene, blasticidin resistance gene, neomycin resistance gene, puromycin resistance gene, zeocin resistance gene, and hygromycin B resistance gene. Accordingly, the selection antibiotics include but are not limited to ampicillin, chloramphenicol, kanamycin, tetracycline, polymyxin B, erythromycin, carbenicillin, streptomycin, spectinomycin, blasticidin, neomycin, puromycin, zeocin, and hygromycin B. In some embodiments, the selection marker is blasticidin resistance gene. In some embodiments, the selection marker is zeocin resistance gene.

In some embodiment, the selection medium can comprises one or more of the following ingredients: serum, polysaccharide (e.g. glucose, and/or dextrose), sodium pyruvate, glutathione, ethanolamine, amino acid (e.g. glycine, alanine, arginine, asparagine, aspartic acid, cysteine, glutamic acid, histidine, isoleucine, leucine, lysine, glutamine, methionine, phenylalanine, proline, serine, threonine, tryptophan, tyrosine, and/or valine) or a salt thereof, vitamin (e.g. ascorbic acid phosphate, choline chloride, D-calcium pantothenate, folic acid, niacinamide, pyridoxine hydrochloride, riboflavin, thiamine hydrochloride, and/or i-inositol), inorganic salt (e.g. calcium chloride, ferric nitrate, magnesium sulfate, potassium chloride, sodium bicarbonate, sodium chloride, and/or sodium phosphate dibasic), protein (e.g. human transferrin and/or recombinant insulin), and/or trace element (e.g. ammonium metavanadate, cupric sulfate, manganous chloride, and/or sodium selenite).

The expression system can be used to express various proteins or polypeptides, e.g., an antibody, a fusion protein, an enzyme, a soluble protein, a membrane protein, a structural protein, a ribosome protein, a zymogen, a cell surface receptor protein, a transcriptional regulatory protein, a translational regulatory protein, a chromatin protein, a hormone, a cell cycle regulatory protein, a G protein, a neuroactive peptide, an immunomodulatory protein, a blood component protein, an ion gate protein, a heat shock protein, dihydrofolate reductase, an antibiotic resistance protein, a functional fragment of any one of the proteins, an epitope fragment of any one of the proteins, and any combination thereof.

As used herein, the term "antibody" in the present disclosure refers to an immunoglobulin, a fragment thereof, or a derivative of them, and includes any polypeptide comprising an antigen-binding site, regardless of whether it is produced in vitro or in vivo. This term includes, but is not limited to, a polyclonal antibody, a monoclonal antibody, a monospecific antibody, a bispecific antibody, a trispecific antibody, a multispecific antibody, a non-specific antibody, a humanized antibody, a fully human antibody, a chimeric antibody, a single-domain antibody, a single-stranded antibody, a synthetic antibody, a recombinant antibody, a heterozygous antibody, a mutated antibody, and a grafted antibody. The term "antibody" also includes antibody fragments such as Fab, Fab', F(ab')$_2$, Fv, scFv, Fd, dAb, and other antibody fragments that retain the antigen-binding function. Typically, such fragments will include an antigen-binding fragment.

As used herein, the term "fusion protein" in the present disclosure refers to a molecule comprising two or more proteins or the fragments thereof which are linked by the covalent bond via their respective main chains of the peptides, and more preferably, the fusion protein is generated by the genetic expression of the polynucleotide molecules encoding these proteins. In some embodiments, the fusion protein comprises an immunoglobulin domain. In some embodiments, the fusion protein is an Fc-fusion protein.

In some embodiments, the antibodies that can be used in connection with the expression system include, e.g., Adalimumab, Bezlotoxumab, Avelumab, Dupilumab, Durvalumab, Ocrelizumab, Brodalumab, Reslizumab, Olaratumab, Daratumumab, Elotuzumab, Necitumumab, Infliximab, Obiltoxaximab, Atezolizumab, Secukinumab, Mepolizumab, Nivolumab, Alirocumab, Evolocumab, Dinutuximab, Bevacizumab, Pembrolizumab, Ramucirumab, Vedolizumab, Siltuximab, Alemtuzumab, Trastuzumab, Pertuzumab, Obinutuzumab, Brentuximab, Raxibacumab, Belimumab, Ipilimumab, Denosumab, Ofatumumab, Besilesomab, Tocilizumab, Canakinumab, Golimumab, Ustekinumab, Certolizumab, Catumaxomab, Eculizumab, Ranibizumab, Panitumumab, Natalizumab, Omalizumab, Cetuximab, Efalizumab, Ibritumomab, Fanolesomab, Tositumomab, Gemtuzumab, Palivizumab, Necitumumab, Basiliximab, Rituximab, Capromab, Satumomab, and Muromonab.

In some embodiments, the fusion proteins that can be used in the present disclosure include, e.g., Etanercept, Alefacept, Abatacept, Rilonacept, Romiplostim, Belatacept, and Aflibercept.

In some embodiments, the expression system provides at least two transposon vectors. One transposon vector is designed to carry a sequence encoding a first polypeptide (e.g., an antibody heavy chain). The second transposon vector is designed to carry a sequence encoding a second polypeptide (e.g., an antibody light chain). In some embodiments, one singly transposon vector provides a sequence encoding two or more polypeptides. For example, the sequence encoding the antibody heavy chain and the sequence encoding the antibody light chain can be on the same transposon vector. They can be located in the same expression cassette or in different expression cassettes within the transposon vector.

In some embodiments, the transposon vector can comprise a sequence comprising or consisting of from 5' to 3' one or more of the following elements: TTAA, 5'-ITR, optionally a 5'-internal domain, a promoter, a gene of interest, a selection marker, optionally a 3'-internal domain, 3'-ITR, and TTAA. In some embodiments, the transposon vector can comprise a sequence comprising or consisting of from 5' to 3' one or more of the following elements: PB transposase 5'-recognition site, a promoter, a gene of interest, a selection marker, and PB transposase 3'-recognition site. In some embodiments, the sequence can further include one or two regulatory elements. The one or two regulatory elements can be located between the promoter and the gene of interest and/or between the gene of interest and the polyA signal sequence. Thus, in some embodiments, the transposon vector can comprise a sequence comprising or consisting of from 5' to 3' one or more of the following elements: TTAA, 5'-ITR, optionally a 5'-internal domain, a promoter, a regulatory element, a gene of interest, a regulatory element, a polyA signal sequence, a promoter for a selection marker, the selection marker, a polyA signal sequence for the selection marker, optionally a 3'-internal domain, 3'-ITR, and TTAA. In some embodiments, the transposon vector can comprise a sequence comprising or consisting of from 5' to 3' one or more of the following elements: PB transposase 5'-recognition site, a promoter, a regulatory element, a gene of interest, a regulatory element, a polyA signal sequence, a promoter for a selection marker, the selection marker, a polyA signal sequence for the selection marker, and PB transposase 3'-recognition site.

The gene of interest can actually include a sequence encoding two or more polypeptides (e.g., an antibody heavy chain and an antibody light chain). These sequences can separated from one another by sequences encoding a self-cleavage peptide (e.g., P2A or T2A) or a protease recognition site (e.g., furin). The open reading frame (ORF) thus encodes a single polyprotein, which, either during or after translation, can be cleaved into the individual proteins. Similarly, the transposase vector can have a sequence comprising or consisting of a promoter, a piggyBac transpose coding sequence, a polyA signal sequence. In some embodiments, the transposase vector further comprises a selection marker.

The expression of gene of interest can be further enhanced by WXRE transcription regulatory elements. In some embodiments, the transposon vector can comprise a sequence comprising or consisting of from 5' to 3' one or more of the following elements: TTAA, 5'-ITR, optionally a 5'-internal domain, a WXRE transcription regulatory element, a promoter, optionally the first intron of human EF-1α, a regulatory element, a gene of interest, a regulatory element, a polyA signal sequence, a promoter for a selection marker, the selection marker, a polyA signal sequence for the selection marker, optionally a 3'-internal domain, 3'-ITR, and TTAA. In some embodiments, the transposon vector can comprise a sequence comprising or consisting of from 5' to 3' one or more of the following elements: PB transposase 5'-recognition site, a WXRE transcription regulatory element, a promoter, optionally the first intron of human EF-1α, a regulatory element, a gene of interest, a regulatory element, a polyA signal sequence, a promoter for a selection marker, the selection marker, a polyA signal sequence for the selection marker, and PB transposase 5'-recognition site.

In some embodiments, the promotor is a CMV promotor In some embodiments, the CMV promoter has a sequence identity with the sequence as shown in SEQ ID: 59. In some embodiments, the sequence having sequence identity with the sequence as shown in SEQ ID: 59 has a sequence identity of at least 80%, 81%, 82%, 83%, 84%, 85%, 86%, 87%, 88%, 89%, 90%, 91%, 92%, 93%, 94%, 95%, 96%, 97%, 98%, 99%, or 100% (including all the ranges and percentages between these values) with the sequence as shown in SEQ ID: 59.

In some embodiments, the promoter is an inducible promoter. Inducible promoters include any promoter capable of increasing the amount of gene product produced, by a given gene, in response to exposure to an inducer. Thus the use of this construct allows for control of the expression of the target functional gene or transposase introduced into the host cell. Inducible promoters are known to those familiar with the art and a variety exists that can be used to drive expression. Inducible systems include, for example, the heat shock promoter system, the metallothionein system, the glucocorticoid system, tissue specific promoters, etc. Promoters regulated by heat shock, such as the promoter normally associated with the gene encoding the 70-kDa heat shock protein, can increase expression several-fold after exposure to elevated temperatures. The glucocorticoid system also functions well in triggering the expression of genes. The system consists of a gene encoding glucocorticoid receptor protein (GR) which in the presence of a steroid hormone (i.e. glucocorticoid or one of its synthetic equivalents such as dexamethasone) forms a complex with the hormone. This complex then binds to a short nucleotide sequence (26 bp) named the glucocorticoid response element (GRE), and this binding activates the expression of linked genes. Thus inducible promoters can be used as an environmentally inducible promoter for controlling the expression of the introduced gene.

In some embodiments, the inducible promoter is a T7 promoter. In some embodiments, the inducible promoter is PA1lacO1 promoter. In some embodiments, the inducible promoter is activated by an agent selected from a group that includes IPTG, sodium salicylate, octapine, nopaline, the quorum signal 3OC6HSL, aTc, cuminic acid, DAPG, and salicylic acid. In some embodiments, the inducible promoter has a terminator and the terminator is downstream from the inducible promoter. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system, the ecdysone insect promoter, the tetracycline-repressible system, the tetracycline-inducible system, and the rapamycin-inducible system.

The promoters can also be multicistronic (bicistronic or tricistronic). For example, in some embodiments, transcription units can be engineered as a bicistronic unit containing an IRES (internal ribosome entry site), which allows coexpression of gene products (e.g. encoding an antibody heavy chain and an antibody light chain) by a message from a single promoter. Alternatively, in some cases, a single promoter may direct expression of an RNA that contains, in a single open reading frame (ORF), two or three genes (e.g. encoding an alpha chain and/or beta chain of a TCR) separated from one another by sequences encoding a self-cleavage peptide (e.g., P2A or T2A) or a protease recognition site (e.g., furin). The ORF thus encodes a single polyprotein, which, either during (in the case of 2A e.g., T2A) or after translation, is cleaved into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream.

The first intron of human EF-1α can be used to increase the expression level. The first intron of human EF-1α can have a sequence that has a sequence identity with the sequence as shown in SEQ ID: 34. In some embodiments, the sequence having sequence identity with the sequence as shown in SEQ ID: 34 has a sequence identity of at least 80%, 81%, 82%, 83%, 84%, 85%, 86%, 87%, 88%, 89%, 90%, 91%, 92%, 93%, 94%, 95%, 96%, 97%, 98%, 99%, or 100% (including all the ranges and percentages between these values) with the sequence as shown in SEQ ID: 34 (the first intron of human EF-1α).

In some embodiments, the expression system as described herein can increase the expression amount of a heterologous protein by about or at least 1, 2, 3, 4, 5, 6, 7, 8, 9, 10, 15, 20, 30, 40, or 50 folds (e.g., as compared to a control expression system without the regulatory element sequences or the piggyBac transposon).

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, 600, 700, 800, 900, 1000, or 5000 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, 200, 500, or 1000 amino acid residues.

As used herein, the term "sequence identity" and the "percent identity" in the present disclosure refer to the percentage of the same (i.e., identical) nucleotides or amino acids between two or more polynucleotides or polypeptides. The sequence identity between two or more polynucleotides or polypeptides can be determined by the following method. The nucleotide sequences or the amino acid sequences of the polynucleotides or polypeptides are aligned and the number of positions containing the same nucleotide or amino acid residue in the aligned polynucleotides or polypeptides is scored and compared with the number of positions containing different nucleotides or amino acid residues in the aligned polynucleotides or polypeptides. The polynucleotides may differ at one position, for example, by containing different nucleotides (i.e., substitutions or mutations) or by the deletion of nucleotide(s) (i.e., the insertion of nucleotide(s) or the deletion of nucleotide(s) in one or two polynucleotides). The polypeptides may differ at one position, for example, by containing different amino acids (i.e., substitutions or mutations) or by the deletion of amino acid(s) (i.e., the insertion of amino acid(s) or the deletion of amino acid(s) in one or two polypeptides). The sequence identity can be calculated by dividing the number of positions containing the same nucleotide or amino acid residue by the total number of the amino acid residues in the polynucleotide or polypeptide. For example, the percent identity can be calculated by dividing the number of positions containing the same nucleotide or amino acid residue by the total number of the nucleotides or the amino acid residues in the polynucleotide or polypeptide. Thus, the percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished e.g., using a Blossum 62 scoring matrix with a gap penalty of 12, a gap extend penalty of 4, and a frameshift gap penalty of 5.

The present disclosure also provides a kit comprising the recombinant host cell as described herein, and/or a kit comprising the vectors or the expression system as described herein.

Methods of Using Expression System, Transposon Vectors, and Transposase Vectors

The present disclosure provides methods of using expression system, transposon vectors, and transposase vectors.

In one aspect, provided herein are methods of using the expression system to produce recombinant protein in host cells (e.g., Chinese hamster ovary (CHO) cells, CHO-K1 cells, or any cells that are commonly used for protein expression known in the art).

In some embodiments, an appropriate number of host cells (e.g., at least or about 1, 2, 3, 5, 6, 8, 9, 10, 20, 30, 40, 50, or 100 million) are transfected by an appropriate amount of transposon vectors (e.g., recombinant protein expressing plasmid) and the transposase vectors (e.g., transposase expressing plasmid). In some embodiments, the cell density is between 3.5 to 4.5 million cells/mL. In some embodiments, the host cells are transfected by a total of at least or about 1 μg of transposon vectors (e.g., at least or about 1 μg, 2 μg, 3 μg, 4 μg, 5 μg, 6 μg, 7 μg, 8 μg, 9 μg, 10 μg, 20 μg, 30 μg, 40 μg, 50 μg, or 100 μg).

In some embodiments, the transposon vectors (e.g., recombinant protein expressing plasmid) and the transposase vector (e.g., transposase expressing plasmids) used for transfection can have a mass ratio of about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1. Then, the transfected cells are resuspended in an appropriate volume (e.g., at least or about 1 mL, 2 mL, 3 mL, 4 mL, 5 mL, 6 mL, 7 mL, 8 mL, 9 mL, 10 mL, 15 mL, 20 mL, 30 mL, 40 mL, or 50 mL) of the host cell culture. The resulting solution can be mixed and incubated in a shaking incubator (e.g., a Kuhner® shaking incubator).

Many transformation or transfection techniques are available to introduce vectors into a cell. Electroporation is also a commonly-used method for introducing DNA into a cell. In this technique, cells are subject to electrical impulses of high field strength which reversibly permeabilizes biomembranes, allowing the entry of exogenous DNA sequences. In some embodiments, fertilized eggs are microinjected with the vectors. In some embodiments, PEI (polyetherimide) can be added to transduce the plasmids as described herein to the host cells (e.g., CHO-K1 cells). In some embodiments, the vectors can be microinjected directly into cells though the use of micropipettes. Alternatively, high velocity ballistics can be used to propel small DNA associated particles into the cell. In some embodiments, the cell is permeabilized by the presence of polyethylene glycol, thus allowing DNA to enter the cell through diffusion. DNA can also be introduced into a cell by fusing protoplasts with other carriers which contain DNA. These carriers include minicells, cells, lysosomes or other fusible lipid-surfaced bodies. The resulting cell culture can be incubated in an appropriate container (e.g., a spin tube) in an incubator (e.g., a shaking incubator).

After an appropriate time (e.g., at least or about 2 hours, 4 hours, 6 hours, 12 hours, 18 hours, 24 hours, 30 hours, 36 hours or longer) of transfection, an appropriate volume (e.g., at least or about 1 mL, 2 mL, 5 mL, 10 mL, 15 mL, or 20 mL) of fresh medium containing antibiotics for selection (e.g., blasticidin, geneticin (G-418), hygromycin B, mycophenolic acid, puromycin, zeocin) can be added to the transfected cell culture. The antibiotic reagent corresponds to the antibiotic resistance gene as decided herein. The concentration of antibiotics can be determined (e.g., by the killing curve experiment) on the native host cell (e.g., cells without modifications). In addition, the concentration of the replenishing medium can be the same or higher than the level of the normal antibiotic concentration for selection (e.g., at least or about 2 folds, 3 folds, 4 folds, 5 folds, or higher).

In some embodiments, cell passaging can be carried out (e.g., every day, every 2 days, every 3 days, every 4 days, every 5 days, or every 6 days) with the fresh medium containing the selected antibiotic reagent. The seeding density can be adjusted based on cell growth conditions (e.g., the viability rate, growth rate, and doubling time of the cells).

In some embodiments, after an appropriate time (approximately 1 week, approximately 2 weeks, approximately 3 weeks, approximately 4 weeks, approximately 5 weeks, or longer) of antibiotic selection, the cell culture can be used to inoculate the production basal medium at the about same seeding density as determined for each transfected cell culture, respectively. The production cell cultures can be incubated in a shaking incubator.

In some embodiments, the production process can be performed by fed-batch culturing. Appropriate type and amount of feeding medium can be supplemented to the culture accordingly.

In some aspects, the disclosure provides methods that are designed for quickly evaluating a heteromultimer (e.g., antibody) expression. For example, for efficient expression of antibodies, the antibody heavy chain and the antibody light chain needs to be expressed in roughly 1:1 ratio. If the concentration for a selection antibiotic is too low, the amount of functional vectors in the cells can be too small. If the concentration for a selection antibiotic is too high, it may create a condition that is not favorable for culturing cells. In some embodiments, the expression system in the present methods involve a pair of two vectors, one carrying a heterologous gene encoding an antibody heavy chain and the other carrying a heterologous gene encoding an antibody light chain. The selection marker in the two vectors might be different. In one embodiment, the selection marker in the first vector is blasticidin while the selection marker in the second vector is zeocin. The concentration of blasticidin and zeocin can be any concentrations as described herein. In some embodiments, the methods can also involve one vector comprising a heterologous gene encoding an antibody heavy chain and a heterologous gene encoding an antibody light chain. The ratio of the two vectors needs to be properly adjusted. It has been determined, based on tests on many different conditions, the methods provided herein can express antibodies with a high efficiency, and can be used to reliably evaluate the heteromultimer expression in a reasonably short time. Furthermore, the methods provided herein can express antibodies with a high expression level. Thus, in some embodiments, the methods involve transfecting the cell a pair of two transposon vectors, one carrying a heterologous gene encoding a first polypeptide and the other carrying a heterologous gene encoding a second polypeptide. Two selection markers are used. One selection marker is blasticidin resistance gene, and the other selection marker is zeocin resistance gene. In some embodiment, blasticidin is present in the selection medium in an amount of 1-15 µg/mL and zeocin is present in an amount of 50-1500 µg/mL. In some embodiments, after about 18~30 hours (e.g., about 24 hours) of transfection, the cells are cultured in an appropriate cell culture medium containing blasticidin (e.g., 9 µg/mL) and Zeocin (e.g., 400 µg/mL). The cells are then passaged to a new medium containing blasticidin and Zeocin every 2 to 4 days. When the cell viability is recovered to 90% or more, the expression level of the heteromultimer can be evaluated by fed-batch cultures. In some embodiments, the fed-batch cultures can be any medium as described herein. In some embodiments, the fed-batch cultures contain blasticidin and Zeocin.

The present disclosure also provides methods of making a transgenic animal. In one aspect, the methods involve introducing ex vivo into a non-human vertebrate embryo or fertilized oocyte a nucleic acid comprising a transposon vector as described herein, and, within the same or on a separate vector, a nucleotide sequence encoding a transposase as described herein. The resultant non-human vertebrate embryo or fertilized oocyte can be selected and then implanted into a foster mother of the same species under conditions favoring development of the embryo into a transgenic non-human vertebrate. The embryo can then develop into a transgenic non-human vertebrate, thereby generating a transgenic non-human vertebrate comprising an exogenous nucleotide sequence.

Many selection markers can be used, include, for example, genes that provide antibiotic, pesticide, insecticide, herbicide resistance; genes that modify the physiology of the host, such as for example eye color or green fluorescent protein, to produce an altered visible phenotype; etc. The inserted DNA is integrated in the genome and can be stably passed to the subsequent progenies. In some embodiments, cross-breeding is performed to generate a heterozygous or homozygous transgenic animal with the inserted sequence.

In some embodiments, the animal is a cow, cat, dog, horse, sheep, mouse, rat, guinea pig, hamster, mink, panda, or pig. In some embodiments, the cell is of mammalian origin, and can be obtained from various animals described herein.

In one aspect, the disclosure is related to a method of preparing a recombinant host cell which stably expresses a protein, comprising a step of inserting into a host cell the vector as described herein. In some embodiments, the host cell is a Chinese hamster ovary (CHO) cell. In some embodiments, provided herein is the method that comprises a step of culturing the recombinant host cell as described herein under conditions that allow production of the protein.

In one aspect, the disclosure also provides a method for identifying a polypeptide having a desired property (e.g., binding specificity or functionality). The method involve generating a diverse collection of polynucleotides, preferably plasmid vectors or double stranded DNA PCR amplicons, encoding polypeptides having different properties, wherein said polynucleotides comprise a sequence coding for a polypeptide disposed between ITR sequences that are recognized by and functional with a least one transposase enzyme. The diverse collection of polynucleotides are then introduced into host cells. At least one transposase enzyme functional with said inverted terminal repeat sequences is expressed in the host cells so that the diverse collection of polynucleotides are integrated into the host cell genome to provide a host cell population that expresses said diverse collection of polynucleotides encoding polypeptides having different properties. The host cells are then screened to identify a host cell expressing a polypeptide having a desired property (e.g., binding specificity or functionality). The inserted sequence is then determined from the host cell.

In one aspect, the disclosure is related to a kit comprising the recombinant host cell as described herein, a method of using the recombinant host cell as described herein in the preparation of a reagent or a kit for detecting a disease due to the abnormality of protein expression. In one aspect, the disclosure also provides a method of using the recombinant host cell as described herein in the preparation of a pharmaceutical composition for treating or preventing a disease. Also provided herein are pharmaceutical compositions that contain at least one (e.g., one, two, three, or four) of the proteins (e.g., antibodies or antigen-binding fragments) described herein. The pharmaceutical compositions may be formulated in any manner known in the art.

EXAMPLES

The invention is further described in the following examples, which do not limit the scope of the invention described in the claims.

Figure 9:
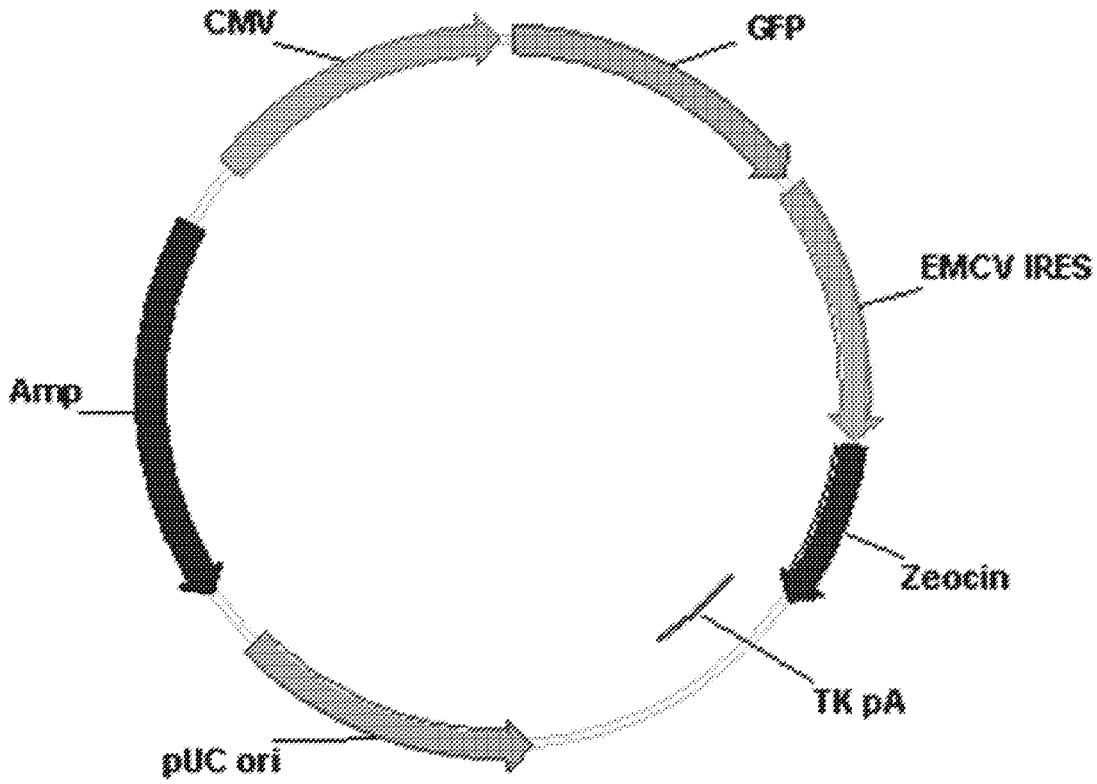
FIG. 9 illustrates a schematic diagram of a GFP-expressing vector without WXRE inserted therein.

Example 1: Construction of a Vector Library and Construction of a Stable Pool which Expresses Green Fluorescent Protein 1.1 Preparation of a Vector Library Containing a Genomic Fragment of Chinese Hamster Ovary Cells 1.1.1 1 μg of the GFP-expressing vector (i.e., the vector as shown in FIG. 9) was subjected to enzyme digestion with BamHI in the enzyme digestion kit (NEB) containing the restriction endonuclease BamHI so as to be linearized and stayed overnight at 37° C. (the composition and the contents of the reagents in the enzyme digestion reaction were as shown in Table 3), wherein BamHI could be replaced with any other endonucleases corresponding to a specific restriction site which existed in the upstream of a promoter corresponding to GFP.

The schematic diagram of the GFP-expressing vector was as shown in FIG. 9.

TABLE 3

| Composition and contents of the reagents in the enzyme digestion reaction | |
| --- | --- |
| Reaction components | Volume |
| NEB CutSmart Buffer (Cat# B7204S) | 5 μL |
| BamHI | 5 μL |
| GFP-expressing vector | 1 μg |
| Ultrapure water | up to a total volume of 50 μL |

1.1.2 Approximate five million CHO host cells were harvested, a DNeasy Blood & Tissue Kit (QIAGEN) was used to extract the genomic DNA of the CHO host cells, and said genomic DNA was dissolved in 100 μL of the elution buffer in the above-mentioned kit.

1.1.3 5 μg of the genomic DNA was subjected to enzyme digestion with 100 units of restriction endonuclease BglII (NEB) or DpnII (NEB) (the composition and the contents of the reagents in the enzyme digestion reaction were as shown in Table 4). Other restriction endonucleases might also be used, as long as they matched with the cohesive end of the endonuclease of the linearized vector in step 1.1.1.

TABLE 4

| Composition and contents of the reagents in the enzyme digestion reaction | |
| --- | --- |
| Reaction components | Volume |
| NEB CutSmart Buffer (Cat# B7204S) | 5 μL |
| BamHI | 5 μL |
| CHO genomic DNA | 1 μg |
| Ultrapure water | up to a total volume of 50 μL |

1.1.4 The linearized vector in 1.1.1 was treated with 2 units of calf intestinal alkaline phosphatase (NEB) at 37° C. for approximate 30 minutes. Other types of alkaline phosphatases could also be used.

1.1.5 The linearized GFP-expressing vector in 1.1.4 and the digested CHO genomic DNA in 1.1.3 were subjected to separation by agarose gel electrophoresis, respectively. The gel was cut to recover the fragments of the GFP-expressing vector and the 1-4 kb fragments of the digested genome, DNA was extracted from the agarose gel after electrophoresis using a QIAquick Gel Extraction Kit (QIAGEN).

1.1.6 The fragments of the GFP-expressing vector and the fragments of the genome recovered in 1.1.5 were subjected to ligation using a DNA Ligation Kit (Takara, Cat #6022) for 45 minutes at 16° C. (the composition and the contents of the reagents in the ligation reaction were as shown in Table 5).

TABLE 5

| Composition and contents of the reagents in the ligation reaction | |
| --- | --- |
| Reaction components | Volume |
| the recovered CHO genomic DNA | 4 μL |
| the recovered vector | 6 μL |
| Solution I | 20 μg |
| Ultrapure water | 10 μL |

1.1.7 10 µL of the ligation product obtained by 1.1.6 was taken, 100 µL of competent cells were added, placed in an ice bath for 30 minutes, thermally stimulated at 42° C. for 1 minute, and then placed on ice for 1 minute. 500 µL of fresh LB medium free of antibiotic was added to each tube of cells, and the cells were subjected to a 45-minute-recovery at 37° C. The step of plating was skipped and 500 mL of medium containing 100 mg/L of Ampicillin was added directly. The vector extraction was performed using a Plasmid Maxi Kit (QIAGEN). The extracted DNA was used as the vector library.

1.1.8 The vector library obtained in 1.1.7 was linearized using the restriction endonucleases of which the restriction sites were merely located in the prokaryotic region of the backbone of the vector (for example, PvuI (NEB)), and stayed overnight under the same reaction conditions as in 1.1.1 at 37° C. DNA was recovered by the phenol-chloroform method and used for transfection the next day.

1.2 Construction of the Stable Pool Expressing Green Fluorescent Protein 1.2.1 Approximate five million CHO host cells were centrifuged, and the supernatant was discarded. At the same time, 90 µL of SF Cell Line Solution and 20 µL of Supplement I in an Amaxa SF Cell Line 4D-Nucleofector Kit L (Lonza, Cat #VCA-1005) and 0.3 µg to 0.6 µg of the linearized vector library obtained by step 1.1.8 were mixed evenly, and the cells were resuspended with this mixed solution and transferred to an electroporation cuvette. The cells were subjected to transfection using a program corresponding to the respective host cells in a 4D-Nucleofector™ System electroporation instrument. The electroporated cells were resuspended with 5 mL of medium free of antibiotic and placed in a shaker at 37° C. for cultivation.

1.2.2 24 hours after the transfection, equal volume of selective medium containing antibiotic corresponding to the resistance gene in the vector was added in the cell culture medium for screening (in this experiment, the antibiotic was Zeocin (800 µg/mL)).

1.2.3 The cells were counted every 2 to 4 days. Cell passage was performed according to the growth situation of the cells, and screening was performed by using the selective medium with antibiotic corresponding to the resistance gene in the vector (in this experiment, the antibiotic was Zeocin (400 µg/mL)). Monoclonal screening was prepared when the cell viability recovered to 90% or more.

Example 2: Screening of a Clone Highly Expressing Green Fluorescent Protein 2.1 Single-Cell Sorting and Expansion 2.1.1 The cells in the recovered pool in step 1.2.3 of Example 1 with a higher GFP expression level (for example, the top 0.5% of the expression level) were sorted by a FACS AriaII flow cytometer into a 96-well plate for cultivation.

2.1.2 75% of the medium in the plate was changed every 2 to 4 days until the recovered cells were visible by naked eyes.

2.2 Screening for a Clone Highly Expressing GFP

The cells recovered in 2.1.2 were successively transferred into a new 96-well plate respectively, altogether about 300 clones (all the cells in each well were derived from one cell and were referred to as a clone herein). The expression level of GFP was determined by a FACS AriaII flow cytometer, and the clones whose detected intensities were among the top 10% were transferred to a 24-well plate for expansion.

Example 3: Screening, Identification and Verification of the Transcriptional Regulatory Element 3.1 Identification of a Candidate Sequence of the Transcriptional Regulatory Element 3.1.1 When the cells that were expanded in the 24-well plate in 2.2 substantially covered the bottom of the plate, a DNeasy Blood & Tissue Kit (QIAGEN) was used to extract the genome of each clone.

3.1.2 A forward primer and a reverse primer were respectively designed in the vector (about 200 bp away from the upstream and the downstream of the restriction site of BamHI, respectively), and the genomes extracted in 3.1.1 were successively subjected to PCR amplification, wherein the sequence of the forward primer of the PCR reaction was GCAAAAAAGGGAATAAGGGCGACACGG (SEQ ID NO: 69) and the sequence of the reverse primer of the PCR reaction was CATAGCCCATATATGGAGTTCCGCGTTA (SEQ ID NO: 70).

The reaction system of the above-mentioned PCR reaction was as shown in Table 6.

TABLE 6

| Reaction system of the PCR reaction | |
|---|---|
| Reaction components | Volume |
| 5X Q5 Reaction Buffer | 5 µL |
| 10 mM dNTPs | 0.5 µL |
| 10 µM forward primer | 1.25 µL |
| 10 µM reverse primer | 1.25 µL |
| genome | 1 µL |
| Q5 DNA Polymerase (Cat# M0491S) | 0.25 ul |
| Ultrapure water | 15.75 µL |

The reaction steps of the above-mentioned PCR reaction were as shown in Table 7.

TABLE 7

| Reaction steps of the PCR reaction | | |
|---|---|---|
| Temperature | Time | Number of Cycles |
| 98° C. | 1 min | 1 |
| 98° C. | 30s | 35 |
| 61° C. | 30s | |
| 68° C. | 5 min | |
| 68° C. | 10 min | 1 |

3.1.3 PCR products were subjected to separation by agarose gel electrophoresis, the gel was cut to recover the specific band(s) of 1 kb or more, and the QIAquick Gel Extraction Kit (QIAGEN) was used to extract DNA.

3.1.4 The recovered band(s) was sent for sequencing, and the sequences A~G of the candidate transcriptional regulatory elements were identified.

3.1.5 The sequences A~G of the transcriptional regulatory elements obtained by sequencing and identification were as follows, wherein the sequence of the transcriptional regulatory element A was the sequence as shown in SEQ ID NO: 35 (the reverse sequence of the transcriptional regulatory element A was the sequence as shown in SEQ ID NO: 47);

the sequence of the transcriptional regulatory element B was the sequence as shown in SEQ ID NO: 36 (the reverse sequence of the transcriptional regulatory element B was the sequence as shown in SEQ ID NO: 48);

the sequence of the transcriptional regulatory element C was the sequence as shown in SEQ ID NO: 37 (the reverse sequence of the transcriptional regulatory element C was the sequence as shown in SEQ ID NO: 49);

the sequence of the transcriptional regulatory element D was the sequence as shown in SEQ ID NO: 38 (the reverse sequence of the transcriptional regulatory element D was the sequence as shown in SEQ ID NO: 50);

the sequence of the transcriptional regulatory element E was the sequence as shown in SEQ ID NO: 39 (the reverse sequence of the transcriptional regulatory element E was the sequence as shown in SEQ ID NO: 51);

the sequence of the transcriptional regulatory element F was the sequence as shown in SEQ ID NO: 40 (the reverse sequence of the transcriptional regulatory element F was the sequence as shown in SEQ ID NO: 52);

the sequence of the transcriptional regulatory element G was the sequence as shown in SEQ ID NO: 41 (the reverse sequence of the transcriptional regulatory element G was the sequence as shown in SEQ ID NO: 53);

the sequence of the transcriptional regulatory element H was the sequence as shown in SEQ ID NO: 42 (the reverse sequence of the transcriptional regulatory element H was the sequence as shown in SEQ ID NO: 54);

the sequence of the transcriptional regulatory element I was the sequence as shown in SEQ ID NO: 43 (the reverse sequence of the transcriptional regulatory element I was the sequence as shown in SEQ ID NO: 55);

the sequence of the transcriptional regulatory element J was the sequence as shown in SEQ ID NO: 44 (the reverse sequence of the transcriptional regulatory element J was the sequence as shown in SEQ ID NO: 56); and the sequence of the transcriptional regulatory element K was the sequence as shown in SEQ ID NO: 45 (the reverse sequence of the transcriptional regulatory element K was the sequence as shown in SEQ ID NO: 57).

Figure 10:
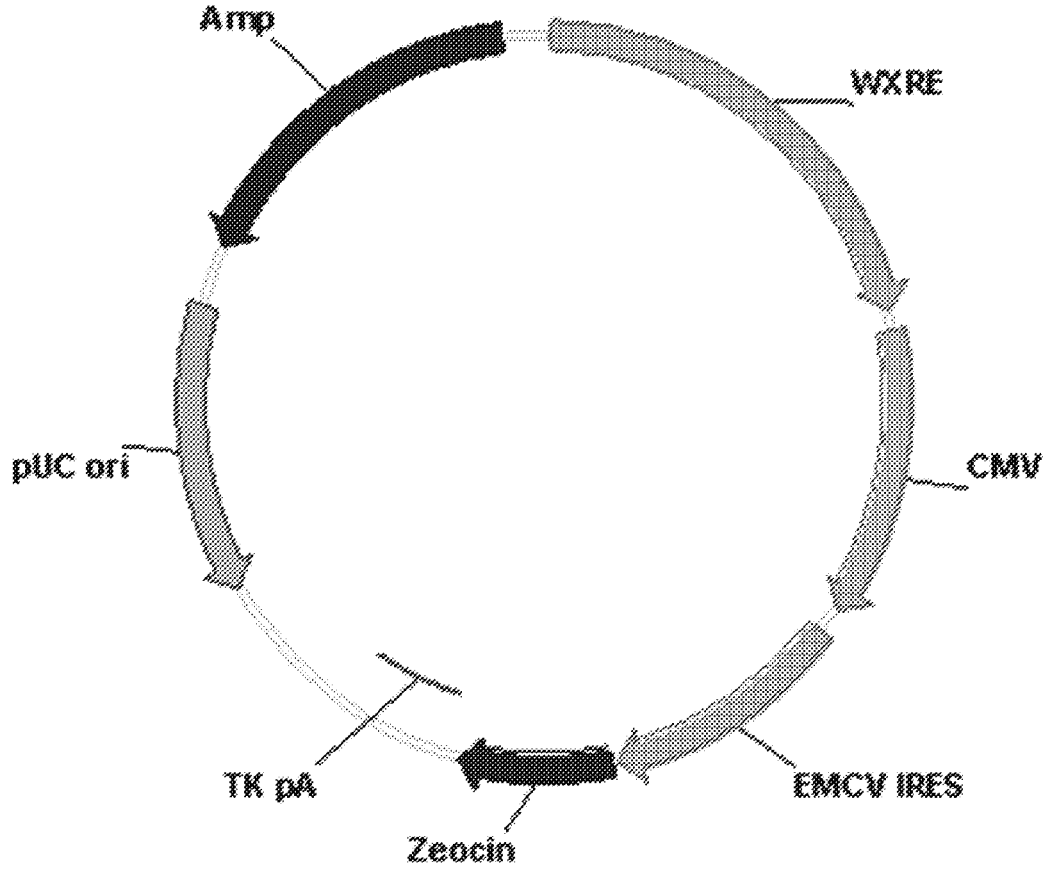
FIG. 10 illustrates a schematic diagram of a GFP-expressing vector with WXRE inserted therein.

3.2 Verification of the Transcriptional Regulatory Element 3.2.1 The transcriptional regulatory elements A~K obtained by sequencing and identification in 3.1.5 were respectively inserted into a BamHI restriction site upstream of the corresponding promoter in a vector containing the GFP gene using an In-Fusion Cloning Kit (Takara). A vector with the transcriptional regulatory element inserted therein as shown in FIG. 10 (wherein WXRE showed one of the transcriptional regulatory elements A~K) was obtained. The above-mentioned vector was linearized using the restriction endonucleases of which the restriction sites were merely located in the prokaryotic region of the backbone of the vector (for example, PvuI (NEB)), and stayed overnight at 37° C. DNA was recovered by phenol-chloroform and used for transfection the next day.

3.2.2 Approximate five million CHO host cells were centrifuged, and the supernatant was discarded. At the same time, 90 μL of SF Cell Line Solution and 20 μL of Supplement I in the Amaxa SF Cell Line 4D-Nucleofector Kit L (Lonza, Cat #VCA-1005) and 30 μg of a linearized vector containing the gene of the protein to be expressed (obtained by 3.2.1) were mixed evenly, and the cells were resuspended with this mixed solution and transferred to the electroporation cuvette. The cells were subjected to transfection using the program corresponding to the respective host cells in the 4D-Nucleofector™ System electroporation instrument. The electroporated cells were resuspended with 5 mL of medium free of antibiotic and placed in a shaker at 37° C. for cultivation. Each sample contained one kind of transcriptional regulatory element or was a control without any transcriptional regulatory element.

3.2.3 24 hours after transfection, equal volume of selective medium containing antibiotic corresponding to the resistance gene in the vector was added in the cell culture medium for screening. The cells were passaged using a medium containing antibiotic(s) every 2 to 4 days.

3.2.4 After the cell viability recovered to 90% or more, the influence of the transcriptional regulatory elements A~K on the expression level of the proteins was evaluated by fed-batch culture.

Example 4: Influence of the Transcriptional Regulatory Elements on the Expression Level of a Protein Expression System Used to Express a Heterologous Protein 4.1.1 The transcriptional regulatory elements A~K were respectively constructed into the upstream BamHI position of the promoter of a fusion protein (the above-mentioned fusion protein was the A chain of PD-L1, whose sequence was the sequence as shown in SEQ ID NO: 71) in both forward and reverse directions by using In-Fusion Cloning Kit (Takara). A vector with the transcriptional regulatory element inserted therein as shown in FIG. 10 (wherein WXRE was one of the transcriptional regulatory elements A~K) was obtained, wherein the tail number 1 of the transcriptional regulatory element indicated the forward direction and the tail number 2 of the transcriptional regulatory element indicated the reverse direction. For example, the transcriptional regulatory element A1 (as shown in SEQ ID NO: 35) indicated the forward direction ((i.e., from 5' to 3') of the sequence and was transcribed in the sense strand of the coding sequence. The transcriptional regulatory element A2 showed the reverse complementary sequence of the sequence and was as shown in SEQ ID NO: 47. That is, the transcription regulatory element A1 in the sense chain of the protein coding sequence in Example 4 was equivalent to the transcriptional regulatory element A in Example 3 of the present disclosure.

The above-mentioned vectors were linearized using the restriction endonucleases of which the restriction sites were merely located in the prokaryotic region of the backbone of the vector (for example, PvuI (NEB)) and stayed overnight under a condition of 37° C. DNA was recovered by phenol-chloroform and used for transfection the next day.

4.1.2 Approximate five million CHO host cells were centrifuged, and the supernatant was discarded. At the same time, 90 μL of SF Cell Line Solution and 20 μL of Supplement I in the Amaxa SF Cell Line 4D-Nucleofector Kit L (Lonza, Cat #VCA-1005) and 30 μg of the linearized vector containing the gene of the fusion protein (obtained by 4.1.1) were mixed evenly, and the cells were resuspended with this mixed solution and transferred to the electroporation cuvette. The cells were subjected to transfection using the program corresponding to the respective host cells in the 4D-Nucleofector™ System electroporation instrument. The electroporated cells were resuspended with 5 mL of medium free of antibiotic and placed in a shaker at 37° C. for cultivation. Samples in one group only contained one transcriptional regulatory element of a certain direction (i.e., the forward direction or the reverse direction) and a sample which did not contain any transcriptional regulatory element was taken as a control.

4.1.3 24 hours after transfection, equal volume of medium containing 800 μg/mL of Zeocin was added into the transfected cells.

4.1.4 The cells were passaged using a medium containing 400 μg/mL of Zeocin every 2 to 4 days.

4.1.5 When the cell viability recovered to 90% or more, the expression level of the fusion protein PD-L1 was subjected to evaluation by fed-batch culture.

4.1.6 Whether the sequence of the PD-L1 obtained by expression was identical to the sequence as shown in SEQ ID NO: 71 was verified.

4.2 Experimental Results

As shown in FIG. 11, as compared with the control group which did not have the transcriptional regulatory element, inserting the transcriptional regulatory element in the upstream of the promoter of the fusion protein could increase the expression level of the target protein by about 10% to 25% (see A2, B1, B2, D2, E2, F2, G1, H1, I2, J1, and K2 in FIG. 11). The promoting effect of the above-mentioned sequence on protein expression in a certain direction was superior to that in the other direction, which might be related to the directionality of the promoter.

Figure 12:
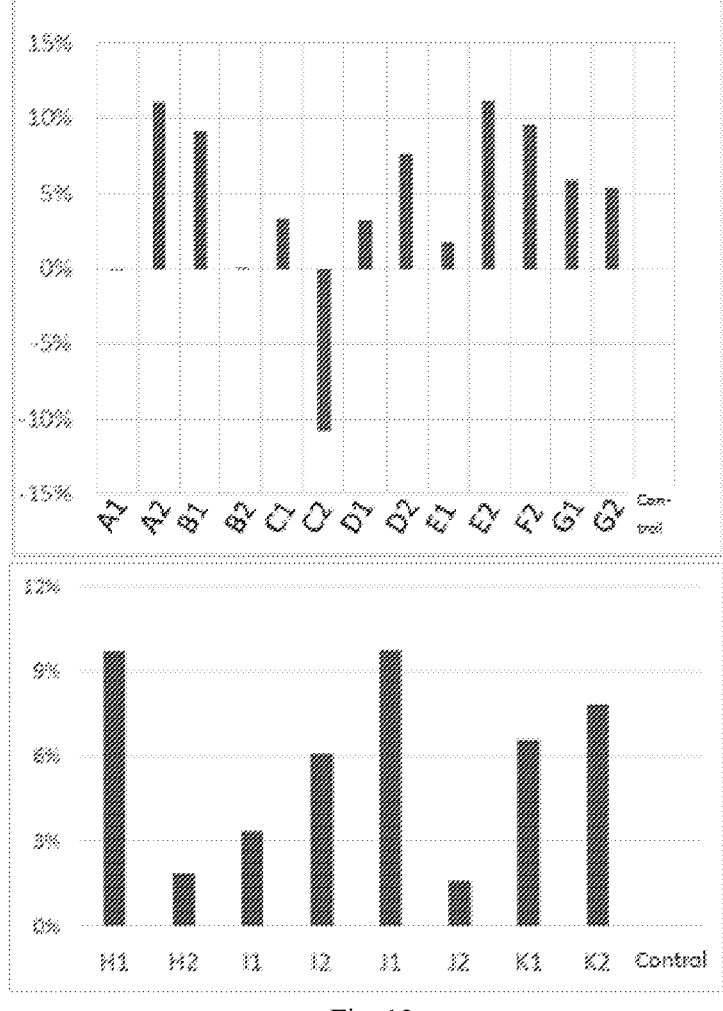
FIG. 12 illustrates the influence on the specific productivity of the expression of the fusion protein after adding transcriptional regulatory elements A~K, wherein A1 and A2 illustrate the forward and reverse directions of transcriptional regulatory element A respectively, and so forth.

As shown in FIG. 12, corresponding to the expression level, the forward or reverse transcriptional regulatory elements can make specific productivity increase by about 10% could enable an increase about 10% in specific productivity (see A2, B1, B2, D2, E2, F2, G1, H1, I2, J1, and K2 in FIG. 12).

Meanwhile, it was confirmed by verification that the sequence of the PD-L1 obtained by expression was identical to the sequence as shown in SEQ ID NO: 71.

Figure 13:
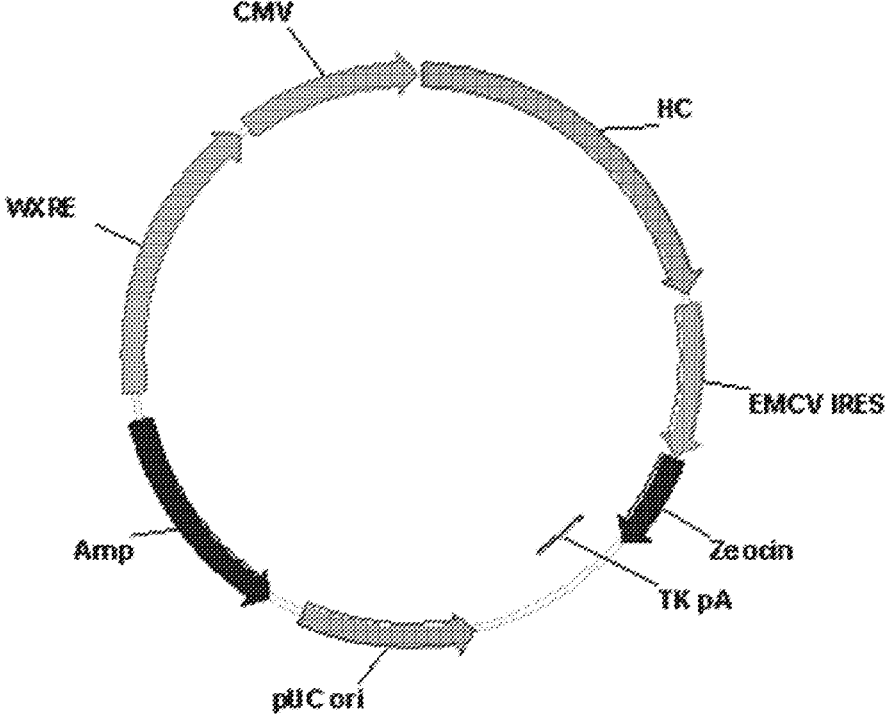
FIG. 13 illustrates a schematic diagram of a vector which expresses the heavy chain of Adalimumab and has WXRE inserted therein, wherein HC means the heavy chain.
Figure 14:
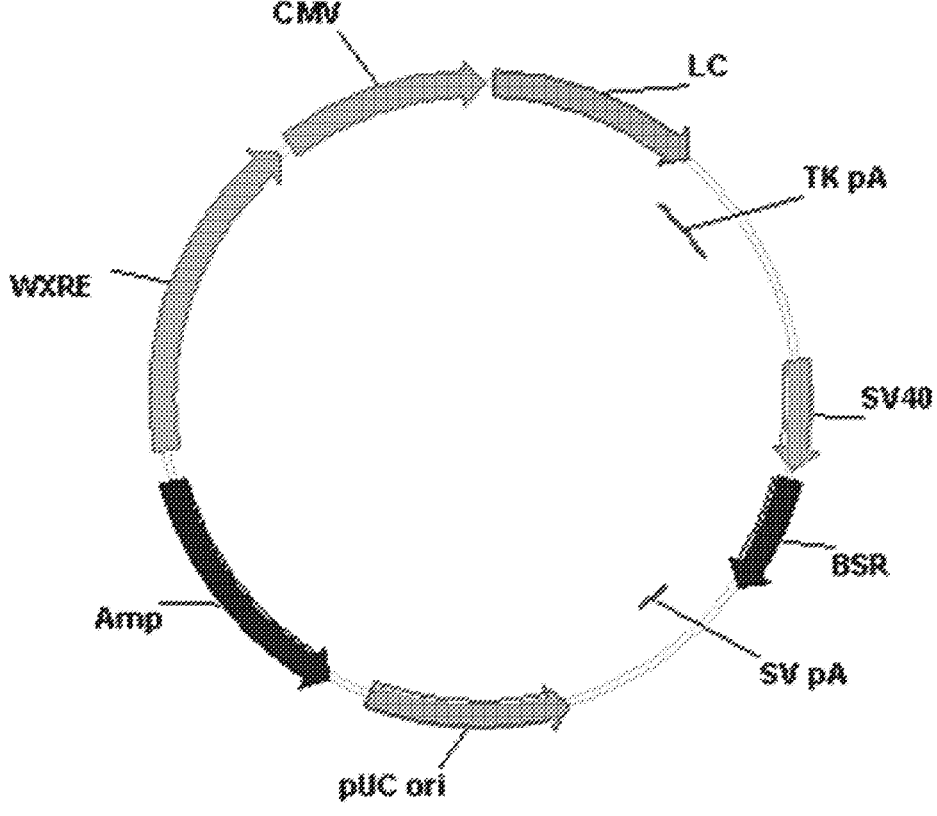
FIG. 14 illustrates a schematic diagram of a vector which expresses the light chain of Adalimumab and has WXRE inserted therein, wherein LC means the light chain.

Example 5: Influence of the Transcriptional Regulatory Elements on the Expression Level of a Protein Expression System Used to Express Adalimumab 5.1.1 The reverse sequence of the transcriptional regulatory element A (A2), the forward sequence of the transcriptional regulatory element B (B1) and the forward sequence of the transcriptional regulatory element G (G1) were respectively constructed into the upstream of the promoter of the gene that could express Adalimumab by using the In-Fusion Cloning kit of Takara (the specific conditions were as shown in Table 7). Vectors with transcriptional regulatory elements inserted therein as shown in FIG. 13 and FIG. 14 (wherein WXRE was one of the transcriptional regulatory elements A~G) were obtained respectively, wherein the "transcriptional regulatory element in the upstream of the heavy chain" was cloned into the vector as shown in FIG. 13 and the "transcriptional regulatory element in the upstream of the light chain" was cloned into the vector as shown in FIG. 14. Among them, the amino acid sequence of the heavy chain (HC) of Adalimumab in FIG. 13 was as shown in SEQ ID NO: 72 and the amino acid sequence of the light chain (LC) of Adalimumab in FIG. 14 was as shown in SEQ ID NO: 73.

The above-mentioned vector was linearized using the restriction endonucleases of which the restriction sites were merely located in the prokaryotic region of the backbone of the vector (for example, PvuI (NEB)), and stayed overnight at 37° C. The DNA was recovered by phenol-chloroform and used for transfection the next day.

TABLE 8

| | Corresponding transcriptional regulatory elements under different conditions | |
| --- | --- | --- |
| sample ID | transcriptional regulatory element in the upstream of the heavy chain | transcriptional regulatory element in the upstream of the light chain |
| 1 | B1 | B1 |
| 2 | B1 | G1 |
| 3 | G1 | G1 |
| 4 | B1 | A2 |
| 5 | G1 | A2 |
| 6 (control for 1-5) | N/A | N/A |
| 7 | H1 | H1 |
| 8 | I2 | I2 |
| 9 | J1 | J1 |
| 10 | K1 | K1 |
| 11 | K2 | K2 |
| 12 (control for 7-11) | N/A | N/A |

5.1.2 Approximate five million CHO host cells were centrifuged, and the supernatant was discarded. At the same time, 90 μL of SF Cell Line Solution and 20 μL of Supplement I in the Amaxa SF Cell Line 4D-Nucleofector Kit L (Lonza, Cat #VCA-1005) and 30 μg of the linearized vector containing the sequence of Adalimumab (obtained by 5.1.1) were mixed evenly, and the cells were resuspended with this mixed solution and transferred to the electroporation cuvette. The cells were subjected to transfection using the program corresponding to the respective host cells in the 4D-Nucleofector™ System electroporation instrument. The electroporated cells were resuspended with 5 mL of a medium free of antibiotic and placed in a shaker at 37° C. for cultivation. Samples in one group only contained one transcriptional regulatory element of a certain direction (i.e., the forward direction or the reverse direction), and a sample which did not contain any transcriptional regulatory element was taken as a control.

5.1.3 A method that was designed for quickly assessing antibody expression was used. This method could ensure that the antibody heavy chain and light chain were roughly expressed in a ratio of 1:1, and could reliably assess the antibody expression within a considerably short period of time. Twenty-four hours after transfection, equal volume of medium containing 18 μg/mL of blasticidin and 800 μg/mL of Zeocin was added into the transfected cells.

5.1.4 The cells were passaged using a medium containing 9 μg/mL of blasticidin and 400 μg/mL of Zeocin every 2 to 4 days.

5.1.5 When the cell viability recovered to 90% or more, the expression level of Adalimumab was subjected to evaluation by fed-batch culture. Since both the heavy chain expression vector and the light chain expression vector of Adalimumab could be transfected into the same host cell, the heavy chain and the light chain of Adalimumab were capable of being expressed simultaneously. Since the heavy chain and the light chain mentioned above were capable of self-assembly in the host cells, a complete Adalimumab was obtained.

5.1.6 The biological activity of the obtained Adalimumab was determined.

5.2 Experimental Results

As compared with the control group, in some of the forward sequences containing the transcriptional regulatory element B (see sample 1, 2 and 4), the expression level of Adalimumab had an increase of 10% to 20% (as shown in FIG. 15).

By determining the biological activity of Adalimumab expressed by the present heterologous protein expression vector, it was found that its biological activity was identical to the biological activity of the known commercial Adalimumab.

Example 6: Transposon-Based Stable Pool Development

A recombinant protein expressing gene and an antibiotic resistance gene were inserted between a pair of terminal repeat sequences recognizable by the piggyBac transposase. For example, if the recombinant proteins (e.g., antibodies, or Fc fusion proteins) contain multiple expressing units, these different expressing units can be cloned into vectors containing different antibiotic resistance genes.

The plasmid containing piggyBac transposase expressing gene and the plasmid containing the recombinant protein expressing gene were separately prepared by endotoxin-free plasmid kits. Neither of the plasmids were linearized by digestion.

The host cell used for the transfection was suspension-adapted CHO-K1 cell. The expected viable cell density of the host cell were between 1.0 to 3.0 million cells/mL.

To generate the cell pool expressing different human IgG1 antibodies (A, B, and C), 10 million host cells were transfected by a total of 20 μg of the transposon vectors for expressing an antibody and the transposase vector at a mass ratio of 10:1. The transposon vectors included transposon vectors for the antibody heavy chain and transposon vectors for the antibody light chain at a roughly 1:1 ratio.

Then, the transfected cells were resuspended in 10 mL of the cell culture. For controls, the same amount of the host cells were transfected by the same amount of linearized antibody expressing plasmid. These linearized antibody expressing nucleic acid were not inserted into the transposase expressing plasmids. The cells were mixed the plasmids and incubated in a Kuhner® shaking incubator.

After 24 hours of transfection, 10 mL of fresh medium containing antibiotics for selection was added to the cell culture. The antibiotic reagent corresponded to the antibiotic resistance gene. The concentration of antibiotics was determined by the killing curve experiment on the host cells. In addition, the concentration of the replenishing medium was twice the level of the antibiotic concentration for selection. This will allow the actual antibiotic concentration of the resulting cell culture to be at the selected antibiotic concentration level.

Cell passaging was carried out every 2 to 4 days with the fresh medium containing the selected antibiotic reagent. The seeding density was adjusted based on the viability, growth rate and doubling time of the cells.

After approximately 2 weeks of culture, the cell culture was used to inoculate the production basal medium at the same seeding density as determined for each transfected cell culture. The production cell cultures were incubated in a shaking incubator.

The production process was performed by fed-batch culturing. Appropriate type and amount of feeding medium was supplemented to the culture accordingly.

Figure 2:
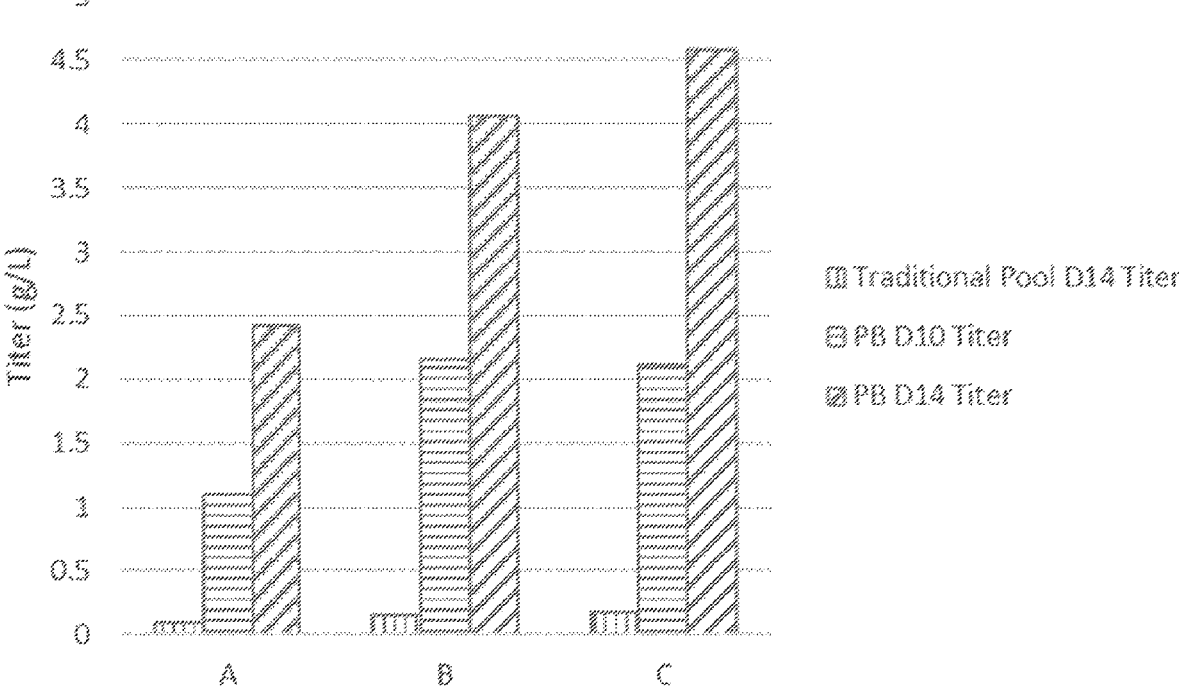
FIG. 2 is a bar graph showing protein expression levels of three antibodies (A, B, and C) in transfected host cells.

The results are shown in FIG. 2. The fed-batch culturing of the host cells applied with the piggyBac transposon system yielded 2.4 g/L antibody A, 4.1 g/L antibody B, and 4.6 g/L antibody C after 14 days of culture (PB D14 Titer). As shown in the figure, different sequences of the variable regions may lead to different expression levels. But for each antibody, the piggyBac transposon expression system significantly increased the expression level.

In contrast, the traditional stable pool controls yielded less than 0.2 g/L of antibodies (Traditional Pool D14 Titer). Therefore, the piggyBac transposon system increased protein expression by more than 10 folds under the same conditions.

Example 7: Regulatory Element Screening

RNA-seq was performed on mRNAs of CHO-K1 cell at different stages as described below. Transient transfection as well as stable transfection were performed and total RNA was extracted from: 1) 10 samples on day 6 after transient transfection; 2) 10 samples on day 8 after transient transfection; and 3) 10 stable transfection samples on day 10 of a traditional 14 days fed-batch process.

cDNA was generated and was sequenced. Based on the relative reads number, mRNA was extracted and ranked by the average abundance across all 30 samples. Regulatory element (RE) sequences were extracted from top ranked ones and were listed in the following table.

TABLE 1

| RE ID | Regulatory Element Sequences | Reverse Complement Regulatory Element Sequences |
|---|---|---|
| 01 | GCCTCTTTCTTGTTAACATGTCCAATAAAAAGAAACT TTAGTTGTACTAGT (SEQ ID NO: 1) | ACTAGTACAACTAAAGTTTCTTTTTATTGGACATGTTAAC AAGAAAGAGGC (SEQ ID NO: 16) |
| 02 | GAGGACTCTAGCTAACTCCCTGGAACAAATAAAGTT ATTTTCCAGCTTAA (SEQ ID NO: 2) | TTAAGCTGGAAAATAACTTTATTTGTTCCAGGGAGTTAGC TAGAGTCCTC (SEQ ID NO: 17) |
| 03 | GCCTGATCCCTGGCATTTCAGGCAGCTCTGAACCGT GCTGTGTGTGCTCTGGAACCTCCTTCTCTGCTCTCAG GTTCCCCAGCTCCCATCTTGGATCCAGTGGAGAGGG TTTGCTTCTGCCACCAACAGCTCCCTTTGGTACATGC TCAGCATTCAGGAGTCTTTAAGGCAATACCATCAGA GAGCAAATAAATAAACGCGTTTATGTCTCTAAGCAC A (SEQ ID NO: 3) | TGTGCTTAGAGACATAAACGCGTTTATTTATTTGCTCTCT GATGGTATTGCCTTAAAGACTCCTGAATGCTGAGCATGT ACCAAAGGGAGCTGTTGGTGGCAGAAGCAAACCCTCTCC ACTGGATCCAAGATGGGAGCTGGGGAACCTGAGAGCAG AGAAGGAGGTTCCAGAGCACACACAGCACGGTTCAGAG CTGCCTGAAATGCCAGGGATCAGGC (SEQ ID NO: 18) |
| 04 | ACAGGTTCAATCAGCTGTGCATTTGGAAAAATAAAA CTTTATTAAATCAGA (SEQ ID NO: 4) | TCTGATTTAATAAAGTTTTATTTTTCCAAATGCACAGCTGA TTGAACCTGT (SEQ ID NO: 19) |

TABLE 1-continued

| RE ID | Regulatory Element Sequences | Reverse Complement Regulatory Element Sequences |
|---|---|---|
| 05 | AGTCAACAAGCCCCTAGGCCTCAATAAAGGCAGCT GCCTCTGTTCCCCACAGCCTAAACCCTCA (SEQ ID NO: 5) | TGAGGGTTTAGGCTGTGGGGAACAGAGGCAGCTGCCTTT ATTGAGGCCTAGGGGCTTGTTGACT (SEQ ID NO: 20) |
| 06 | GCCCAATAAAGACTGTTTGTGCTAA (SEQ ID NO: 6) | TTAGCACAAACAGTCTTTATTGGGC (SEQ ID NO: 21) |
| 07 | GGGCCCCTCATACACTGCTTCCATTAAAGACTGTTTA AGTAGT (SEQ ID NO: 7) | ACTACTTAAACAGTCTTTAATGGAAGCAGTGTATGAGGG GCCC (SEQ ID NO: 22) |
| 08 | GGATTCATACAATCAATGGCAGGACTTGAGAGTTTG TACTGAATCATGATCAATACCATGTATGCTGCCAGA TGGAGTTCAACATTGTTAATCGGGAGACTTGTTCAT GCTTAAGCTGGGAATGGTTTTGTCCTGTAATAAAAA TATAGAGCCTTTCAAA (SEQ ID NO: 8) | TTTGAAAGGCTCTATATTTTTATTACAGGACAAAACCATT CCCAGCTTAAGCATGAACAAGTCTCCCGATTAACAATGTT GAACTCCATCTGGCAGCATACATGGTATTGATCATGATTC AGTACAAACTCTCAAGTCCTGCCATTGATTGTATGAATCC (SEQ ID NO: 23) |
| 09 | GACCTAAGTTAACCAGTTCCAGAAACAAGATCCTGA ATTAAGTACGATTTGGTGTGTCTTTTGGGACAATAA AGACTTGTATTGAT (SEQ ID NO: 9) | ATCAATACAAGTCTTTATTGTCCCAAAAGACACACCAAAT CGTACTTAATTCAGGATCTTGTTTCTGGAACTGGTTAACT TAGGTC (SEQ ID NO: 24) |
| 10 | AGATGTAAAACGTAAATAAAAAGCCTCCATAGACTG TT (SEQ ID NO: 10) | AACAGTCTATGGAGGCTTTTTATTTACGTTTTACATCT (SEQ ID NO: 25) |
| 11 | GCCCATCTCAAGGATCAGGGTTACCTTTGTAATAAA CATCCCAGAGCTTTAGTG (SEQ ID NO: 11) | CACTAAAGCTCTGGGATGTTTATTACAAAGGTAACCCTGA TCCTTGAGATGGGC (SEQ ID NO: 26) |
| 12 | ATCTGTTCTGTCAGATTTTCAATAAACCTG (SEQ ID NO: 12) | CAGGTTTATTGAAAATCTGACAGAACAGAT (SEQ ID NO: 27) |
| 13 | TTGTGTATGAATAAATAAAAAGACAGGAACTGA (SEQ ID NO: 13) | TCAGTTCCTGTCTTTTTATTTATTCATACACAA (SEQ ID NO: 28) |
| 14 | AATGGTCTCTAGGAGACATGCTGGAGAAATGTCTGT ACTCTTGCCTTTTTAGGCAACTGTGCTCAATTAAACA GCATGATAAAATT (SEQ ID NO: 14) | AATTTTATCATGCTGTTTAATTGAGCACAGTTGCCTAAAA AGGCAAGAGTACAGACATTTCTCCAGCATGTCTCCTAGA GACCATT (SEQ ID NO: 29) |
| 15 | CAAATTGGATCTGTCACCTGTCACCATAGCTGACTG CTGCTTGCCATCCATACAACACCAGGGCTTAGGACA AATGGGACTGATGTCATCTTGAGCTTTTATTTTGACC ATGATTTATTTGGAGTGGAGACATTGTTTTTTTTCTT TTCTTTTTTTTAAAAAGAAAGAACATGTCGTGTAGGT TGTCTGAAAATAAAGTGCATTTAAATTCACTTA (SEQ ID NO: 15) | TAAGTGAATTTAAATGCACTTTATTTTCAGACAACCTACA CGACATGTTCTTTCTTTTTAAAAAAAAGAAAAGAAAAAAA ACAATGTCTCCACTCCAAATAAATCATGGTCAAAATAAAA GCTCAAGATGACATCAGTCCCATTTGTCCTAAGCCCTGGT GTTGTATGGATGGCAAGCAGCAGTCAGCTATGGTGACAG GTGACAGATCCAATTTG (SEQ ID NO: 30) |

Experiments were performed to evaluate the effects of these RE sequences on protein expression. These RE sequences were incorporated into a fusion protein expression plasmid immediately after the recombinant protein expressing gene. The control sample did not contain any regulatory element sequences.

A total of 10 million host cells were transfected by 20 µg of the fusion protein expressing plasmids with different RE sequences. The transfected cells were resuspended in 10 mL of the host cell culture. The resulting solution was mixed and incubated in a Kuhner® shaking incubator.

After 24 hours of transfection, 10 mL of fresh medium containing antibiotics for selection was added to the transfected cell culture. Cell passaging was carried out every 2 to 4 days with the fresh medium containing selected antibiotic reagent. The seeding density was adjusted based on the viability, growth rate and doubling time of the cells.

After approximately 2 weeks of antibiotic selection, the cell culture was used to inoculate the production basal medium at the same seeding density as determined for each transfected cell culture, respectively. The production cell cultures were incubated in a shaking incubator.

The production process was performed by fed-batch culturing. Appropriate type and amount of feeding medium was supplemented to the culture accordingly.

Figure 3:
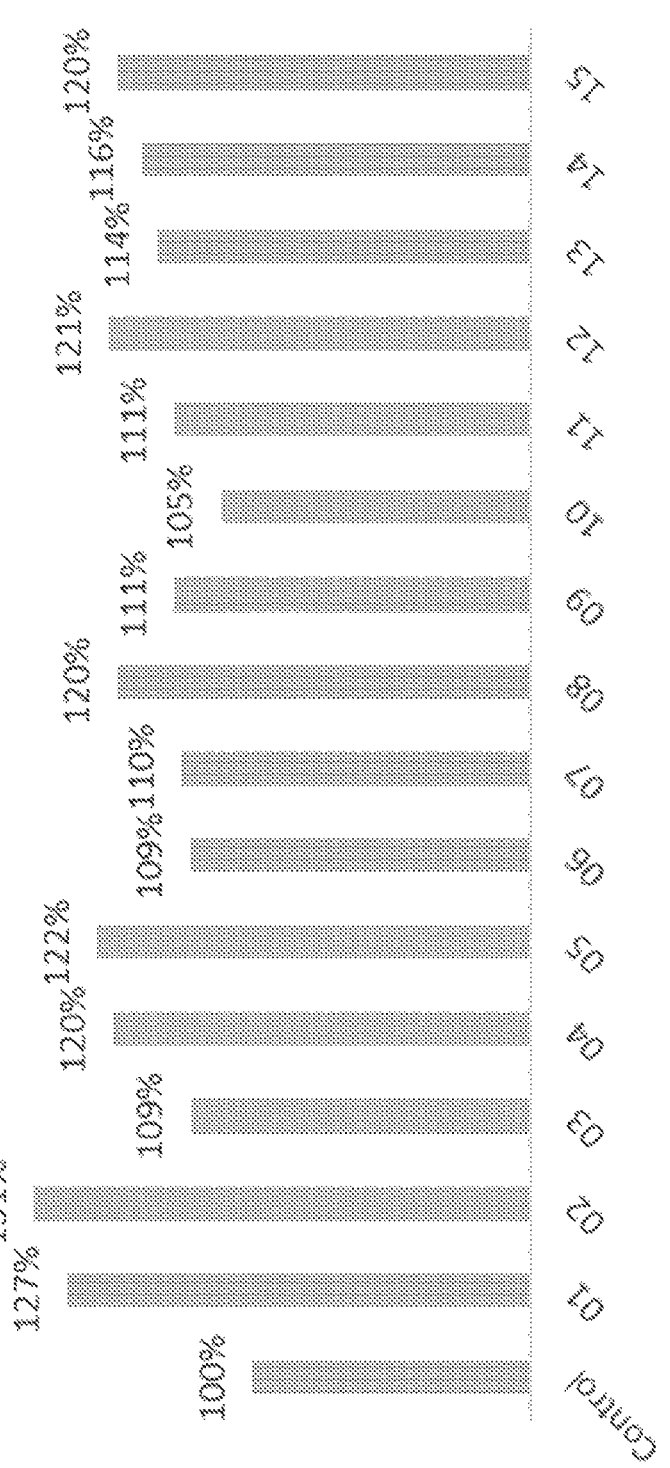
FIG. 3 is a bar graph showing protein expression levels among host cells with different regulatory elements.

As illustrated in FIG. 3, most of the regulatory element increased the protein expression by at least 10% productivity as compared to the control.

Example 8: Combination of piggyBac and Regulatory Element

A recombinant protein expressing gene, one representative regulatory element sequence and an antibiotic resistance gene were cloned between a pair of terminal repeat sequences recognizable by piggyBac recombinase. For example, if the recombinant proteins (e.g., antibodies, or Fc fusion proteins) contain multiple expressing units, these different expressing units can be cloned into vectors containing different antibiotic resistance genes.

The plasmid containing piggyBac transposase expressing gene and the plasmid containing the recombinant protein expressing gene were separately prepared by endotoxin-free plasmid kits. None of the plasmids were linearized by digestion.

The host cell used for the transfection was suspension-adapted CHO-K1 cell. The expected viable cell density of the host cell were between 1.0 to 3.0 million cells/mL.

To generate the cell pool expressing different human IgG1 antibodies (D, E, and F), 10 million host cells were transfected by 20 µg of the piggyBac transposon vectors (with or without WXRE ID: B (SEQ ID NO: 36)) and the transposase vectors at a mass ratio of 10:1. Then, the transfected cells were resuspended in 10 mL of the host cell culture. As traditional stable pool controls, the same amount of the host cells were transfected by the same amount of linearized antibody expressing plasmids. The resulting solution was mixed and incubated in a Kuhner® shaking incubator.

After 24 hours of transfection, 10 mL of fresh medium containing antibiotics for selection was added to the transfected cell culture. The antibiotic reagent corresponded to the antibiotic resistance gene as decided herein. The concentration of antibiotics was determined by the killing curve experiment on the host cell. In addition, the concentration of the replenishing medium was twice the level of the selected antibiotic concentration for selection, so that the actual antibiotic concentration of the resulting cell culture is the same as the selected antibiotic concentration.

Cell passaging was carried out every 2 to 4 days with the fresh medium containing the selected antibiotic reagent. The seeding density was adjusted based on the viability rate and doubling time of the cells.

After 2 weeks of antibiotic selection, the cell culture was used to inoculate the production basal medium at the same seeding density as determined for each transfected cell culture, respectively. The production cell cultures were incubated in a shaking incubator.

The production process was performed by fed-batch culturing. Appropriate type and amount of feeding medium was supplemented to the culture accordingly.

Figure 4:
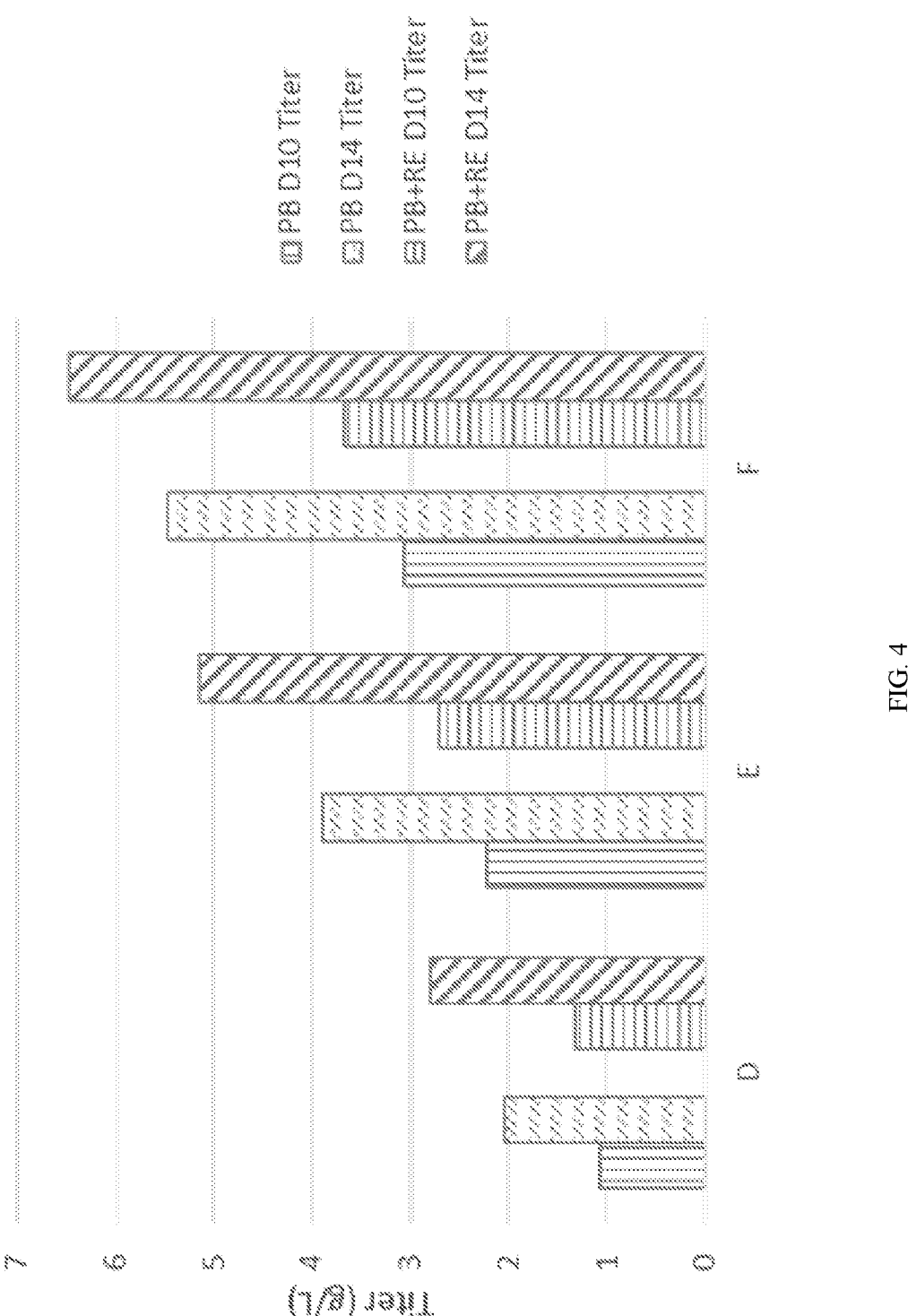
FIG. 4 is a bar graph showing protein expression levels of three antibodies (D, E, and F) in host cells transfected with piggyBac transposon plasmids with or without regulatory elements.

As illustrated in FIG. 4, after 14 days, the protein expression (titer) of the three groups of production cell cultures using the piggyBac transposon system alone (without the RE sequence) were 2.1 g/L, 3.9 g/L and 5.5 g/L, respectively. However, the expression increased to 2.8 g/L, 5.2 g/L and 6.5 g/L, respectively, when the RE sequence was present in the antibody expressing plasmids. The results indicated that combination of piggyBac transposon system and regulatory element sequences (e.g., WXRE) can further increase protein production.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid comprising
   a 5'-ITR (inverted terminal repeat) sequence;
   a 3'-ITR sequence; and
   a regulatory element sequence that is at least 90% identical to a sequence selected from the group consisting of SEQ ID NOs: 36, 43, 46, 48, 55, and 58.

2. The nucleic acid of claim 1, wherein the 5' ITR sequence comprises a sequence that is at least 90% identical to SEQ ID NO: 68, and the 3' ITR sequence comprises a sequence that is at least 90% identical to SEQ ID NO: 60.

3. The nucleic acid of claim 1, wherein the 5' ITR sequence comprises SEQ ID NO: 68 and the 3' ITR sequence comprises SEQ ID NO: 60.

4. The nucleic acid of claim 1, further comprising a 5'-internal domain and a 3'-internal domain, wherein the 5'-internal domain comprise a sequence that is at least 90% identical to SEQ ID NO: 66, wherein the 3'-internal domain comprise a sequence that is at least 90% identical to SEQ ID NO: 67, wherein the 5'-internal domain is immediately adjacent to the 5'-ITR, and the 3'-internal domain is immediately adjacent to the 3'-ITR.

5. The nucleic acid of claim 1, wherein the nucleic acid comprises one or more regulatory element sequences selected from the group consisting of SEQ ID NO: 36 and SEQ ID NO: 48.

6. The nucleic acid of claim 1, further comprising a promoter and a sequence encoding a polypeptide, wherein the sequence encoding the polypeptide is operably linked to the promoter.

7. The nucleic acid of claim 6, wherein the sequence encoding a polypeptide is located between two regulatory element sequences.

8. The nucleic acid of claim 1, further comprising a promoter and a sequence encoding two or more polypeptides, wherein the sequence encoding the two or more polypeptides is operably linked to the promoter.

9. The nucleic acid of claim 8, wherein the sequence encoding two or more polypeptides encodes an antibody heavy chain and an antibody light chain.

10. The nucleic acid of claim 1, wherein in addition to the regulatory element sequence, the nucleic acid further comprises an additional sequence that is at least 90% identical to a sequence selected from the group consisting of SEQ ID NOs: 36 and 48.

11. The nucleic acid of claim 1, wherein the nucleic acid comprises two or more expression cassettes.

12. The nucleic acid of claim 1, wherein the nucleic acid comprises a selection marker.

13. The nucleic acid of claim 12, wherein the selection marker is an antibiotic resistance gene, a sequence encoding a fluorescent protein, or lacZ.

14. The nucleic acid of claim 1, wherein the 5'-ITR comprises a $TR_L$, a 5'-ITR spacer and an $IR_L$, and the 3'-ITR comprises an $IR_R$, a 3'-ITR spacer and a $TR_R$.

15. The nucleic acid of claim 14, wherein the $TR_L$ comprises a sequence that is at least 90% identical to a reverse sequence or a reverse complementary sequence of SEQ ID NO: 61; wherein the 5'-ITR spacer comprises a sequence that is at least 90% identical to a reverse sequence or a reverse complementary sequence of SEQ ID NO: 62; wherein the $IR_L$ comprises a sequence that is at least 90% identical to a reverse sequence or a reverse complementary sequence of SEQ ID NO: 63; wherein the $TR_R$ comprises a sequence that is at least 90% identical to a reverse sequence or a reverse complementary sequence of SEQ ID NO: 64; and wherein the $IR_R$ comprises a sequence that is at least 90% identical to a reverse sequence or a reverse complementary sequence of SEQ ID NO: 65.

16. The nucleic acid of claim 1, wherein the regulatory element sequence is at least 90% identical to a sequence selected from the group consisting of SEQ ID NO: 36 and SEQ ID NO: 48.

17. The nucleic acid of claim 1, wherein the regulatory element sequence is at least 90% identical to a sequence selected from the group consisting of SEQ ID NO: 43 and SEQ ID NO: 55.

18. The nucleic acid of claim 1, wherein the regulatory element sequence is at least 90% identical to a sequence selected from the group consisting of SEQ ID NO: 46 and SEQ ID NO: 58.

19. A vector comprising the nucleic acid of claim 1.

20. The vector of claim 19, comprising the following genetic elements in a 5' to 3' direction:
   the 5'-ITR comprising a $TR_L$, a 5'-ITR spacer, a $IR_L$;
   a promoter;
   the regulatory element sequence;
   a protein-coding sequence; and
   the 3'-ITR comprising a $IR_R$, a 3'-ITR spacer, a $TR_R$.

21. The vector of claim 20, wherein the $TR_L$ comprises a sequence that is at least 90% identical to a reverse sequence or a reverse complementary sequence of SEQ ID NO: 61; wherein the 5'-ITR spacer comprises a sequence that is at least 90% identical to a reverse sequence or a reverse complementary sequence of SEQ ID NO: 62; wherein the $IR_L$ comprises a sequence that is at least 90% identical to a reverse sequence or a reverse complementary sequence of SEQ ID NO: 63; wherein the $TR_R$ comprises a sequence that is at least 90% identical to a reverse sequence or a reverse complementary sequence of SEQ ID NO: 64; and wherein the $IR_R$ comprises a sequence that is at least 90% identical to a reverse sequence or a reverse complementary sequence of SEQ ID NO: 65.

22. A cell comprising the nucleic acid of claim 1.

* * * * *

SEQUENCE LISTING

```
<160> NUMBER OF SEQ ID NOS: 73

<210> SEQ ID NO 1
<211> LENGTH: 51
<212> TYPE: DNA
<213> ORGANISM: Artificial Sequence
<220> FEATURE:
<223> OTHER INFORMATION: Regulatory Element Sequence 01

<400> SEQUENCE: 1
gcctctttct tgttaacatg tccaataaaa agaaacttta gttgtactag t          51

<210> SEQ ID NO 2
<211> LENGTH: 50
<212> TYPE: DNA
<213> ORGANISM: Artificial Sequence
<220> FEATURE:
<223> OTHER INFORMATION: Regulatory Element Sequence 02

<400> SEQUENCE: 2
gaggactcta gctaactccc tggaacaaat aaagttattt tccagcttaa           50

<210> SEQ ID NO 3
<211> LENGTH: 219
<212> TYPE: DNA
<213> ORGANISM: Artificial Sequence
<220> FEATURE:
<223> OTHER INFORMATION: Regulatory Element Sequence 03

<400> SEQUENCE: 3
gcctgatccc tggcatttca ggcagctctg aaccgtgctg tgtgtgctct ggaacctcct      60
tctctgctct caggttcccc agctcccatc ttggatccag tggagagggt ttgcttctgc     120
caccaacagc tccctttggt acatgctcag cattcaggag tctttaaggc aataccatca     180
gagagcaaat aaataaacgc gtttatgtct ctaagcaca                          219

<210> SEQ ID NO 4
<211> LENGTH: 51
```

```
<212> TYPE: DNA
<213> ORGANISM: Artificial Sequence
<220> FEATURE:
<223> OTHER INFORMATION: Regulatory Element Sequence 04

<400> SEQUENCE: 4
acaggttcaa tcagctgtgc atttggaaaa ataaaacttt attaaatcag a              51

<210> SEQ ID NO 5
<211> LENGTH: 64
<212> TYPE: DNA
<213> ORGANISM: Artificial Sequence
<220> FEATURE:
<223> OTHER INFORMATION: Regulatory Element Sequence 05

<400> SEQUENCE: 5
agtcaacaag cccctaggcc tcaataaagg cagctgcctc tgttccccac agcctaaacc      60
ctca                                                                  64

<210> SEQ ID NO 6
<211> LENGTH: 25
<212> TYPE: DNA
<213> ORGANISM: Artificial Sequence
<220> FEATURE:
<223> OTHER INFORMATION: Regulatory Element Sequence 06

<400> SEQUENCE: 6
gcccaataaa gactgtttgt gctaa                                           25

<210> SEQ ID NO 7
<211> LENGTH: 43
<212> TYPE: DNA
<213> ORGANISM: Artificial Sequence
<220> FEATURE:
<223> OTHER INFORMATION: Regulatory Element Sequence 07

<400> SEQUENCE: 7
gggcccctca tacactgctt ccattaaaga ctgtttaagt agt                       43

<210> SEQ ID NO 8
<211> LENGTH: 160
<212> TYPE: DNA
<213> ORGANISM: Artificial Sequence
<220> FEATURE:
<223> OTHER INFORMATION: Regulatory Element Sequence 08

<400> SEQUENCE: 8
ggattcatac aatcaatggc aggacttgag agtttgtact gaatcatgat caataccatg      60
tatgctgcca gatggagttc aacattgtta atcgggagac ttgttcatgc ttaagctggg     120
aatggttttg tcctgtaata aaaatataga gcctttcaaa                          160

<210> SEQ ID NO 9
<211> LENGTH: 86
<212> TYPE: DNA
<213> ORGANISM: Artificial Sequence
<220> FEATURE:
<223> OTHER INFORMATION: Regulatory Element Sequence 09

<400> SEQUENCE: 9
gacctaagtt aaccagttcc agaaacaaga tcctgaatta agtacgattt ggtgtgtctt      60
ttgggacaat aaagacttgt attgat                                          86

<210> SEQ ID NO 10
```

```
<211> LENGTH: 38
<212> TYPE: DNA
<213> ORGANISM: Artificial Sequence
<220> FEATURE:
<223> OTHER INFORMATION: Regulatory Element Sequence 10

<400> SEQUENCE: 10
agatgtaaaa cgtaaataaa aagcctccat agactgtt                              38

<210> SEQ ID NO 11
<211> LENGTH: 54
<212> TYPE: DNA
<213> ORGANISM: Artificial Sequence
<220> FEATURE:
<223> OTHER INFORMATION: Regulatory Element Sequence 11

<400> SEQUENCE: 11
gcccatctca aggatcaggg ttacctttgt aataaacatc ccagagcttt agtg           54

<210> SEQ ID NO 12
<211> LENGTH: 30
<212> TYPE: DNA
<213> ORGANISM: Artificial Sequence
<220> FEATURE:
<223> OTHER INFORMATION: Regulatory Element Sequence 12

<400> SEQUENCE: 12
atctgttctg tcagattttc aataaacctg                                      30

<210> SEQ ID NO 13
<211> LENGTH: 33
<212> TYPE: DNA
<213> ORGANISM: Artificial Sequence
<220> FEATURE:
<223> OTHER INFORMATION: Regulatory Element Sequence 13

<400> SEQUENCE: 13
ttgtgtatga ataaataaaa agacaggaac tga                                  33

<210> SEQ ID NO 14
<211> LENGTH: 86
<212> TYPE: DNA
<213> ORGANISM: Artificial Sequence
<220> FEATURE:
<223> OTHER INFORMATION: Regulatory Element Sequence 14

<400> SEQUENCE: 14
aatggtctct aggagacatg ctggagaaat gtctgtactc ttgccttttt aggcaactgt     60
gctcaattaa acagcatgat aaaatt                                          86

<210> SEQ ID NO 15
<211> LENGTH: 216
<212> TYPE: DNA
<213> ORGANISM: Artificial Sequence
<220> FEATURE:
<223> OTHER INFORMATION: Regulatory Element Sequence 15

<400> SEQUENCE: 15
caaattggat ctgtcacctg tcaccatagc tgactgctgc ttgccatcca tacaacacca     60
gggcttagga caaatgggac tgatgtcatc ttgagctttt attttgacca tgatttattt    120
ggagtggaga cattgttttt tttcttttct ttttttaaa aagaaagaac atgtcgtgta     180
ggttgtctga aaataaagtg catttaaatt cactta                              216
```

-continued

```
<210> SEQ ID NO 16
<211> LENGTH: 51
<212> TYPE: DNA
<213> ORGANISM: Artificial Sequence
<220> FEATURE:
<223> OTHER INFORMATION: Reverse Complement Regulatory Element Sequence
      01

<400> SEQUENCE: 16
actagtacaa ctaaagtttc tttttattgg acatgttaac aagaaagagg c          51

<210> SEQ ID NO 17
<211> LENGTH: 50
<212> TYPE: DNA
<213> ORGANISM: Artificial Sequence
<220> FEATURE:
<223> OTHER INFORMATION: Reverse Complement Regulatory Element Sequence
      02

<400> SEQUENCE: 17
ttaagctgga aaataacttt atttgttcca gggagttagc tagagtcctc            50

<210> SEQ ID NO 18
<211> LENGTH: 219
<212> TYPE: DNA
<213> ORGANISM: Artificial Sequence
<220> FEATURE:
<223> OTHER INFORMATION: Reverse Complement Regulatory Element Sequence
      03

<400> SEQUENCE: 18
tgtgcttaga gacataaacg cgtttattta tttgctctct gatggtattg ccttaaagac  60
tcctgaatgc tgagcatgta ccaaagggag ctgttggtgg cagaagcaaa ccctctccac  120
tggatccaag atgggagctg gggaacctga gagcagagaa ggaggttcca gagcacacac  180
agcacggttc agagctgcct gaaatgccag ggatcaggc                        219

<210> SEQ ID NO 19
<211> LENGTH: 51
<212> TYPE: DNA
<213> ORGANISM: Artificial Sequence
<220> FEATURE:
<223> OTHER INFORMATION: Reverse Complement Regulatory Element Sequence
      04

<400> SEQUENCE: 19
tctgatttaa taaagtttta tttttccaaa tgcacagctg attgaacctg t           51

<210> SEQ ID NO 20
<211> LENGTH: 64
<212> TYPE: DNA
<213> ORGANISM: Artificial Sequence
<220> FEATURE:
<223> OTHER INFORMATION: Reverse Complement Regulatory Element Sequence
      05

<400> SEQUENCE: 20
tgagggttta ggctgtgggg aacagaggca gctgccttta ttgaggccta ggggcttgtt  60
gact                                                               64

<210> SEQ ID NO 21
<211> LENGTH: 25
<212> TYPE: DNA
<213> ORGANISM: Artificial Sequence
<220> FEATURE:
<223> OTHER INFORMATION: Reverse Complement Regulatory Element Sequence
```

-continued

```
    06

<400> SEQUENCE: 21
ttagcacaaa cagtctttat tgggc                                          25

<210> SEQ ID NO 22
<211> LENGTH: 43
<212> TYPE: DNA
<213> ORGANISM: Artificial Sequence
<220> FEATURE:
<223> OTHER INFORMATION: Reverse Complement Regulatory Element Sequence
      07

<400> SEQUENCE: 22
actacttaaa cagtctttaa tggaagcagt gtatgagggg ccc                     43

<210> SEQ ID NO 23
<211> LENGTH: 160
<212> TYPE: DNA
<213> ORGANISM: Artificial Sequence
<220> FEATURE:
<223> OTHER INFORMATION: Reverse Complement Regulatory Element Sequence
      08

<400> SEQUENCE: 23
tttgaaaggc tctatatttt tattacagga caaaaccatt cccagcttaa gcatgaacaa    60
gtctcccgat taacaatgtt gaactccatc tggcagcata catggtattg atcatgattc   120
agtacaaact ctcaagtcct gccattgatt gtatgaatcc                         160

<210> SEQ ID NO 24
<211> LENGTH: 86
<212> TYPE: DNA
<213> ORGANISM: Artificial Sequence
<220> FEATURE:
<223> OTHER INFORMATION: Reverse Complement Regulatory Element Sequence
      09

<400> SEQUENCE: 24
atcaatacaa gtctttattg tcccaaaaga cacaccaaat cgtacttaat tcaggatctt    60
gtttctggaa ctggttaact taggtc                                        86

<210> SEQ ID NO 25
<211> LENGTH: 38
<212> TYPE: DNA
<213> ORGANISM: Artificial Sequence
<220> FEATURE:
<223> OTHER INFORMATION: Reverse Complement Regulatory Element Sequence
      10

<400> SEQUENCE: 25
aacagtctat ggaggctttt tatttacgtt ttacatct                           38

<210> SEQ ID NO 26
<211> LENGTH: 54
<212> TYPE: DNA
<213> ORGANISM: Artificial Sequence
<220> FEATURE:
<223> OTHER INFORMATION: Reverse Complement Regulatory Element Sequence
      11

<400> SEQUENCE: 26
cactaaagct ctgggatgtt tattacaaag gtaaccctga tccttgagat gggc          54

<210> SEQ ID NO 27
```

```
<211> LENGTH: 30
<212> TYPE: DNA
<213> ORGANISM: Artificial Sequence
<220> FEATURE:
<223> OTHER INFORMATION: Reverse Complement Regulatory Element Sequence
      12

<400> SEQUENCE: 27
caggtttatt gaaaatctga cagaacagat                                              30

<210> SEQ ID NO 28
<211> LENGTH: 33
<212> TYPE: DNA
<213> ORGANISM: Artificial Sequence
<220> FEATURE:
<223> OTHER INFORMATION: Reverse Complement Regulatory Element Sequence
      13

<400> SEQUENCE: 28
tcagttcctg tctttttatt tattcataca caa                                          33

<210> SEQ ID NO 29
<211> LENGTH: 86
<212> TYPE: DNA
<213> ORGANISM: Artificial Sequence
<220> FEATURE:
<223> OTHER INFORMATION: Reverse Complement Regulatory Element Sequence
      14

<400> SEQUENCE: 29
aattttatca tgctgtttaa ttgagcacag ttgcctaaaa aggcaagagt acagacattt      60
ctccagcatg tctcctagag accatt                                                  86

<210> SEQ ID NO 30
<211> LENGTH: 216
<212> TYPE: DNA
<213> ORGANISM: Artificial Sequence
<220> FEATURE:
<223> OTHER INFORMATION: Reverse Complement Regulatory Element Sequence
      15

<400> SEQUENCE: 30
taagtgaatt taaatgcact ttattttcag acaacctaca cgacatgttc tttcttttta      60
aaaaaaagaa aagaaaaaaa acaatgtctc cactccaaat aaatcatggt caaaataaaa    120
gctcaagatg acatcagtcc catttgtcct aagccctggt gttgtatgga tggcaagcag    180
cagtcagcta tggtgacagg tgacagatcc aatttg                                      216

<210> SEQ ID NO 31
<211> LENGTH: 238
<212> TYPE: DNA
<213> ORGANISM: Artificial Sequence
<220> FEATURE:
<223> OTHER INFORMATION: A first PB transposase recognition site
      sequence

<400> SEQUENCE: 31
ttaaccctag aaagataatc atattgtgac gtacgttaaa gataatcatg cgtaaaattg      60
acgcatgtgt tttatcggtc tgtatatcga ggtttattta ttaatttgaa tagatattaa    120
gttttattat atttacactt acatactaat aataaattca acaaacaatt tatttatgtt    180
tatttattta ttaaaaaaaa acaaaaactc aaaatttctt ctataaagta acaaaact      238

<210> SEQ ID NO 32
```

-continued

```
<211> LENGTH: 311
<212> TYPE: DNA
<213> ORGANISM: Artificial Sequence
<220> FEATURE:
<223> OTHER INFORMATION: A second PB transposase recognition site
      sequence

<400> SEQUENCE: 32
tatctataac aagaaaatat atatataata agttatcacg taagtagaac atgaaataac      60
aatataatta tcgtatgagt taaatcttaa aagtcacgta aaagataatc atgcgtcatt     120
ttgactcacg cggtcgttat agttcaaaat cagtgacact taccgcattg acaagcacgc     180
ctcacgggag ctccaagcgg cgactgagat gtcctaaatg cacagcgacg gattcgcgct     240
atttagaaag agagagcaat atttcaagaa tgcatgcgtc aattttacgc agactatctt     300
tctagggtta a                                                         311

<210> SEQ ID NO 33
<211> LENGTH: 594
<212> TYPE: PRT
<213> ORGANISM: Artificial Sequence
<220> FEATURE:
<223> OTHER INFORMATION: The second nucleic acid encoding a piggyBac
      transposase

<400> SEQUENCE: 33

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
                20                  25                  30

His Val Ser Glu Asp Asp Val Gln Ser Asp Thr Glu Glu Ala Phe Ile
            35                  40                  45

Asp Glu Val His Glu Val Gln Pro Thr Ser Ser Gly Ser Glu Ile Leu
        50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
            115                 120                 125

Tyr Asp Pro Leu Leu Cys Phe Lys Leu Phe Phe Thr Asp Glu Ile Ile
        130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
        210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255
```

```
Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
            275                 280                 285

Ser Lys Tyr Gly Ile Lys Ile Leu Met Met Cys Asp Ser Gly Thr Lys
            290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
            325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
            355                 360                 365

Gly Thr Val Arg Ser Asn Lys Arg Glu Ile Pro Glu Val Leu Lys Asn
            370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
            405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
            435                 440                 445

Leu Asp Gln Met Cys Ser Val Met Thr Cys Ser Arg Lys Thr Asn Arg
            450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
            485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
            515                 520                 525

Arg Asp Asn Ile Ser Asn Ile Leu Pro Asn Glu Val Pro Gly Thr Ser
            530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
            565                 570                 575

Cys Lys Lys Val Ile Cys Arg Glu His Asn Ile Asp Met Cys Gln Ser
            580                 585                 590

Cys Phe
```

<210> SEQ ID NO 34
<211> LENGTH: 943
<212> TYPE: DNA
<213> ORGANISM: Artificial Sequence
<220> FEATURE:
<223> OTHER INFORMATION: Human EF-1alpha gene intron 1

<400> SEQUENCE: 34
gtaagtgccg tgtgtggttc ccgcgggcct ggcctcttta cgggttatgg cccttgcgtg        60
ccttgaatta cttccacgcc cctggctgca gtacgtgatt cttgatcccg agcttcgggt       120

```
tggaagtggg tgggagagtt cgaggccttg cgcttaagga gccccttcgc ctcgtgcttg      180
agttgaggcc tggcttgggc gctggggccg ccgcgtgcga atctggtggc accttcgcgc      240
ctgtctcgct gctttcgata agtctctagc catttaaaat ttttgatgac ctgctgcgac      300
gctttttttc tggcaagata gtcttgtaaa tgcgggccaa gatctgcaca ctggtatttc      360
ggttttgggg gccgcgggcg gcgacggggc ccgtgcgtcc cagcgcacat gttcggcgag      420
gcggggcctg cgagcgcggc caccgagaat cggacggggg tagtctcaag ctggccggcc      480
tgctctggtg cctggcctcg cgccgccgtg tatcgccccg ccctgggcgg caaggctggc      540
ccggtcggca ccagttgcgt gagcggaaag atggccgctt cccggccctg ctgcagggag      600
ctcaaaatgg aggacgcggc gctcgggaga gcgggcgggt gagtcaccca cacaaaggaa      660
aagggccttt ccgtcctcag ccgtcgcttc atgtgactcc acggagtacc gggcgccgtc      720
caggcacctc gattagttct cgagcttttg gagtacgtcg tctttaggtt gggggggaggg      780 gttttatgcg atggagtttc cccacactga gtgggtggag actgaagtta ggccagcttg      840
gcacttgatg taattctcct tggaatttgc ccttttttgag tttggatctt ggttcattct      900
caagcctcag acagtggttc aaagttttttt tcttccattt cag      943
```

```
<210> SEQ ID NO 35
<211> LENGTH: 3619
<212> TYPE: DNA
<213> ORGANISM: Artificial Sequence
<220> FEATURE:
<223> OTHER INFORMATION: Transcription regulatory element A

<400> SEQUENCE: 35
gatctgcctg cctctgcccc gtgagtgctg ggattaaagg ccagcaccgc catgcctggc       60
ctcctttaag tgcaggtgta gcacgccaga aataccctgc tggtgacagt gtgagccaca      120
tgcgtgagac tgctgcagag gtcccagctt aggttgtgcc cttctttctt gagaaatgtc      180
ttacttggtg attttgagtg gaaacatgta tttagctgac atatgagcct agtctttttat      240 gtataaatgt gtgttatatt tctagataca aaaatattaa aaattagaaa tcttcagggc      300
tggagagggg ttcattggtt aagagctcat tggttaaggg ctgctcctgt ataggacccg      360
ggttacctgt cagcaccgta tgacggctct caaccatctg cagctcccgt tccagaggac      420
ccagtgtctt cttctggcct ctacagacat acatatagac aaaacaccca tacacaaaaa      480
tttaattaga aatcttaatt tttttctttc aattttctag attgactggg ataacttttt      540
ttgttaactt tactgtcttg aggataacgt tcagtatgag ttgtatttct agagtttgtc      600
tttattttta ggcaaaaata acctttatta ccattttggg gggtgactgt tttacaactt      660
ttccaacttt ctgcttcatc tcttgtgtcc tatataggcc cctatttact gtcattatta      720
gagataggac ttgatgtcat gtcaactcca tctttgttat aaatctcaag aagagctaat      780
ttcttttgtg ttattacaac caaaaataaa caaggtagct tataaacagt gacttatttt      840
tatagttcta gatatgggaa gatcatggtg acagtagatt caatgtctag ttggaagttg      900
actcttcttc atagatggaa tccttgctat aatataatct caggatggaa gggatgagct      960
aagccctctg ggatctctta ttaatctgtt cattcattta cttattgcat agtgctctaa     1020
ttctgttcat ggagactctg ttcttacaca ttaggtggtt agggagggac atgatcaatc     1080
aggacatagg agcaacaata attttttatta tatttcccaa aatacatggc agttcctgac     1140
cttgctttat tactgcaaac atacagcttg tggccattgg acttagccat atgagaaatg     1200
```

-continued

```
taagaattta ttttatattg tagctgcaaa tggtaggttc atcaaattgt gccttaagtt    1260
cacatcttaa tttgctacaa aaaaaaaaga ggagtagtgt aagttacatt taattttcaa    1320
ttacttagta acagtttgta agtgctactt gatcctgttt tatatctagc attgagtata    1380
gatcaacaag tgtttcaatt cttgtttgga catgctgttc tctccttcat cacaagttac    1440
ttctggctaa acaaggcaca aatttcgcat gaccaccaat ccaaggacag ggcgacaatt    1500
ttaatgagtt tcattgagag ctggccaact gagcatctgt tccttttgtt ttcctgtacg    1560
tggtaagcca gtgtttctac actccttagc cttgttgctg tgtgtatagt gtggggtgga    1620
tttgtttttg ctgttctttt ttcttttttc taccctctac ttcagtggtg cacggttaga    1680
aatcttgtgg cgtctggcac ggtggtataa ttccttccat gctcttgggt gaggaaataa    1740
gtttgctcat tgctgctcat cagtctgttt cacttgctcc cagatggtga ccttctcgtc    1800
ccattcttgc ttgtttttaac attattctga cacctatttt ctttcattgt ccccttaacc    1860
actctaattg aataatgatt tctgtaattt ccatttggaa cacaaccagc ttcctggttc    1920
cttttattgg cccacatcct gtcttctagt tcattgcttc agatttgagc caaatcatca    1980
aataaaaata cgtaactgaa aaaaatgttt attgcagtgg cctcctctag catggcaaca    2040
atgagagttt tcctttctta ttgctaaaca tgttatatct gtctcatgat ttcatactgt    2100
ctctcctggc ctcatttact gcttgacctt taaaagaaat gactcaaaga tattttgta    2160 gttctgtaag catttctcta gttcttgttc ttcacctttta gttcttaaca gtagttttgt    2220
ctgctacact gacgtggctg tgaggacttt ccttcagaaa ctggcgtctg atactgattc    2280
aaactggtct ccattgtggc ctacatgtcc agctgtctcc atgtaacgcc actgaaatac    2340
agtgaagcca gccttttttt cccccttatg gttcaaagca actgaatttc agtcagagta    2400
attttggttt gggtatcaat actaattgta gtccttagacc ttttaattat tacttgtttg    2460
cattttacag aagacattgg tccttctcaa aagcagagat gaaacctgta gtattttgtg    2520
tgtagttttc ctctgctggt tgccctgtaa ctattcagtt cctgtaagga agcacagctg    2580
cttcataagc taccttaggc tgacagcagt ctcctgaaag aaagagttca agaaagaaac    2640
atttaaaaat aaaaatgggg aggggtccaa gtagtatttg aagccatgaa atatcttgaa    2700
tatagtttgc ttttttgttt tgttttgtct gtctgtctgt ccgatgtagc tttggccata    2760
tcaaccaggc tgtccttgaa ctcacagaaa tccacctgcc tccgcctccc aagtgctgga    2820
tgcaccacca tgccagctag tttgctttt agagcatctc atctgctgct cacagccctg    2880
gtgctttatg ggatttgttt ggggaacatg atgagctcta tatttattgt agctttaaat    2940
ggacagcggt tattgactgt cagcttagtc tttaaaatct ataatcacat tgtacctaat    3000
tgtcaacctt catgttttt aattatgaaa aaaactgaga acattaattt ttatgttatc    3060
ttgttattga ctttattgaa atactacaga aaattttggt ttgaggcttt tccataattt    3120
acccttacac ctcacacccc ttccataaac atgtgcagtt aaaattgaat tgttcgggca    3180
cttctacctt gatacctggc ctacagtggg aaaggtctgt ctttctttgg aataagccca    3240
tcagtggcct tgtgtacatt ctgtattttt gttgtttgtt attactgttt tttacttggg    3300
actaataatc tgtttgaaac tgactgagat agaaagatgt gatgttcctt cccactcact    3360
ccggattttg atagaagact tgtttttattt atttccaaaa ttatatccgc aggaaacaag    3420
ctgtttaaat tcagattatg ctgaagcaaa atggtcctgg tatgagaagc aacgtgctgt    3480
tttacgagca cagagtccct tttctcataa ctgattgata gtaaatattt tcctgaagaa    3540
ttattgccaa ccatgaacag tgcaactgtt tcacttttttt tccgtgctac ttgctgtacc    3600
```

-continued agccattgtc ggtaattaa                                                       3619

<210> SEQ ID NO 36
<211> LENGTH: 1114
<212> TYPE: DNA
<213> ORGANISM: Artificial Sequence
<220> FEATURE:
<223> OTHER INFORMATION: Transcription regulatory element B

<400> SEQUENCE: 36
gatctgaagt ttggatctgc agaacccaca caaaggccta cgggcttagt agtgtacctg        60
caatttcagc acttggaagg ctgagaaagg atcccaaggg cagctggcta gctaggctag       120
tgttagctga gagctctggg ttcgtggagc gactctggtt cagtgaataa gatagagagt       180
gacatcagct ttgggcttcc acagcaaatg agctcacttg catgcaaaca gaaatgcaaa       240
cacatgcaca aagcaaaaca aaaggaacac aggccaaagg tgggtcattc ctataccatc       300
ccctcagcag ggtgcagtcc ccacaccctg acccagttcc ctcatgatgt tagagaaaat       360
aactttgccc ccttcaacga acatttcagc tccagagaac ctggcccact ttgaaagctt       420
taattagaaa tgtgcaatta cccggaacag atgtctgttg tgattgtgga gacataggtt       480
aaagaatcac acagcagttt gcgtggttac agaaaggttg caagtaactt taaaacacag       540
tttttggtaa gtctccaaca tgttacctaa catagcatgg cctcgattac atgtaagcag       600
tgagtctccg gctgcctggt ttgtgagggt aatgtacttc agcaatagtg ctgaggctgt       660
acagtgagtg actcatcacc ctaaaaaagt atcgaattcc agtcttcaga gttagctttc       720
agtaaaacca agtcagtggt gaaatggctc agtaggtaag ggcacccgct gccaagccca       780
agacctgtgt cctgtccctg ggatccagtt ggtggaaaga gagaacggac tcctgcaagg       840
tggcctctga cctacatgcc tgaattctgc cagacattaa gtaaaaacaa acgcaaaaag       900
ggaagtgggc tcacgcataa ggcactcact ggactctact cttctactct gtggttactt       960
tttggtgttc aagcatacca taccttgatc tacatgattt ttactccaaa gacacagcca      1020
gggtaatgtt gtgtgatgga tcagtcttat ttgttacttg tttactagta cttactgaga      1080
ttgtcgatgg ctttaatgtc aacatgagtg tgga                                  1114

<210> SEQ ID NO 37
<211> LENGTH: 4068
<212> TYPE: DNA
<213> ORGANISM: Artificial Sequence
<220> FEATURE:
<223> OTHER INFORMATION: Transcription regulatory element C

<400> SEQUENCE: 37
gatcttctag gtctggctct gagttgaaag gctctgatgc tgggcgaaac atctctcctc        60
tggggctcag ttttctcatc tgttagaaaa ggacacagct gacctgttgg cttctaatag       120
ttggacagag gctaggattc tgagtctcat tttactacaa atattctttt aatttcttaa       180
gtcactaaac agcatcagca aggcagggtc gagacatgcg agcaagaatg agattggatt       240
ctgactcagg tttcaacttg ctgtcaatta ctgacaatgt aagttcattc atcttataga       300
cttttgtaga acttttgttt ctctccacta taatttcgtt actgttccat attacagtat       360
gctaaagtta atggtaaaag ttctcacaga attcctagtc ttttcctctt catatttaat       420
ctcctttcct tcctcctgtc cttactcatt gtgaaattct ctttttgtatg catgacttgg       480 aaacatattt cctggtggt aaggtagtag gagacaattt attcactttt cacgtatgtc       540

```
gtaattggca tattgctgat aaagttttc aaccatggga acatggtctt gtaagaatta    600
tttcacattt ttcccagtcc aagcccataa tgaaaattga ttctgaattt tttctgtatt    660
tttaattctt ctgtttgcag ttgtaggaga ataaccctgc agcatctgag agaccaagct    720
aattacaaga atgactagaa atcctttgca ttttaaaac aattttatac atatgtcact    780
ttgtctttct aaaaaataaa aataaaaaaa atacctaaga gccgagtttg tgttaaaggc    840
taatgattgt attgtacaat tagtaagaat taaggacaaa ggtctcttta cctgaagttt    900
cctgggtgct tttattcatt cattcattca ttcattcatt cattcattca tttagtcaaa    960
ttagttcatt tctgatgcaa tgactgactg attactcccc agaccaatgc tccttcctgt   1020
tttaggttca cagatagcat ttcctacctt ctcttgtcct tccttttgtc caaaattttg   1080
agttctagac aaccacagaa ttgcctagaa atgctggaca gaattcatgc atctgattcc   1140
tggtaagacc gtcgatgcac tataaacttg cagaagctga cagcagactg ttcttcactt   1200
caactcattt atccctttcc tttgggttct gtccaaatca catcaccaga tcacaagaac   1260
ctaacatcag attgagacgt aaatagatga tatcacattg gatttccacc attgagccac   1320
accaccagcc acctgcctga taactttcac agtcccagaa gatattatac aagttactag   1380
ggcaaaaaga gatcaaagtc tgaatcagct gtgaacccta tgaatggcaa tacctactta   1440
tcaggcaata caagcccacc cgtgtgatag tggaataaca gtaatatggg caatcactgg   1500
attgagtcct ggccccactg cagagaatcc atgccaagca ctgtaaatcc aggaagaaaa   1560
aaaaaaacct atcactgaag aagacataaa ccctagaaag gaacttacta ctcttactta   1620
actgagtgag caaagcaaca agttatcttc taagtactta tgctggtgct catacacaaa   1680
attatccatc attcttaatt agagaattct ctctagtgaa tggttgtgga ttcaaagact   1740
cataaatacc aagggtgcta agaatgagcg acaattaaga actcagccct aaacaagatt   1800
tttatacctc atcttctaag gctcagaaac attgtggaag aaggtgtcaa aagaatgtaa   1860
gagtgaaaag agtgagaagg gctgccaata tcatctttgc tatcatgaac tcacaaaagc   1920
tgcagttgtt agtgccagga ctgtgtgaca ttgtcactac caacactcag ccttgggtgg   1980
ggaggagggc ataatgtcat actcttcatc attgagccat tggttactaa cagattctag   2040
gagaatcact ctctcttgtt atgtatccat ccatgaatct acaaggctcc attgggcagt   2100
tccaaactgg aggtcagaaa aatttcactg atgaaactca ctgggacaca atcaaaaata   2160
tgaaagagct ttgtagccat cttttttct gacaagggtg ggagaggcat aacaaggaag   2220
gtaaataatt gattgcatta tatacacata tgaaactgtc aaagaacgca atttaaaaag   2280
tacatagtaa gtggtttcc atacaattta atttattatc acacagttgt tctttacagt   2340
atgtcttgat tatctctatc cctgactccc atgtcacccc cacaaacacc ctcaatatat   2400
ctccctccac cttatcaccc cttaatttct ttcattttac tattttatag ataatccact   2460
gaattcaatt agtgctgtct gttggaaagc cgaaggagac cgatatgttg gcttgatttg   2520
acacaggtct tctgcaggtg accaagatga agtgacttga atgtgatagc catgctatga   2580
aaaagagggc ttcatgtatt gtatcaaaag ggagcgtttc tcagctcctc tctccagcct   2640
ctgtctcata ttctttctgc tccgtcttcc tctgtaacat agtaaatttg tacagaacgg   2700
tcacaagtca caaatttggt agactacatg atgaaatttg caatgacttt ggagtactta   2760
acatggattt gaatgtccat ttggcatcgt tctagaagat aagtccaaag taagtgtgct   2820
atcttaccat cttccttcct tgtaggagtc ggccacgttt cccactctag accttagctc   2880
ctctagttag ctgcttcaaa gcatcaagtg gagtccgcat aatcactttg tactaattca   2940
```

```
taagctcata aatccagaca aagtgaaagt caaatctcaa gtcctgggcc acttatttgt    3000
tttctgtgca tcggacttag gattatttgc cctcttcctg ttccactgca tcagttctgt    3060 cagtggggggg ggggggggtt gggagtgtgt gtgtgtgtgt gtgtgtgtgt gtgtgtgtgt    3120
gtgtgtgtgt tgcttacaaa gctgtcataa tgatgaaaca gagtatcagt cacatggtaa    3180
ccacatctaa gtagagaatg tgcttctaca atgtgagctt cctctcagtg tgtccatgtc    3240
atcatagagg aggcttcttt cccagtgcac atgaaggctt cagaactaag tttgaatagg    3300
actatgtgat cagccctgaa aagcctgcag tactccttgg tgctgtgctt gaaccctcct    3360
gtttctctgc gcggtctttg tagggagact atggatataa actatttggg tggtctcttt    3420
tttttcatca ggaagacaga ggtatactgt tgattctaga catgtcaggt tgaggaaatg    3480
gaccttatgc ctaattcctt cctaattcat acagagtttc agctttaaag gacagattaa    3540
tagcggtttg agatgatttc agctctgtga cctggccatt gtgctgtgtg ttagatttcc    3600
atgctggtaa gtgaaacaat tttagggctc taaaaactca cttcaggctc taagcagcac    3660
tccacctagc cagaatgggg gagatgcagc taaacagctg ctcatgtgag cagggttacc    3720
aactccagtc gacagccagg ccagcatgac tcaccagtgt gaaactgcca agaggataat    3780
ttgatctggg gctgaatgaa caggactgca gtgtctgtcc agaccaaagt gagggatcct    3840
cccttgtctg catgtgaatc cagaccacac ctactgtctt gtaggctttg cttacccccca    3900 cccctgtatc tcattatgat gctgttcaca agttgaagta gagccagcta tgagactcat    3960
tgcataatat tcacattaga aaccactctc ttcattctat ttctatcata ggatttctaa    4020
cttaacttgt tgaaggtgtg gatattgaca tctttgagaa gaagaaga    4068
```

<210> SEQ ID NO 38
<211> LENGTH: 3949
<212> TYPE: DNA
<213> ORGANISM: Artificial Sequence
<220> FEATURE:
<223> OTHER INFORMATION: Transcription regulatory element D

<400> SEQUENCE: 38

```
gatctgtgta gctgccacaa cacttgatct cggagtgagg ccctaactcc attgatgggt      60
gtcagctctc atcagtcgca ctgttagcaa caggagatcc agctgactgc ctctcaagtt     120
atacagtgtg tgcaccagct tccaccacag cagctgctgc tgtcagtttg gaaataaagt     180
tcattcctac cttgcaggca ctttggcatt tgctttggga ttatttgcac ctcaggaaga     240
tccatcacta gtttttcatta ttctgaatgc aatggattat cagcctgtaa ataatcaagt     300
agacctcact ggatttaaac attggaagct aagctatcaa gcagatttat gaagttcaca     360
tgcttgtgca atgtgagaag ctgacttttt ggagctgcag tggcagccaa ccaagcagcc     420
tgaggtttgt tcttgaaagg gagagtgtgg actaaaggaa gcctagaaag acacagaata     480
aaatcaggag ggcagatcca gttaatactg aacaccacaa gtttatttct caccactctc     540
atatacctta accaaaaggt gaacatgagt tccttcatac aaagcaaaca ctcttttctt     600 gctgaattt tcaccaattt ggtaaccata ccttagattc aaattctagt tacctgttct      660
ttagggacag gtgtcagcac atctcagacc aagtctgttt ttatttagca taagacaccc     720
catgccatga tgcaatatcc tactgtagcc acacctttga cctttaggtt ttatgatttc     780
ctaaggacag ttatgaactc tctgcccttg agccaagatg gagtccagcc gtctttatgg     840
gaactagcag tgcaatgtga ttctctcatc cattgcattc gtcaaaaggc aattgtgagt     900
```

-continued

```
aaagggagga tgtagtggtt catctatttg cctgactgat atcctaacag ctcccctagt    960
ttttaatttt tttttagttc ttgtgaagat gtcatggctg gtctggagct cctgggtata   1020
ctgtagccta ttttactgtc taagcctctg gggtagctgg gattgctgga tcatggtgac   1080
aggtaactca ctacccaatt ttaaagtgaa tttgtaatga aaggatgatg attgttacct   1140
acttgttagg gctaggaatt gatttcttcc caacatttta gagattttcc ctgtgtatta   1200
atggcattta tcttgcatct acaattgatg ctgttcaaag ctgcccaggc tggcctctaa   1260
ctcacagaga tgcaaatgcc tctgcctccc gagtgctggg attaaaggcg tgcaccacta   1320
atgcctggct cttttttaaaa tcttttaggt tattgcttcc taagctctag tgactatggg   1380
tagatatcaa agacaataca gttttcattg gttctgtttt ggtgtgtagt ttttgttggc   1440
tactttcttc tttacacaga tttcatgtag tgcacactca tcttgagctc tctacatagc   1500
acaagaggac cttgcaggct tgattatcca gccgctaatt cctaagtgct gagtgacaag   1560
tgtgtgacac tgtgcctctc attttgttgg ttattttaga aagagtctta ctaagttgcc   1620
cagactaggc tcaaactctg aatatctccc agctttagcc tccatagtct tgcatttaca   1680
ggcagtttaa tcttgagcta acagtccctg ctgataccaa gtttttattc taggtgtcca   1740
agaggaactg tagcagtgaa ctccagtcta gccaaagaca cttgaccatt gcactctgga   1800
tcttgtcttt agatatgtat tttgggggat ttcttttttaa tcaacaggaa atcaaataaa   1860
cttaaaaaag aatttacgca ggcagcactg gttcaagtat ttaatctcaa caccctgtag   1920
atataggcaa aagtatctct gagcagaaag atagccaggg ttacaaagag aaaaactgtc   1980
tcaaaaatta tatatatgtg agtgagtgtg tgcgtgttag ttattttaaa ttatatgtat   2040
aaatgtacat gcatatgcaa gagcccatgg agatcaggag aaattgtgtt ctctaagagc   2100
tgtagttact ggtgggtgaa agccaccagg gttgggagag agaaatagaa ctgtagtact   2160
atgatagaac aagaagtgct cttaacctga gttatggttc tagctcaata gatacactat   2220
tcacagttat tttaaagata ctgttgttgt tgtcttttac tgtgcatttg ggtgataaaa   2280
catgatccaa cacactcaac aaatccacat ggagtttatt ggaaaaggga ataaagggag   2340
gggtaggtgt taaccaatag ggagcagaaa tggaaagaga gaaaacagat gggaggcact   2400
tgcttataaa gggaaaggaa acagttaaga atgaggctca gtagttgggg cctttgaaac   2460
catagtcact gaactgcctt tggccaagat ttacatggtc tctgtatgca gaatcctaat   2520
tcagtcaatt aacacatgca ccacacagcc atgcaaactt tgacagtctt tgagatgtca   2580
gcaaggaaca atcacctgtg aaaaacagat cccagggcaa gggcaggtca cctggaaaag   2640
agaagagaag atggatccca gagcagggag ggaatccaag tgttagagag gccactaggc   2700
caggaaagga tctctaagga agcaacaggc ccaggagagt gctgatgtgg agtgacatgt   2760
ggagatcaag agaaacacc agggtgggag gagagaaatt ggcagctgga tcagggccag   2820
gtcgcacaga acctagggag agggagaatc caggttatca acaattatta ctaggcagta   2880
ctacattttc tgtgtcctat tatttctgta gttacttaca aaatatttga gttataaaaa   2940
ggaataaaga gccgggcagt ggtggcacat ggcattaaca ccagcacttg ggagacacag   3000
gcagttgcat ctatgtgagt ttgaggccag cctggtctac agagggagtc ccaggaccaa   3060
aagccacaga gtaactttgt catacaaact gatccagtag gcttcatctc agatacgcag   3120
tgatggttca acatacaaaa atcagtaact gtaatccacc ataaaaataa actttaaaaa   3180
acactttttt attatcccctt tacatgctta caaagtcatt gataagccag gtattggggg   3240
tgcatgcctt taatcccagt acttgggagg cagaggcagg tggatcactg tgagttcaag   3300
```

-continued

```
gccagcctga tctccagagc gagtgccagg ataggcttca aagctgcacg gagaaaccct    3360
gtcttgaaaa accaataaat aaataaataa ataaatagtc attgacaaga aacaaacatc    3420
ataaaagtct tggagatatt atggatacaa tttacataca cacacataat gaaggacatt    3480
tacagcaaac ctatagacaa catcaaatac aatggagaga aaaaacaaag gaattcctat    3540
aaaatctgta acttgacaag tttgtgaagt ctatatctac tcaatacagt acttgaagtt    3600
ctagatagac ccattaaaca gctaaaggac aacaaggaaa ggaagaagta gaagtgttgt    3660
tacttgttga tgatatagtg gtaccaccta agtgacacta aaaattcatc aatggaagta    3720
caggtgatta aaactttcag caaagtgacg ggatacaaga gtaactaaaa caaccattag    3780
ccctcctatg taaaaatggc aaacagcttg agaatgaaat aaaagaagca gcagcaatca    3840
caatagcttc aaataatata aaatacattc tagtaactct aacttgttta attaaaaaaa    3900
ctttaagtgt ttgaagaaag aaattgaaga agatatgagg cgatggaaa                3949
```

<210> SEQ ID NO 39
<211> LENGTH: 1128
<212> TYPE: DNA
<213> ORGANISM: Artificial Sequence
<220> FEATURE:
<223> OTHER INFORMATION: Transcription regulatory element E

<400> SEQUENCE: 39

```
gatcaggagt tcaaggccac actgaggtac acgaaattca accagtctga tagatataag      60
agctgggtgc gtgtggctcg cacctcaggt ggagacagga gtataaggct ggaggaggca     120
gtatttaggc ttattcatat agaggatttg taaagacagg acctccccag cacttccatc     180
tgaacatttg gtacaggtaa gaagtcccta tagagttggc tcctttaatt ctcttatgtc     240
tcaacattta cccaattatc tgacatctca ctcagcgttt ttactattta aaccaatttg     300
aagaaatgct acagagcacc ttttaacctc tacaaacaca cataaacaca gagagagaga     360
gagagagaga gagagagaga gagagagaga cagagacaga gacagagaca gagacagaga     420
cagagaaaca aatgtaataa cgaaagaagt catgtcatga gaaccctgag gctgcggtcc     480
acacccatct gtggccagga cacagaggcc tagaggagcc ctgtgacaca agcactctct     540
acaactggcc cttgtcccgt gcaggggca gaaaggacag attttgttgt gcagaagctt     600
tatcatcagc agcatacact gggcctctct gtccttcact gtcacatgct cctagggagt     660
tcagtcggga ggtcatgtat gtgcactatg gacctgtccc acagacactc tgtcctaatg     720
cgttctgctg gggtattttg gcaatgctgc aattgagcag tgatgtttca aggtgcacta     780
gttgttcccc ccatattctc caacacaatc aatgccacat tgtaaatcaa aacattcagg     840
ctcccctgtg aattgtaagg attttattat tggaatcctg gttttagata cctggagggt     900
agggtagggc ttgcttcatc tattcaggtg tgtaggcaag tggctccctt gagtcttatt     960
gcccagatgg attcatcaac agaatttgtt agcatctatt ttctgctgca aagagaaccc    1020
ggtgaggtat ctgaggtgtc agaggtgaag gacatctcac tgagcataca tgggacacct    1080
catgggaggg actgaaacct gtctgccaga gcacctgggt ctgaccat                 1128
```

<210> SEQ ID NO 40
<211> LENGTH: 1352
<212> TYPE: DNA
<213> ORGANISM: Artificial Sequence
<220> FEATURE:
<223> OTHER INFORMATION: Transcription regulatory element F

```
<400> SEQUENCE: 40
gatctctcag cttcctgctt tttaaaagta ttttatttta tttttatacc cattgatgtt      60
ttttgtcgtg ggtgtcggat accctgaaac tggaggtttt cattttatat ttatgttaat     120
caatgttttg ccatgggtgt tgcgtcccct gaaactggag ctacagacag gtgtgagctg     180
ccatgtgggg ctgggaactg aacttgagtc ctctggaaga ggagtcagtg ctcttaacta     240
gtgagccatc tctctaggcc ctcagcttcc tgctttggct accagctgac atgcctctcc     300
caccattatg aatgcccct caggaacctc tggaactgaa aaccaaaata aacttttaa       360 agttgcttta gttcatggca ttttatcaca acaatagaca agaaactaat acagtaatac     420 atggctttt aaatgatttg acagattcat gtaagtatat agtgaatttg ggtcattttt      480
caccctttaa taccattgtc atcctccttc ctaaccagct gggaccctct tcctcagcag     540
gccctcttct actttcattt tttttttttt tttttgtgtg tgtgtgtgtg tgtgtgtgta     600
tgtgtgctcg cgcgtgtgct gtgtccttat gtttatttat ataaaaaata gcgcattgac     660
tctaactttt actacacctt actggttata tatgtatgtg tatgccatgg tacatgtgca     720
gagaacaaag gacaactttc cgggagtcat ttctatcctt ccactatgca tgtggtttct     780
gggatagaac tcaggtcatt agccttggca gcaagcctct taaccctctg aaccatctcc     840
ctggcctggc attttaaaat aatctttgat gcttctatca gtatcttggc cactgataat     900
ctataattat ttctctaaga ctatttgttt tccacaaaca aaatgctata agctgggaga     960
tttataaaga agagatacat ttggctcaca gctctggaaa ctgggaagtc caaaagcatg    1020
acaccagcag ctgtcaaatg cctttctgca gtatcataag aaatcagagg acagcacatg    1080
acaagaatgt tacaaaagga caggacaagt gttccaggct tggtctatgg ttttcatcat    1140
ttaaggccgc caattccatc acaagtgttc tcttccctat gatttcatgt aattctaaag    1200
acattctaaa accccacacc caaatactat tagcacaaga cattggagat tttagtttca    1260
atcttagctt taggggagag acactcagtt cataacagta tccccaagat ttccagtatc    1320
cagtgctgtc tcaatgcaat actactcaga ag                                  1352

<210> SEQ ID NO 41
<211> LENGTH: 1246
<212> TYPE: DNA
<213> ORGANISM: Artificial Sequence
<220> FEATURE:
<223> OTHER INFORMATION: Transcription regulatory element G

<400> SEQUENCE: 41
gatctttcca ttttctggta tcttctttaa tttctttctt ttaagactca aagttcttgc      60
tagacaggtc tttcacttgt ttggttatca ttaccccaag atattttatg ttgtttggct     120
attgtaaagg atgatgtttc tctgatttat ttctcagccc atttatctcc tgtgtataat     180
agggctagtg attttttgag ttaatcttgt atccttccac ttagctgaag gtgtttatca     240
gctgtagtag ttccctggta gagtttttg ggttacttat gtaactatca tatcatctgc      300
aaacagtaaa aatttgactt cttcctttcc aatttgtatc cccttgttct cctttttgtt     360
gtcatattgc cccagataga acttcaagta caagcagaag tcattctctt ctgcttcatc     420
tgtgttggga tgttcaggtc ttgctggcgt agagtcccta gattctagtg gtgtcatatt     480 gtttttctg ttattgaatg cgttttata ttgttgtctt cccatctctt cttccagtgg       540
gttcaggtgc cgtctcttcc tctcctggtg tgtatgggtc caaggttctc tttggtggat     600
gcaagagggt ctgatactct gatgggtctt atggtgggtt caggcgggtc tggggcactc     660
```

```
cctctctagg tgggggtggg aactggacta gcacagtgat gtcatcagac ttgaggttgc    720
ttggtcctca gggggcaagt tgatttgcct gcagtcccca ggacaggagt tcccagagtg    780
gacaggcaga agtcgggctc aaggcagggg ccaagctcta catgtgattt ttaaaatgag    840
agttcagatt catgtaggca gatgataagc tcagggagaa aaatgaccta tttctaaaaa    900
ctgatgacgt gaagattgag agaaagggtg gatttttgaa aaagaatcgg tagggagcta    960
aaaaggaaaa gagaaattaa ggatgactct caggtttttgg acttgaatgt tggatggatg   1020
tttgtcccat ttgtagaaag gagaacacag gtgatttaga agtctgaggt gaggatgtca   1080
cctcatgact taaagaatct gaggtttttag aatcaaatct cagggaacat cattagcaga   1140
gggaccctgt tgggtcttgc cagatgctga gcttcagctg tctcctgttt tcccacattt   1200
cctgtttttc ctaacttgta tagactctgg gaaaagaagg taccag                   1246

<210> SEQ ID NO 42
<211> LENGTH: 1886
<212> TYPE: DNA
<213> ORGANISM: Artificial Sequence
<220> FEATURE:
<223> OTHER INFORMATION: Transcription regulatory element H

<400> SEQUENCE: 42
gcagtacaac atctcttgct ttgctcggga atgtgggcac tctgaatgtg atcctgaccc     60
ttttgggaat agagcaggtc catccgggac ttcaacccat agaatctaaa catgggaaac    120
catatttatc aaggtctttc tagcagctac agaatcatct atcctgctac tagactcaga    180
gcagaggcta caggaggtgt cagacagaac tcactttaga gtcttcagta caagataagc    240
ttcaggccag acctgcttcc agctctccag gctttccaaa gaccaagtgg gttggagaga    300
actctggcct agcaggcttg aaagaaactt ggttgggact gttaacttca gtcaatttgc    360
tccttgcagc aggtattgtt aacatgaggc agagatggga gggtgaaatg agagacaatt    420
ggtcagaact gttgatgccc aaagagctat ttaactaatt aaaacaattt aaactgttaa    480
gaaaattttt gtggttttat tgtatcatga ggcattgaaa catctgaaca aatcaatatc    540
tgggcggtga ggcagctgct ttctccttca cttctttggg ttactagagc aacttgtcag    600
tagattaaaa aacaaaatga aacaaaaaca aaaaccgaca atcttttgca ttacttaagt    660
ctttccaagg catgcgctgg tacaaacaaa acttctcctg tcagatgcaa ctagtctagc    720
atccaaacat catgcacaac accgtggtga cagaagcgca ctgcacctac tcccacctcg    780
gccctgctca tttgtgtatg atatttggag catctggagg agtgagatag tattgggaag    840
aggagggagg aggaaacagc gtgaggatct ggccaggtgg aggtcagccg aagttgtgca    900
gggcaagcct gaacatgtca ttggtgcaaa cccaagcatc gttgatgttc tttaatagaa    960
acatctggtg gaaacccatg atgggatctt catcggcctg tatggaagaa aaaatgattc   1020
agtaagaggc taggaacag gaagaacgtt cagtggtaga acaaggcaga gaatacagac   1080
tccaggatca ggcacctact ctcttaaacc cgaatgccag tacagaacag gtacttgtga   1140
atgtgaactg ccatgtgtga aacattgttg atcatgcaaa agtcaataaa tggctgctca   1200
cactgccatg tatcattgaa aaggcagcac atttaccagc taactaggcg acagagcaga   1260
agacttgcct gtctctaaac tcggcaatgt ctctgggtag atgtgatcaa agaatgtaaa   1320
gactcttgta gcacttatta tttaatttat agtaccaaaa aactgtaagc aatcttagtg   1380
ttcaagagga actgacagaa gagtaaggct ggacttgtag gtagtgcttc tgggtctaat   1440
```

-continued

```
aaagaggcac agacactctc tttccacaca cctattgccc gcccctctcc acacgcatat    1500
cggattcagg ctcagccaat ttgtcctgct ttaggaagaa gctttggaaa cactatcaaa    1560
ctacgaagga accagacaca gggacacaca ccttaaaaag accaaggttg tgctcaaagg    1620
gtaaaggcac ttgccctata agactagtga tacgagttgg aaggagagag agatttcctc    1680
tgacctttac atgagtgttg tagcatacac agaatacact catcatgtaa acacacataa    1740
catatgcaca atgttgcttt ttcactaaat tcttttcttt cctttttctt tttttggttt    1800
ttcgagacag ggtttctctg tgtagctttg gaacctatcc tggcactcgc tctagagacc    1860
aggctggcct cgaactcaca gagatc    1886
```

```
<210> SEQ ID NO 43
<211> LENGTH: 1118
<212> TYPE: DNA
<213> ORGANISM: Artificial Sequence
<220> FEATURE:
<223> OTHER INFORMATION: Transcription regulatory element I

<400> SEQUENCE: 43
gatctgaagt ttggatctgc agaacccaca caaaggccta cgggcttagt agtgtacctg     60
caatttcagc acttggaagg ctgagaaagg atcccaaggg cagctggcta gctaggctag    120
tgttagctga gagctctggg ttcgtggagc gactctggtt cagtgaataa gatagagagt    180
gacatcagct ttgggcttcc acagcaaatg agctcacttg catgcaaaca gaaatgcaaa    240
cacatgcaca aagcaaaaca aaaggaacac aggccaaagg tgggtcattc ctataccatc    300
ccctcagcag ggtgcagtcc ccacaccctg acccagttcc ctcatgatgt tagagaaaat    360
aactttgccc ccttcaacga acatttcagc tccaagagaa cctggcccac tttgaaagct    420
ttaattagaa atgtgcaatt acccggaaca gatgtctgtt gtgattgtgg agacataggt    480
taaagaatca cacagcagtt tgcgtggtta cagaaggttg caagtaactt taaaacacag    540
tttttggtaa gtctccaaca tgttacctaa catagcatgg cctcgattac atgtaagcag    600
tgagtctccg gctgcctggt ttgtgagggt aatgtacttc agcaatagtg ctgaggctgt    660
acagtgagtg actcatcacc ctaaaaaagt atcgaattcc agtcttcaga gttagctttc    720
agtaaaacca agtcagtggt gaaatggctc agtaggtaag ggcacccgct gccaagccca    780
agacctgtgt cctgtccctg ggatccagtt ggtggaaaga gagaacggac tcctgcaagg    840
tggcctctga cctacatgcc tgaattctgc cagacattaa gtaaaaacaa acgcaaaaag    900
ggaagtgggc tcacgcataa ggcactcact ggactctact cttctactct gtggttactt    960
tttggtgttc aagcatacca taccttgatc tacatgattt ttactccaaa gacacagcca   1020
gggtaatgtt gtgtgatgga tcagtcttat ttgttacttg tttactagta cttactgaga   1080
ttgtcgatgg ctttaatgtc aacatgagtg tggagatc    1118
```

```
<210> SEQ ID NO 44
<211> LENGTH: 1611
<212> TYPE: DNA
<213> ORGANISM: Artificial Sequence
<220> FEATURE:
<223> OTHER INFORMATION: Transcription regulatory element J

<400> SEQUENCE: 44
gatcttttgt ggactcagaa ggtcgctgct tctatgagca gctggagaga ggaaggagaa     60
ggtctttttc tggtcttctt cagcaaggtt gtcccctatc cacagccctc atccgagtc    120 aaagatgaga tggtaggaac ttacatatca caagtgccaa ggcagggac agtcagctaa    180
```

-continued

```
gccaggtttc cttaagtact gtgggggctc tgggagaatt gagacctgtc ttaccctgga        240
ccaatggcca ttcaggatat ttcatgctcc agcaagcatc caatagttca ttgatatcct        300
cccaccaagg cagagttttg gatggacttt tccacctgta tggcctttca gtgtggcaaa        360
ctttcatacc tgaaattcag gcaaagctcc tgaagtttgg aaaacccagg ccttactggg        420
ctggtcaact ggtctacatc tccttagtga tgacaatggc atgtcctccc atccctctga        480
ctaagctgcc acaatgttcc tctgcctgca gcctgggttt ctcagggata tgtctaggta        540
agtcccctac agctccaaga ctactgtcta gcataaaagc tttgagaaca agactgagag        600
tttagaggcc ttcatgcaat cttttgggga catcagaccc agatgtcatg gctggggtca        660
catggtagtt gagacccatg ccctgcctgg actccatgca aggtcagaca gtgaactttg        720
gggacagaag ttgaagccca catagagccc tgccagtgag ggctacaaga agaagccaaa        780 cccctttgacc aatctgtacc tgaacccaag aagaaccagt tggaggagcc aggctgggaa        840
atggacccct aagagatttc ctaggcagcc tttgctttcc ttgttgcctc aggcctgata        900
tggccaggaa gggaagcacc tgtctatagc ctagaccaca tcttatcact ctaaggtgga        960
accagatgag tgtccaccaa ctagcctgac tttcccctg ctgagaactt actgtgtgca       1020
ttgagcactt actgtgaaca tcctattagg taatccacca ctcttattcc cacccccca       1080 gactgttagc cagtacaatg gctaggtggg tggcaggacc agaggagcat agttgtatgt       1140
ggccctgtgt atcaggctca gactgcaaca tctagtgggc taccagtggc ctaacactag       1200
ctgcctataa gaataggtat gcccttgcct gttttcattc catctatagt ttcttcattt       1260
cccttggaat ttttagtaaa gttgctttgt ttttgtttgt ttgtttgggt ttttgttgtt       1320
gttgttcagt tgggcaggtc caaaagaaag aggcctctgg ctgtgtagct ctcatactcc       1380
tcagggcctc tttctcatga gtgcacctac ccgataccaa cctctctcct agtacctgga       1440
gaagcaaaac ccagaacagg aaaataaagg tcaaaataga ggtcataggg aagaagcagg       1500
cctaatattt aacactttta agaataacta actgggttga ctgtccaaaa gccgcacatg       1560
tctaatggtg ttgaatgtcc attcttatct agaaattgct tagaagtgat c              1611
```

```
<210> SEQ ID NO 45
<211> LENGTH: 1299
<212> TYPE: DNA
<213> ORGANISM: Artificial Sequence
<220> FEATURE:
<223> OTHER INFORMATION: Transcription regulatory element K

<400> SEQUENCE: 45
```

```
cccttgcaca taagcggcat gtgtccccag cctggagggc tacgtgtgat attttccccc         60
tggcatgtaa gaagtcttca gtgggccagc aaaatgcttt ctatgaaagt ctgtgacact        120
ggcgtgcact taccctgctt gtagaaagta aattggcctg tttagccatg caatgctgtt        180
ttagttgcag cattcctaga gtaaaaagaa cttttgatgc cattgaacct aaagctcaga        240
aatttggaat gtaaagctgt cattgcaaca cacatttcta aatctttacc catgttttgg        300
aaaatacaat aaattcagaa attgtcagta actgaattgc tatgtcttaa aagcatttac        360
tattgacatg ttttgggaga attaaagtta gcttggaaat ttaaaaaaaa aatgaagaat        420
tcaaacatat tgaaaaatag attgatatta gtaaatatta atatctttta catatagaag        480
tgtcatagtg ccactctatt acattgaatc atttagactt gttattttca tagatttatt        540
ttataaattt attttttctg ctaatctttt tattttaaat tggttcttca caatcttaag        600
```

```
tgacaaaata ttctcaatat tggcaattat atattgcttt tatatgcaaa tttaaaatag      660
gatacataaa ttgcaaatta attttgttac tgtaggaatt atttgaaata tactggctgt      720
agtcactaat gtagatttac aggattcatc tttcaccatt gtagttctgt acccattctt      780
gatgaaaaag ggtagatttg accaactccc ctttaatagg gtttcatttt ggttttgtca      840
gagattaaag tagcataaat cacattaaca tggaaaaagt acaatattta tttagtgcaa      900
ttttgtcagt gccacccaaa gacaagataa acaaatactt aaagaactga tgaatgaaaa      960
gcaattattt agatattgat gtagacttta aaaagtgaca agttgtgaga aaagcaacta     1020
cattttgcat gaaggcttaa aggatgaaca acttttagga tgttcatgcc tttcttggtc     1080
tctaccatta gtagaatcat tgtttttccta atgaaaggat ggattctgtc acatctccca     1140
aaaattagaa tggtcctata ttgtccattt ctcaaatatc tttaattcat aaataaccaa     1200
agtgtcaggt tgcatgacat gttttggact acttgatttt aggagcctaa tattccctgg     1260
ttacccttta aatgcaagca ccattctaat agctggatc                            1299

<210> SEQ ID NO 46
<211> LENGTH: 1108
<212> TYPE: DNA
<213> ORGANISM: Artificial Sequence
<220> FEATURE:
<223> OTHER INFORMATION: Transcription regulatory element L

<400> SEQUENCE: 46
gaagtttgga tctgcagaac ccacacaaag gcctacgggc ttagtagtgt acctgcaatt       60
tcagcacttg gaaggctgag aaaggatccc aagggcagct ggctagctag gctagtgtta      120
gctgagagct ctgggttcgt ggagcgactc tggttcagtg aataagatag agagtgacat      180
cagctttggg cttccacagc aaatgagctc acttgcatgc aaacagaaat gcaaacacat      240
gcacaaagca aaacaaaagg aacacaggcc aaaggtgggt cattcctata ccatcccctc      300
agcagggtgc agtccccaca ccctgaccca gttccctcat gatgttagag aaaataactt      360 tgccccttc aacgaacatt tcagctccaa gagaacctgg cccactttga aagctttaat      420
tagaaatgtg caattacccg gaacagatgt ctgttgtgat tgtggagaca taggttaaag      480
aatcacacag cagtttgcgt ggttacagaa ggttgcaagt aactttaaaa cacagttttt      540
ggtaagtctc caacatgtta cctaacatag catggcctcg attacatgta agcagtgagt      600
ctccggctgc ctggtttgtg agggtaatgt acttcagcaa tagtgctgag gctgtacagt      660
gagtgactca tcaccctaaa aaagtatcga attccagtct tcagagttag ctttcagtaa      720
aaccaagtca gtggtgaaat ggctcagtag gtaagggcac ccgctgccaa gcccaagacc      780
tgtgtcctgt ccctgggatc cagttggtgg aaagagagaa cggactcctg caaggtggcc      840
tctgacctac atgcctgaat tctgccagac attaagtaaa aacaaacgca aaaagggaag      900
tgggctcacg cataaggcac tcactggact ctactcttct actctgtggt tactttttgg      960
tgttcaagca taccatacct tgatctacat gatttttact ccaaagacac agccagggta     1020
atgttgtgtg atggatcagt cttatttgtt acttgtttac tagtacttac tgagattgtc     1080
gatggcttta atgtcaacat gagtgtgg                                        1108

<210> SEQ ID NO 47
<211> LENGTH: 3619
<212> TYPE: DNA
<213> ORGANISM: Artificial Sequence
<220> FEATURE:
<223> OTHER INFORMATION: Reverse complementary sequence of transcription
``` regulatory element A

<400> SEQUENCE: 47
ttaattaccg acaatggctg gtacagcaag tagcacggaa aaaaagtgaa acagttgcac          60
tgttcatggt tggcaataat tcttcaggaa aatatttact atcaatcagt tatgagaaaa         120
gggactctgt gctcgtaaaa cagcacgttg cttctcatac caggaccatt ttgcttcagc         180
ataatctgaa tttaaacagc ttgtttcctg cggatataat tttggaaata aataaaacaa         240
gtcttctatc aaaatccgga gtgagtggga aggaacatca catctttcta tctcagtcag         300
tttcaaacag attattagtc ccaagtaaaa aacagtaata acaaacaaca aaaatacaga         360
atgtacacaa ggccactgat gggcttattc caaagaaaga cagacctttc ccactgtagg         420
ccaggtatca aggtagaagt gcccgaacaa ttcaatttta actgcacatg tttatggaag         480
gggtgtgagg tgtaagggta aattatggaa aagcctcaaa ccaaaatttt ctgtagtatt         540
tcaataaagt caataacaag ataacataaa aattaatgtt ctcagttttt ttcataatta         600
aaaaacatga aggttgacaa ttaggtacaa tgtgattata gattttaaag actaagctga         660
cagtcaataa ccgctgtcca tttaaagcta caataaatat agagctcatc atgttcccca         720
aacaaatccc ataaagcacc agggctgtga gcagcagatg agatgctcta aaaagcaaac         780
tagctggcat ggtggtgcat ccagcacttg ggaggcggag gcaggtggat ttctgtgagt         840
tcaaggacag cctggttgat atggccaaag ctacatcgga cagacagaca gacaaaacaa         900
aacaaaaaag caaactatat tcaagatatt tcatggcttc aaatactact tggacccctc         960
cccattttta ttttaaatg tttctttctt gaactctttc tttcaggaga ctgctgtcag        1020
cctaaggtag cttatgaagc agctgtgctt ccttacagga actgaatagt tacagggcaa        1080
ccagcagagg aaaactacac acaaaatact acaggtttca tctctgcttt tgagaaggac        1140
caatgtcttc tgtaaaatgc aaacaagtaa taattaaaag gtctaagact acaattagta        1200
ttgataccca aaccaaaatt actctgactg aaattcagtt gctttgaacc ataaggggga        1260
aaaaaaggct ggcttcactg tatttcagtg gcgttacatg gagacagctg gacatgtagg        1320
ccacaatgga gaccagtttg aatcagtatc agacgccagt ttctgaagga aagtcctcac        1380
agccacgtca gtgtagcaga caaaactact gttaagaact aaaggtgaag aacaagaact        1440
agagaaatgc ttacagaact acaaaaatat ctttggagtca tttcttttaa aggtcaagca        1500
gtaaatgagg ccaggagaga cagtatgaaa tcatgagaca gatataacat gtttagcaat        1560
aagaaaggaa aactctcatt gttgccatgc tagaggaggc cactgcaata aacatttttt        1620
tcagttacgt atttttattt gatgatttgg ctcaaatctg aagcaatgaa ctagaagaca        1680
ggatgtgggc caataaaagg aaccaggaag ctggttgtgt tccaaatgga aattacagaa        1740
atcattattc aattagagtg gttaaggggga caatgaaaga aaataggtgt cagaataatg        1800
ttaaaacaag caagaatggg acgagaaggt caccatctgg gagcaagtga aacagactga        1860
tgagcagcaa tgagcaaact tatttcctca cccaagagca tggaaggaat tataccaccg        1920
tgccagacgc cacaagattt ctaaccgtgc accactgaag tagagggtag aaaaaagaaa        1980
aaagaacagc aaaaacaaat ccaccccaca ctatacacac agcaacaagg ctaaggagtg        2040
tagaaacact ggcttaccac gtacaggaaa acaaaaggaa cagatgctca gttggccagc        2100
tctcaatgaa actcattaaa aattgtcgccc tgtccttgga ttggtggtca tgcgaaattt        2160
gtgccttgtt tagccagaag taacttgtga tgaaggagag aacagcatgt ccaaacaaga        2220
attgaaacac ttgttgatct atactcaatg ctagatataa aacaggatca agtagcactt        2280

-continued

```
acaaactgtt actaagtaat tgaaaattaa atgtaactta cactactcct cttttttttt      2340
tgtagcaaat taagatgtga acttaaggca caatttgatg aacctaccat ttgcagctac      2400
aatataaaat aaattcttac atttctcata tggctaagtc caatggccac aagctgtatg      2460
tttgcagtaa taaagcaagg tcaggaactg ccatgtattt tgggaaatat aataaaaatt      2520
attgttgctc ctatgtcctg attgatcatg tccctcccta accacctaat gtgtaagaac      2580
agagtctcca tgaacagaat tagagcacta tgcaataagt aaatgaatga acagattaat      2640
aagagatccc agagggctta gctcatccct tccatcctga gattatatta tagcaaggat      2700
tccatctatg aagaagagtc aacttccaac tagacattga atctactgtc accatgatct      2760
tcccatatct agaactataa aaataagtca ctgtttataa gctaccttgt ttatttttgg      2820
ttgtaataac acaaaagaaa ttagctcttc ttgagattta taacaaagat ggagttgaca      2880
tgacatcaag tcctatctct aataatgaca gtaaataggg gcctatatag gacacaagag      2940
atgaagcaga aagttggaaa agttgtaaaa cagtcacccc ccaaaatggt aataaaggtt      3000 attttttgcct aaaaataaag acaaactcta gaaatacaac tcatactgaa cgttatcctc      3060
aagacagtaa agttaacaaa aaagttatcc ccagtcaatc tagaaaattg aaagaaaaaa      3120
attaagattt ctaattaaat ttttgtgtat gggtgttttg tctatatgta tgtctgtaga      3180
ggccagaaga agacactggg tcctctggaa cgggagctgc agatggttga gagccgtcat      3240
acggtgctga caggtaaccc gggtcctata caggagcagc ccttaaccaa tgagctctta      3300
accaatgaac ccctctccag ccctgaagat ttctaatttt taatattttt gtatctagaa      3360
atataacaca catttataca taaaagacta ggctcatatg tcagctaaat acatgtttcc      3420
actcaaaatc accaagtaag acatttctca agaaagaagg gcacaaccta agctgggacc      3480
tctgcagcag tctcacgcat gtggctcaca ctgtcaccag cagggtattt ctggcgtgct      3540
acacctgcac ttaaaggagg ccaggcatgg cggtgctggc ctttaatccc agcactcacg      3600
gggcagaggc aggcagatc                                                  3619
```

```
<210> SEQ ID NO 48
<211> LENGTH: 1114
<212> TYPE: DNA
<213> ORGANISM: Artificial Sequence
<220> FEATURE:
<223> OTHER INFORMATION: Reverse complementary sequence of transcription
      regulatory element B

<400> SEQUENCE: 48
tccacactca tgttgacatt aaagccatcg acaatctcag taagtactag taaacaagta        60
acaaataaga ctgatccatc acacaacatt accctggctg tgtctttgga gtaaaaatca       120
tgtagatcaa ggtatggtat gcttgaacac caaaaagtaa ccacagagta gaagagtaga       180
gtccagtgag tgccttatgc gtgagcccac ttcccttttt gcgtttgttt ttacttaatg       240
tctggcagaa ttcaggcatg taggtcagag gccaccttgc aggagtccgt tctctctttc       300
caccaactgg atcccaggga caggacacag gtcttgggct tggcagcggg tgcccttacc       360
tactgagcca tttcaccact gacttggttt tactgaaagc taactctgaa gactggaatt       420
cgatactttt ttagggtgat gagtcactca ctgtacagcc tcagcactat tgctgaagta       480
cattaccctc acaaaccagg cagccggaga ctcactgctt acatgtaatc gaggccatgc       540
tatgttaggt aacatgttgg agacttacca aaaactgtgt tttaaagtta cttgcaacct       600
ttctgtaacc acgcaaactg ctgtgtgatt ctttaaccta tgtctccaca atcacaacag       660
```

-continued

```
acatctgttc cgggtaattg cacatttcta attaaagctt tcaaagtggg ccaggttctc      720
tggagctgaa atgttcgttg aaggggggcaa agttattttc tctaacatca tgagggaact      780
gggtcagggt gtggggactg caccctgctg aggggatggt ataggaatga cccacctttg      840
gcctgtgttc cttttgtttt gctttgtgca tgtgtttgca tttctgtttg catgcaagtg      900
agctcatttg ctgtggaagc ccaaagctga tgtcactctc tatcttattc actgaaccag      960
agtcgctcca cgaacccaga gctctcagct aacactagcc tagctagcca gctgcccttg     1020
ggatcctttc tcagccttcc aagtgctgaa attgcaggta cactactaag cccgtaggcc     1080
tttgtgtggg ttctgcagat ccaaacttca gatc                                 1114
```

```
<210> SEQ ID NO 49
<211> LENGTH: 4068
<212> TYPE: DNA
<213> ORGANISM: Artificial Sequence
<220> FEATURE:
<223> OTHER INFORMATION: Reverse complementary sequence of transcription
      regulatory element C

<400> SEQUENCE: 49
```

```
tcttcttctt ctcaaagatg tcaatatcca caccttcaac aagttaagtt agaaatccta       60
tgatagaaat agaatgaaga gagtggtttc taatgtgaat attatgcaat gagtctcata      120
gctggctcta cttcaacttg tgaacagcat cataatgaga tacaggggtg ggggtaagca      180
aagcctacaa gacagtaggt gtggtctgga ttcacatgca gacaagggag gatccctcac      240
tttggtctgg acagacactg cagtcctgtt cattcagccc cagatcaaat tatcctcttg      300
gcagtttcac actggtgagt catgctggcc tggctgtcga ctggagttgg taaccctgct      360
cacatgagca gctgtttagc tgcatctccc ccattctggc taggtggagt gctgcttaga      420
gcctgaagtg agttttttaga gccctaaaat tgtttcactt accagcatgg aaatctaaca      480
cacagcacaa tggccaggtc acagagctga aatcatctca aaccgctatt aatctgtcct      540
ttaaagctga aactctgtat gaattaggaa ggaattaggc ataaggtcca tttcctcaac      600
ctgacatgtc tagaatcaac agtatacctc tgtcttcctg atgaaaaaaa agagaccacc      660
caaatagttt atatccatag tctccctaca aagaccgcgc agagaaacag gagggttcaa      720
gcacagcacc aaggagtact gcaggctttt cagggctgat cacatagtcc tattcaaact      780
tagttctgaa gccttcatgt gcactgggaa agaagcctcc tctatgatga catggacaca      840
ctgagaggaa gctcacattg tagaagcaca ttctctactt agatgtggtt accatgtgac      900
tgatactctg tttcatcatt atgacagctt tgtaagcaac acacacacac acacacac      960 acacacacac acacacac acactccaa cccccccccc ccccactgac agaactgatg     1020
cagtggaaca ggaagagggc aaataatcct aagtccgatg cacagaaaac aaataagtgg     1080
cccaggactt gagatttgac tttcactttg tctggattta tgagcttatg aattagtaca     1140
aagtgattat gcggactcca cttgatgctt tgaagcagct aactagagga gctaaggtct     1200
agagtgggaa acgtggccga ctcctacaag gaaggaagat ggtaagatag cacacttact     1260
ttggacttat cttctagaac gatgccaaat ggacattcaa atccatgtta agtactccaa     1320
agtcattgca aatttcatca tgtagtctac caaatttgtg acttgtgacc gttctgtaca     1380
aatttactat gttacagagg aagacggagc agaaagaata tgagacagag gctggagaga     1440
ggagctgaga aacgctccct tttgatacaa tacatgaagc cctctttttc atagcatggc     1500
tatcacattc aagtcacttc atcttggtca cctgcagaag acctgtgtca aatcaagcca     1560
```

-continued

```
acatatcggt ctccttcggc tttccaacag acagcactaa ttgaattcag tggattatct    1620
ataaaatagt aaaatgaaag aaattaaggg gtgataaggt ggagggagat atattgaggg    1680
tgtttgtggg ggtgacatgg gagtcaggga tagagataat caagacatac tgtaaagaac    1740
aactgtgtga taataaatta aattgtatgg aaaaccactt actatgtact ttttaaattg    1800
cgttctttga cagtttcata tgtgtatata atgcaatcaa ttatttacct tccttgttat    1860
gcctctccca cccttgtcag aaaaaaagat ggctacaaag ctctttcata ttttgattg     1920 tgtcccagtg agtttcatca gtgaaatttt tctgacctcc agtttggaac tgcccaatgg    1980
agccttgtag attcatggat ggatacataa caagagagag tgattctcct agaatctgtt    2040
agtaaccaat ggctcaatga tgaagagtat gacattatgc cctcctcccc acccaaggct    2100
gagtgttggt agtgacaatg tcacacagtc ctggcactaa caactgcagc ttttgtgagt    2160
tcatgatagc aaagatgata ttggcagccc ttctcactct tttcactctt acattctttt    2220
gacaccttct tccacaatgt ttctgagcct tagaagatga ggtataaaaa tcttgtttag    2280
ggctgagttc ttaattgtcg ctcattctta gcacccttgg tatttatgag tctttgaatc    2340
cacaaccatt cactagagag aattctctaa ttaagaatga tggataattt tgtgtatgag    2400
caccagcata agtacttaga agataacttg ttgctttgct cactcagtta agtaagagta    2460
gtaagttcct ttctagggtt tatgtcttct tcagtgatag gtttttttttt ttcttcctgg   2520 atttacagtg cttggcatgg attctctgca gtggggccag gactcaatcc agtgattgcc    2580
catattactg ttattccact atcacacggg tgggcttgta ttgcctgata agtaggtatt    2640
gccattcata gggttcacag ctgattcaga ctttgatctc ttttttgccct agtaacttgt   2700 ataatatctt ctgggactgt gaaagttatc aggcaggtgg ctggtggtgt ggctcaatgg    2760
tggaaatcca atgtgatatc atctatttac gtctcaatct gatgttaggt tcttgtgatc    2820
tggtgatgtg atttggacag aacccaaagg aaagggataa atgagttgaa gtgaagaaca    2880
gtctgctgtc agcttctgca agtttatagt gcatcgacgg tcttaccagg aatcagatgc    2940
atgaattctg tccagcattt ctaggcaatt ctgtggttgt ctagaactca aaattttgga    3000
caaaaggaag gacaagagaa ggtaggaaat gctatctgtg aacctaaaac aggaaggagc    3060
attggtctgg ggagtaatca gtcagtcatt gcatcagaaa tgaactaatt tgactaaatg    3120
aatgaatgaa tgaatgaatg aatgaatgaa tgaataaaag cacccaggaa acttcaggta    3180
aagagacctt tgtccttaat tcttactaat tgtacaatac aatcattagc ctttaacaca    3240
aactcggctc ttaggtattt ttttttatttt tattttttag aaagacaaag tgacatatgt   3300
ataaaattgt tttaaaaatg caaaggattt ctagtcattc ttgtaattag cttggtctct    3360
cagatgctgc agggttattc tcctacaact gcaaacagaa gaattaaaaa tacagaaaaa    3420
attcagaatc aattttcatt atgggcttgg actgggaaaa atgtgaaata attcttacaa    3480
gaccatgttc ccatggttga aaaactttat cagcaatatg ccaattacga catacgtgaa    3540
aagtgaataa attgtctcct actaccttac caccaaggaa atatgtttcc aagtcatgca    3600
tacaaaagag aatttcacaa tgagtaagga caggaggaag gaaaggagat taaatatgaa    3660
gaggaaaaga ctaggaattc tgtgagaact tttaccatta actttagcat actgtaatat    3720
ggaacagtaa cgaaattata gtggagagaa acaaaagttc tacaaagtc tataagatga     3780 atgaacttac attgtcagta attgacagca agttgaaacc tgagtcagaa tccaatctca    3840
ttcttgctcg catgtctcga ccctgccttg ctgatgctgt ttagtgactt aagaaattaa    3900
```

-continued

```
aagaatattt gtagtaaaat gagactcaga atcctagcct ctgtccaact attagaagcc    3960
aacaggtcag ctgtgtcctt ttctaacaga tgagaaaact gagccccaga ggagagatgt    4020
ttcgcccagc atcagagcct ttcaactcag agccagacct agaagatc                4068

<210> SEQ ID NO 50
<211> LENGTH: 3949
<212> TYPE: DNA
<213> ORGANISM: Artificial Sequence
<220> FEATURE:
<223> OTHER INFORMATION: Reverse complementary sequence of transcription
      regulatory element D

<400> SEQUENCE: 50
tttccatcgc ctcatatctt cttcaatttc tttcttcaaa cacttaaagt ttttttaatt      60
aaacaagtta gagttactag aatgtatttt atattatttg aagctattgt gattgctgct     120
gcttctttta tttcattctc aagctgtttg ccatttttac ataggagggc taatggttgt     180
tttagttact cttgtatccc gtcactttgc tgaaagtttt aatcacctgt acttccattg     240
atgaattttt agtgtcactt aggtggtacc actatatcat caacaagtaa caacacttct     300
acttcttcct ttccttgttg tcctttagct gtttaatggg tctatctaga acttcaagta     360
ctgtattgag tagatataga cttcacaaac ttgtcaagtt acagatttta taggaattcc     420
tttgtttttt ctctccattg tatttgatgt tgtctatagg tttgctgtaa atgtccttca     480
ttatgtgtgt gtatgtaaat tgtatccata atatctccaa gacttttatg atgtttgttt     540
cttgtcaatg actatttatt tatttatttta tttattggtt tttcaagaca gggtttctcc     600
gtgcagcttt gaagcctatc ctggcactcg ctctggagat caggctggcc ttgaactcac     660
agtgatccac ctgcctctgc ctcccaagta ctgggattaa aggcatgcac ccccaatacc     720
tggcttatca atgactttgt aagcatgtaa agggataata aaaaagtgtt ttttaaagtt     780 tattttatg gtggattaca gttactgatt tttgtatgtt gaaccatcac tgcgtatctg     840
agatgaagcc tactggatca gtttgtatga caaagttact ctgtggcttt tggtcctggg     900
actccctctg tagaccaggc tggcctcaaa ctcacataga tgcaactgcc tgtgtctccc     960
aagtgctggt gttaatgcca tgtgccacca ctgcccggct ctttattcct ttttataact    1020
caaatatttt gtaagtaact acagaaataa taggacacag aaaatgtagt actgcctagt    1080
aataattgtt gataacctgg attctccctc tccctaggtt ctgtgcgacc tggccctgat    1140
ccagctgcca atttctctcc tcccaccctg gtgttttctc ttgatctcca catgtcactc    1200
cacatcagca ctctcctggg cctgttgctt ccttagagat cctttcctgg cctagtggcc    1260
tctctaacac ttggattccc tccctgctct gggatccatc ttctcttctc ttttccaggt    1320
gacctgccct tgccctggga tctgtttttc acaggtgatt gttccttgct gacatctcaa    1380
agactgtcaa agtttgcatg gctgtgtggt gcatgtgtta attgactgaa ttaggattct    1440
gcatacagag accatgtaaa tcttggccaa aggcagttca gtgactatgg tttcaaaggc    1500
cccaactact gagcctcatt cttaactgtt tcctttccct ttataagcaa gtgcctccca    1560 tctgtttttct ctctttccat ttctgctccc tattggttaa cacctacccc tccctttatt    1620 ccctttttcca ataaactcca tgtggatttg ttgagtgtgt tggatcatgt tttatcaccc    1680
aaatgcacag taaaagacaa caacaacagt atctttaaaa taactgtgaa tagtgtatct    1740
attgagctag aaccataact caggttaaga gcacttcttg ttctatcata gtactacagt    1800
tctatttctc tctcccaacc ctggtggctt tcacccacca gtaactacag ctcttagaga    1860
```

```
acacaatttc tcctgatctc catgggctct tgcatatgca tgtacattta tacatataat    1920
ttaaaataac taacacgcac acactcactc acatatatat aatttttgag acagtttttc    1980
tctttgtaac cctggctatc tttctgctca gagatacttt tgcctatatc tacagggtgt    2040
tgagattaaa tacttgaacc agtgctgcct gcgtaaattc ttttttaagt ttatttgatt    2100
tcctgttgat taaaaagaaa tcccccaaaa tacatatcta aagacaagat ccagagtgca    2160
atggtcaagt gtctttggct agactggagt tcactgctac agttcctctt ggacacctag    2220
aataaaaact tggtatcagc agggactgtt agctcaagat taaactgcct gtaaatgcaa    2280
gactatggag gctaaagctg ggagatattc agagtttgag cctagtctgg gcaacttagt    2340
aagactcttt ctaaaataac caacaaaatg agaggcacag tgtcacacac ttgtcactca    2400
gcacttagga attagcggct ggataatcaa gcctgcaagg tcctcttgtg ctatgtagag    2460
agctcaagat gagtgtgcac tacatgaaat ctgtgtaaag aagaaagtag ccaacaaaaa    2520
ctacacacca aaacagaacc aatgaaaact gtattgtctt tgatatctac ccatagtcac    2580
tagagcttag gaagcaataa cctaaaagat tttaaaaaga gccaggcatt agtggtgcac    2640
gcctttaatc ccagcactcg ggaggcagag gcatttgcat ctctgtgagt tagaggccag    2700
cctgggcagc tttgaacagc atcaattgta gatgcaagat aaatgccatt aatacacagg    2760
gaaaatctct aaaatgttgg gaagaaatca attcctagcc ctaacaagta ggtaacaatc    2820
atcatccttt cattacaaat tcactttaaa attgggtagt gagttacctg tcaccatgat    2880
ccagcaatcc cagctacccc agaggcttag acagtaaaat aggctacagt atacccagga    2940
gctccagacc agccatgaca tcttcacaag aactaaaaaa aaattaaaaa ctaggggagc    3000
tgttaggata tcagtcaggc aaatagatga accactacat cctcccttta ctcacaattg    3060 cctttttgacg aatgcaatgg atgagagaat cacattgcac tgctagttcc cataaagacg    3120
gctggactcc atcttggctc aagggcagag agttcataac tgtccttagg aaatcataaa    3180
acctaaaggt caaaggtgtg gctacagtag gatattgcat catggcatgg ggtgtcttat    3240
gctaaataaa aacagacttg gtctgagatg tgctgacacc tgtccctaaa gaacaggtaa    3300
ctagaatttg aatctaaggt atggttacca aattggtgaa aaattcagca agaaaagagt    3360
gtttgctttg tatgaaggaa ctcatgttca cctttttggtt aaggtatatg agagtggtga    3420
gaaataaact tgtggtgttc agtattaact ggatctgccc tcctgatttt attctgtgtc    3480
tttctaggct tcctttagtc cacactctcc ctttcaagaa caaacctcag gctgcttggt    3540
tggctgccac tgcagctcca aaaagtcagc ttctcacatt gcacaagcat gtgaacttca    3600
taaatctgct tgatagctta gcttccaatg tttaaatcca gtgaggtcta cttgattatt    3660
tacaggctga taatccattg cattcagaat aatgaaaact agtgatggat cttcctgagg    3720
tgcaaataat cccaaagcaa atgccaaagt gcctgcaagg taggaatgaa ctttatttcc    3780
aaactgacag cagcagctgc tgtggtggaa gctggtgcac acactgtata acttgagagg    3840
cagtcagctg gatctcctgt tgctaacagt gcgactgatg agagctgaca cccatcaatg    3900
gagttagggc ctcactccga gatcaagtgt tgtggcagct acacagatc        3949
```

```
<210> SEQ ID NO 51
<211> LENGTH: 1128
<212> TYPE: DNA
<213> ORGANISM: Artificial Sequence
<220> FEATURE:
<223> OTHER INFORMATION: Reverse complementary sequence of transcription
      regulatory element E
```

```
<400> SEQUENCE: 51
atggtcagac ccaggtgctc tggcagacag gtttcagtcc ctcccatgag gtgtcccatg        60
tatgctcagt gagatgtcct tcacctctga cacctcagat acctcaccgg gttctctttg       120
cagcagaaaa tagatgctaa caaattctgt tgatgaatcc atctgggcaa taagactcaa       180
gggagccact tgcctacaca cctgaataga tgaagcaagc cctaccctac cctccaggta       240
tctaaaacca ggattccaat aataaaatcc ttacaattca caggggagcc tgaatgtttt       300
gatttacaat gtggcattga ttgtgttgga gaatatgggg ggaacaacta gtgcaccttg       360
aaacatcact gctcaattgc agcattgcca aaataccccca gcagaacgca ttaggacaga       420
gtgtctgtgg gacaggtcca tagtgcacat acatgacctc ccgactgaac tccctaggag       480
catgtgacag tgaaggacag agaggcccag tgtatgctgc tgatgataaa gcttctgcac       540
aacaaaatct gtcctttctg cccectgcac gggacaaggg ccagttgtag agagtgcttg       600
tgtcacaggg ctcctctagg cctctgtgtc ctggccacag atgggtgtgg accgcagcct       660
cagggttctc atgacatgac ttctttcgtt attacatttg tttctctgtc tctgtctctg       720
tctctgtctc tgtctctgtc tctctctctc tctctctctc tctctctctg       780
tgtttatgtg tgtttgtaga ggttaaaagg tgctctgtag catttcttca aattggttta       840
aatagtaaaa acgctgagtg agatgtcaga taattgggta aatgttgaga cataagagaa       900
ttaaaggagc caactctata gggacttctt acctgtacca aatgttcaga tggaagtgct       960
ggggaggtcc tgtctttaca aatcctctat atgaataagc ctaaatactg cctcctccag      1020
ccttatactc ctgtctccac ctgaggtgcg agccacacgc acccagctct tatatctatc      1080
agactggttg aatttcgtgt acctcagtgt ggccttgaac tcctgatc                   1128

<210> SEQ ID NO 52
<211> LENGTH: 1352
<212> TYPE: DNA
<213> ORGANISM: Artificial Sequence
<220> FEATURE:
<223> OTHER INFORMATION: Reverse complementary sequence of transcription
      regulatory element F

<400> SEQUENCE: 52
cttctgagta gtattgcatt gagacagcac tggatactgg aaatcttggg gatactgtta        60
tgaactgagt gtctctcccc taaagctaag attgaaacta aaatctccaa tgtcttgtgc       120
taatagtatt tgggtgtggg gttttagaat gtctttagaa ttacatgaaa tcatagggaa       180
gagaacactt gtgatggaat tggcggcctt aaatgatgaa aaccatagac caagcctgga       240
acacttgtcc tgtccttttg taacattctt gtcatgtgct gtcctctgat ttcttatgat       300
actgcagaaa ggcatttgac agctgctggt gtcatgcttt tggacttccc agttccaga       360 gctgtgagcc aaatgtatct cttctttata aatctcccag cttatagcat tttgtttgtg       420
gaaaacaaat agtcttagag aaataattat agattatcag tggccaagat actgatagaa       480
gcatcaaaga ttattttaaa atgccaggcc agggagatgg ttcagagggt taagaggctt       540
gctgccaagg ctaatgacct gagttctatc ccagaaacca catgcatagt ggaaggatag       600
aaatgactcc cggaaagttg tcctttgttc tctgcacatg taccatggca tacacataca       660
tatataacca gtaaggtgta gtaaaagtta gagtcaatgc gctatttttt atataaataa       720
acataaggac acagcacacg cgcgagcaca catacacaca cacacacaca cacacacaaa       780
aaaaaaaaaa aaaatgaaa gtagaagagg gcctgctgag gaagagggtc ccagctggtt       840
```

```
aggaaggagg atgacaatgg tattaaaggg tgaaaaatga cccaaattca ctatatactt      900
acatgaatct gtcaaatcat ttaaaaagcc atgtattact gtattagttt cttgtctatt      960
gttgtgataa aatgccatga actaaagcaa ctttaaaaag tttattttgg tttttcagttc    1020 cagaggttcc tgagggggca ttcataatgg tgggagaggc atgtcagctg gtagccaaag     1080
caggaagctg agggcctaga gagatggctc actagttaag agcactgact cctcttccag     1140
aggactcaag ttcagttccc agccccacat ggcagctcac acctgtctgt agctccagtt     1200
tcaggggacg caacacccat ggcaaaacat tgattaacat aaatataaaa tgaaaacctc     1260
cagtttcagg gtatccgaca cccacgacaa aaaacatcaa tgggtataaa aataaaataa     1320
aatactttta aaaagcagga agctgagaga tc                                    1352
```

<210> SEQ ID NO 53
<211> LENGTH: 1246
<212> TYPE: DNA
<213> ORGANISM: Artificial Sequence
<220> FEATURE:
<223> OTHER INFORMATION: Reverse complementary sequence of transcription
      regulatory element G

<400> SEQUENCE: 53

```
ctggtacctt cttttcccag agtctataca agttaggaaa aacaggaaat gtgggaaaac       60
aggagacagc tgaagctcag catctggcaa gacccaacag ggtccctctg ctaatgatgt      120
tccctgagat ttgattctaa aacctcagat tctttaagtc atgaggtgac atcctcacct      180
cagacttcta aatcacctgt gttctccttt ctacaaatgg gacaaacatc catccaacat      240
tcaagtccaa aacctgagag tcatccttaa tttctctttt cctttttagc tccctaccga      300
ttctttttca aaaatccacc ctttctctca atcttcacgt catcagtttt tagaaatagg      360
tcatttctct ccctgagctt atcatctgcc tacatgaatc tgaactctca ttttaaaaat      420
cacatgtaga gcttggcccc tgccttgagc ccgacttctg cctgtccact ctgggaactc      480
ctgtcctggg gactgcaggc aaatcaactt gcccctgag gaccaagcaa cctcaagtct      540
gatgacatca ctgtgctagt ccagttccca cccccaccta gagagggagt gcccagacc       600 cgcctgaacc caccataaga cccatcagag tatcagaccc tcttgcatcc accaaagaga      660
accttggacc catacacacc aggagaggaa gagacggcac ctgaacccac tggaagaaga      720
gatgggaaga caacaatata aaaacgcatt caataacaga aaaaacaata tgacaccact      780
agaatctagg gactctacgc cagcaagacc tgaacatccc aacacagatg aagcagaaga      840
gaatgacttc tgcttgtact tgaagttcta tctggggcaa tatgacaaca aaaaggagaa      900
caaggggata caaattggaa aggaagaagt caaattttta ctgtttgcag atgatatgat      960
agttacataa gtaacccaaa aaactctacc agggaactac tacagctgat aaacaccttc     1020
agctaagtgg aaggatacaa gattaactca aaaaatcact agccctatta tacacaggag     1080
ataaatgggc tgagaaataa atcagagaaa catcatcctt tacaatagcc aaacaacata     1140
aaatatcttg gggtaatgat aaccaaacaa gtgaaagacc tgtctagcaa gaactttgag     1200
tcttaaaaga aagaaattaa agaagatacc agaaaatgga aagatc                   1246
```

<210> SEQ ID NO 54
<211> LENGTH: 1886
<212> TYPE: DNA
<213> ORGANISM: Artificial Sequence
<220> FEATURE:
<223> OTHER INFORMATION: Reverse complementary sequence of transcription
      regulatory element H

<400> SEQUENCE: 54

```
gatctctgtg agttcgaggc cagcctggtc tctagagcga gtgccaggat aggttccaaa      60
gctacacaga gaaaccctgt ctcgaaaaac caaaaaaaga aaaaggaaag aaaagaattt     120
agtgaaaaag caacattgtg catatgttat gtgtgtttac atgatgagtg tattctgtgt     180
atgctacaac actcatgtaa aggtcagagg aaatctctct ctccttccaa ctcgtatcac     240
tagtcttata gggcaagtgc ctttaccctt tgagcacaac cttggtcttt ttaaggtgtg     300
tgtccctgtg tctggttcct tcgtagtttg atagtgtttc caaagcttct tcctaaagca     360
ggacaaattg gctgagcctg aatccgatat gcgtgtggag aggggcgggc aataggtgtg     420
tggaaagaga gtgtctgtgc ctctttatta gacccagaag cactacctac aagtccagcc     480
ttactcttct gtcagttcct cttgaacact aagattgctt acagtttttt ggtactataa     540
attaaataat aagtgctaca agagtcttta cattctttga tcacatctac ccagagacat     600
tgccgagttt agagacaggc aagtcttctg ctctgtcgcc tagttagctg gtaaatgtgc     660
tgccttttca atgatacatg gcagtgtgag cagccattta ttgacttttg catgatcaac     720
aatgtttcac acatggcagt tcacattcac aagtacctgt tctgtactgg cattcgggtt     780
taagagagta ggtgcctgat cctggagtct gtattctctg ccttgttcta ccactgaacg     840
ttcttcctgt tcctagccct cttactgaat cattttttct tccatacagg ccgatgaaga     900
tcccatcatg ggtttccacc agatgtttct attaaagaac atcaacgatg cttgggtttg     960
caccaatgac atgttcaggc ttgccctgca caacttcggc tgacctccac ctggccagat    1020
cctcacgctg tttcctcctc cctcctcttc ccaatactat ctcactcctc cagatgctcc    1080
aaatatcata cacaaatgag cagggccgag gtgggagtag gtgcagtgcg cttctgtcac    1140
cacggtgttg tgcatgatgt ttggatgcta gactagttgc atctgacagg agaagtttgt    1200
gttgtaccag cgcatgcctt ggaaagactt aagtaatgca aaagattgtc ggtttttgtt    1260
tttgtttcat tttgtttttt aatctactga caagttgctc tagtaaccca aagaagtgaa    1320
ggagaaagca gctgcctcac cgcccagata ttgatttgtt cagatgtttc aatgcctcat    1380
gatacaataa aaccacaaaa attttcttaa cagtttaaat tgttttaatt agttaaatag    1440
ctctttgggc atcaacagtt ctgaccaatt gtctctcatt tcaccctccc atctctgcct    1500
catgttaaca atacctgctg caaggagcaa attgactgaa gttaacagtc ccaaccaagt    1560
ttctttcaag cctgctaggc cagagttctc tccaacccac ttggtctttg gaaagcctgg    1620
agagctggaa gcaggtctgg cctgaagctt atcttgtact gaagactcta aagtgagttc    1680
tgtctgacac ctcctgtagc ctctgctctg agtctagtag caggatagat gattctgtag    1740
ctgctagaaa gaccttgata aatatggttt cccatgttta gattctatgg gttgaagtcc    1800
cggatggacc tgctctattc ccaaaagggt caggatcaca ttcagagtgc ccacattccc    1860
gagcaaagca agagatgttg tactgc                                          1886
```

```
<210> SEQ ID NO 55
<211> LENGTH: 1118
<212> TYPE: DNA
<213> ORGANISM: Artificial Sequence
<220> FEATURE:
<223> OTHER INFORMATION: Reverse complementary sequence of transcription
      regulatory element I

<400> SEQUENCE: 55
```

```
gatctccaca ctcatgttga cattaaagcc atcgacaatc tcagtaagta ctagtaaaca      60
```

-continued

```
agtaacaaat aagactgatc catcacacaa cattaccctg gctgtgtctt tggagtaaaa      120
atcatgtaga tcaaggtatg gtatgcttga acaccaaaaa gtaaccacag agtagaagag      180
tagagtccag tgagtgcctt atgcgtgagc ccacttccct ttttgcgttt gtttttactt      240
aatgtctggc agaattcagg catgtaggtc agaggccacc ttgcaggagt ccgttctctc      300
tttccaccaa ctggatccca gggacaggac acaggtcttg ggcttggcag cgggtgccct      360
tacctactga gccatttcac cactgacttg gtttttactga aagctaactc tgaagactgg      420
aattcgatac tttttttaggg tgatgagtca ctcactgtac agcctcagca ctattgctga      480
agtacattac cctcacaaac caggcagccg gagactcact gcttacatgt aatcgaggcc      540
atgctatgtt aggtaacatg ttggagactt accaaaaact gtgtttaa gttacttgca      600 accttctgta accacgcaaa ctgctgtgtg attctttaac ctatgtctcc acaatcacaa      660
cagacatctg ttccgggtaa ttgcacattt ctaattaaag cttttcaaagt gggccaggtt      720 ctcttggagc tgaaatgttc gttgaagggg gcaaagttat tttctctaac atcatgaggg      780
aactgggtca gggtgtgggg actgcaccct gctgaggggga tggtatagga atgacccacc      840
tttggcctgt gttccttttg ttttgctttg tgcatgtgtt tgcatttctg tttgcatgca      900
agtgagctca tttgctgtgg aagcccaaag ctgatgtcac tctctatctt attcactgaa      960
ccagagtcgc tccacgaacc cagagctctc agctaacact agcctagcta gccagctgcc     1020
cttgggatcc tttctcagcc ttccaagtgc tgaaattgca ggtacactac taagcccgta     1080
ggcctttgtg tgggttctgc agatccaaac ttcagatc                            1118
```

```
<210> SEQ ID NO 56
<211> LENGTH: 1611
<212> TYPE: DNA
<213> ORGANISM: Artificial Sequence
<220> FEATURE:
<223> OTHER INFORMATION: Reverse complementary sequence of transcription
      regulatory element J

<400> SEQUENCE: 56
```

```
gatcacttct aagcaatttc tagataagaa tggacattca acaccattag acatgtgcgg       60
cttttggaca gtcaacccag ttagttattc ttaaaagtgt taaatattag gcctgcttct      120
tccctatgac ctctattttg acctttattt tcctgttctg ggttttgctt ctccaggtac      180
taggagagag gttggtatcg ggtaggtgca ctcatgagaa agaggccctg aggagtatga      240
gagctacaca gccagaggcc tctttctttt ggacctgccc aactgaacaa caacaacaaa      300
aacccaaaca aacaaacaaa aacaaagcaa ctttactaaa aattccaagg gaaatgaaga      360
aactatagat ggaatgaaaa caggcaaggg catacctatt cttataggca gctagtgtta      420
ggccactggt agcccactag atgttgcagt ctgagcctga tacacagggc cacatacaac      480
tatgctcctc tggtcctgcc acccacctag ccattgtact ggctaacagt ctggggggt      540 gggaataaga gtggtggatt acctaatagg atgttcacag taagtgctca atgcacacag      600
taagttctca gcaggggaa agtcaggcta gttggtggac actcatctgg ttccacctta      660
gagtgataag atgtggtcta ggctatagac aggtgcttcc cttcctggcc atatcaggcc      720
tgaggcaaca aggaaagcaa aggctgccta ggaaatctct taggggtcca tttcccagcc      780
tggctcctcc aactggttct tcttgggttc aggtacagat tggtcaaagg gtttggcttc      840
ttcttgtagc cctcactggc agggctctat gtgggcttca acttctgtcc ccaaagttca      900
ctgtctgacc ttgcatggag tccaggcagg gcatgggtct caactaccat gtgaccccag      960
```

```
ccatgacatc tgggtctgat gttccccaaa gattgcatga aggcctctaa actctcagtc      1020
ttgttctcaa agctttttatg ctagacagta gtcttggagc tgtaggggac ttacctagac     1080
atatccctga gaaacccagg ctgcaggcag aggaacattg tggcagctta gtcagaggga     1140
tgggaggaca tgccattgtc atcactaagg agatgtagac cagttgacca gcccagtaag     1200
gcctgggttt tccaaacttc aggagctttg cctgaatttc aggtatgaaa gtttgccaca     1260
ctgaaaggcc atacaggtgg aaaagtccat ccaaaactct gccttggtgg gaggatatca     1320
atgaactatt ggatgcttgc tggagcatga aatatcctga atggccattg tccagggta      1380 agacaggtct caattctccc agagccccca cagtacttaa ggaaacctgg cttagctgac     1440
tgtcccctgc cttggcactt gtgatatgta agttcctacc atctcatctt tgactcggga     1500
tgagggctgt ggataggga caaccttgct gaagaagacc agaaaaagac cttctccttc      1560
ctctctccag ctgctcatag aagcagcgac cttctgagtc cacaaaagat c              1611
```

<210> SEQ ID NO 57
<211> LENGTH: 1299
<212> TYPE: DNA
<213> ORGANISM: Artificial Sequence
<220> FEATURE:
<223> OTHER INFORMATION: Reverse complementary sequence of transcription
      regulatory element K

<400> SEQUENCE: 57

```
gatccagcta ttagaatggt gcttgcattt aaagggtaac cagggaatat taggctccta       60
aaatcaagta gtccaaaaca tgtcatgcaa cctgacactt tggttattta tgaattaaag      120
atatttgaga aatggacaat ataggaccat tctaattttt gggagatgtg acagaatcca      180
tcctttcatt aggaaaacaa tgattctact aatggtagag accaagaaag gcatgaacat      240
cctaaaagtt gttcatcctt taagccttca tgcaaaatgt agttgctttt ctcacaactt      300 gtcactttt aaagtctaca tcaatatcta aataattgct tttcattcat cagttcttta      360
agtatttgtt tatcttgtct ttgggtggca ctgacaaaat tgcactaaat aaatattgta      420 cttttttccat gttaatgtga tttatgctac tttaatctct gacaaaacca aaatgaaacc      480
ctattaaagg ggagttggtc aaatctaccc tttttcatca agaatgggta cagaactaca      540
atggtgaaag atgaatcctg taaatctaca ttagtgacta cagccagtat atttcaaata      600
attcctacag taacaaaatt aatttgcaat ttatgtatcc tattttaaat ttgcatataa      660
aagcaatata taattgccaa tattgagaat attttgtcac ttaagattgt gaagaaccaa      720
tttaaaataa aaagattagc agaaaaaata aatttataaa ataaatctat gaaaataaca      780
agtctaaatg attcaatgta atagagtggc actatgacac ttctatatgt aaaagatatt      840
aatatttact aatatcaatc tattttttcaa tatgtttgaa ttcttcattt tttttttaaa     900
tttccaagct aactttaatt ctcccaaaac atgtcaatag taaatgcttt taagacatag      960
caattcagtt actgacaatt tctgaattta ttgtattttc caaacatgg gtaaagattt      1020 agaaatgtgt gttgcaatga cagctttaca ttccaaattt ctgagcttta ggttcaatgg     1080
catcaaaagt tcttttttact ctaggaatgc tgcaactaaa acagcattgc atggctaaac     1140
aggccaattt actttctaca agcagggtaa gtgcacgcca gtgtcacaga ctttcataga     1200
aagcattttg ctggcccact gaagacttct tacatgccag ggggaaaata tcacacgtag     1260
ccctccaggc tggggacaca tgccgcttat gtgcaaggg                            1299
```

```
<210> SEQ ID NO 58
<211> LENGTH: 1108
<212> TYPE: DNA
<213> ORGANISM: Artificial Sequence
<220> FEATURE:
<223> OTHER INFORMATION: Reverse complementary sequence of transcription
      regulatory element L

<400> SEQUENCE: 58
ccacactcat gttgacatta aagccatcga caatctcagt aagtactagt aaacaagtaa      60
caaataagac tgatccatca cacaacatta ccctggctgt gtctttggag taaaaatcat     120
gtagatcaag gtatggtatg cttgaacacc aaaaagtaac cacagagtag aagagtagag     180
tccagtgagt gccttatgcg tgagcccact tcccttttttg cgtttgtttt tacttaatgt     240
ctggcagaat tcaggcatgt aggtcagagg ccaccttgca ggagtccgtt ctctcttttcc     300 accaactgga tcccagggac aggacacagg tcttgggctt ggcagcgggt gcccttacct     360
actgagccat ttcaccactg acttggtttt actgaaagct aactctgaag actggaattc     420 gatactttt tagggtgatg agtcactcac tgtacagcct cagcactatt gctgaagtac     480
attaccctca caaccaggc agccggagac tcactgctta catgtaatcg aggccatgct     540
atgttaggta acatgttgga gacttaccaa aaactgtgtt ttaaagttac ttgcaacctt     600
ctgtaaccac gcaaactgct gtgtgattct ttaacctatg tctccacaat cacaacagac     660
atctgttccg ggtaattgca catttctaat taaagctttc aaagtgggcc aggttctctt     720
ggagctgaaa tgttcgttga aggggcaaa gttattttct ctaacatcat gagggaactg     780
ggtcagggtg tggggactgc accctgctga ggggatggta taggaatgac ccacctttgg     840
cctgtgttcc ttttgtttttg ctttgtgcat gtgtttgcat ttctgtttgc atgcaagtga     900
gctcatttgc tgtggaagcc caaagctgat gtcactctct atcttattca ctgaaccaga     960
gtcgctccac gaacccagag ctctcagcta acactagcct agctagccag ctgcccttgg    1020
gatcctttct cagccttcca agtgctgaaa ttgcaggtac actactaagc ccgtaggcct    1080
ttgtgtgggt tctgcagatc caaacttc                                       1108

<210> SEQ ID NO 59
<211> LENGTH: 680
<212> TYPE: DNA
<213> ORGANISM: Artificial Sequence
<220> FEATURE:
<223> OTHER INFORMATION: Human CMV promoter

<400> SEQUENCE: 59
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccaccccat tgacgtcaat gggagtttgt     480
tttggcacca aaatcaacgg gactttccaa aatgtcgtaa caactccgcc ccattgacgc     540
aaatgggcgg taggcgtgta cggtgggagg tctatataag cagagctcgt ttagtgaacc     600
gtcagatcgc ctggagacgc catccacgct gttttgacct ccatagaaga caccgggacc     660
```

```
gatccagcct ccggactcta                                              680

<210> SEQ ID NO 60
<211> LENGTH: 35
<212> TYPE: DNA
<213> ORGANISM: Artificial Sequence
<220> FEATURE:
<223> OTHER INFORMATION: 3prime ITR sequence of a transposon vector

<400> SEQUENCE: 60
catgcgtcaa ttttacgcag actatctttc taggg                             35

<210> SEQ ID NO 61
<211> LENGTH: 13
<212> TYPE: DNA
<213> ORGANISM: Artificial Sequence
<220> FEATURE:
<223> OTHER INFORMATION: The sequence of the left terminal repeat of the
      wildtype piggyBac 5prime ITR

<400> SEQUENCE: 61
ccctagaaag ata                                                     13

<210> SEQ ID NO 62
<211> LENGTH: 31
<212> TYPE: DNA
<213> ORGANISM: Artificial Sequence
<220> FEATURE:
<223> OTHER INFORMATION: The sequence of the 31bp spacer of the wildtype
      piggyBac 5prime ITR

<400> SEQUENCE: 62
atcatattgt gacgtacgtt aaagataatc a                                 31

<210> SEQ ID NO 63
<211> LENGTH: 19
<212> TYPE: DNA
<213> ORGANISM: Artificial Sequence
<220> FEATURE:
<223> OTHER INFORMATION: The sequence of the left internal repeat of the
      wildtype piggyBac 5prime ITR

<400> SEQUENCE: 63
tgcgtaaaat tgacgcatg                                               19

<210> SEQ ID NO 64
<211> LENGTH: 13
<212> TYPE: DNA
<213> ORGANISM: Artificial Sequence
<220> FEATURE:
<223> OTHER INFORMATION: The sequence of the right terminal repeat of
      the wildtype piggyBac 3prime ITR

<400> SEQUENCE: 64
tatctttcta ggg                                                     13

<210> SEQ ID NO 65
<211> LENGTH: 19
<212> TYPE: DNA
<213> ORGANISM: Artificial Sequence
<220> FEATURE:
<223> OTHER INFORMATION: The sequence of the right internal repeat of
      the wildtype piggyBac 3prime ITR

<400> SEQUENCE: 65
catgcgtcaa ttttacgca                                               19
```

```
<210> SEQ ID NO 66
<211> LENGTH: 171
<212> TYPE: DNA
<213> ORGANISM: Artificial Sequence
<220> FEATURE:
<223> OTHER INFORMATION: The 5prime internal domain sequence of the PB
      transposon recognition site

<400> SEQUENCE: 66
tgttttatcg gtctgtatat cgaggtttat ttattaattt gaatagatat taagttttat      60
tatatttaca cttacatact aataataaat tcaacaaaca atttatttat gtttatttat     120
ttattaaaaa aaaacaaaaa ctcaaaattt cttctataaa gtaacaaaac t             171

<210> SEQ ID NO 67
<211> LENGTH: 272
<212> TYPE: DNA
<213> ORGANISM: Artificial Sequence
<220> FEATURE:
<223> OTHER INFORMATION: The 3prime internal domain sequence of the PB
      transposon recognition site

<400> SEQUENCE: 67
tatctataac aagaaaatat atatataata agttatcacg taagtagaac atgaaataac      60
aatataatta tcgtatgagt taaatcttaa aagtcacgta aaagataatc atgcgtcatt     120
ttgactcacg cggtcgttat agttcaaaat cagtgacact taccgcattg acaagcacgc     180
ctcacgggag ctccaagcgg cgactgagat gtcctaaatg cacagcgacg gattcgcgct     240
atttagaaag agagagcaat atttcaagaa tg                                   272

<210> SEQ ID NO 68
<211> LENGTH: 63
<212> TYPE: DNA
<213> ORGANISM: Artificial Sequence
<220> FEATURE:
<223> OTHER INFORMATION: 5prime inverted terminal repeat sequence

<400> SEQUENCE: 68
ccctagaaag ataatcatat tgtgacgtac gttaaagata atcatgcgta aaattgacgc      60
atg                                                                   63

<210> SEQ ID NO 69
<211> LENGTH: 27
<212> TYPE: DNA
<213> ORGANISM: Artificial Sequence
<220> FEATURE:
<223> OTHER INFORMATION: The sequence of the forward primer of the PCR
      reaction

<400> SEQUENCE: 69
gcaaaaaagg gaataagggc gacacgg                                          27

<210> SEQ ID NO 70
<211> LENGTH: 28
<212> TYPE: DNA
<213> ORGANISM: Artificial Sequence
<220> FEATURE:
<223> OTHER INFORMATION: The sequence of the reverse primer of the PCR
      reaction

<400> SEQUENCE: 70
catagcccat atatggagtt ccgcgtta                                        28
```

```
<210> SEQ ID NO 71
<211> LENGTH: 447
<212> TYPE: PRT
<213> ORGANISM: Artificial Sequence
<220> FEATURE:
<223> OTHER INFORMATION: Amino acid sequence of the A chain of PD L1

<400> SEQUENCE: 71

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Thr Pro Arg Asp
        210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
            275                 280                 285

Thr Gln Pro Arg Glu Glu Gln Phe Asn Ser Thr Phe Arg Ser Val Ser
        290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
            355                 360                 365
```

-continued

```
Ile Thr Asp Phe Phe Pro Glu Asp Ile Thr Val Glu Trp Gln Trp Asn
    370             375             380

Gly Gln Pro Ala Glu Asn Tyr Lys Asn Thr Gln Pro Ile Met Asp Thr
385             390             395             400

Asp Gly Ser Tyr Phe Val Tyr Ser Lys Leu Asn Val Gln Lys Ser Asn
            405             410             415

Trp Glu Ala Gly Asn Thr Phe Thr Cys Ser Val Leu His Glu Gly Leu
            420             425             430

His Asn His His Thr Glu Lys Ser Leu Ser His Ser Pro Gly Lys
            435             440             445

<210> SEQ ID NO 72
<211> LENGTH: 451
<212> TYPE: PRT
<213> ORGANISM: Artificial Sequence
<220> FEATURE:
<223> OTHER INFORMATION: Amino acid sequence of the heavy chain of
      Adalimumab

<400> SEQUENCE: 72

Glu Val Gln Leu Val Glu Ser Gly Gly Gly Leu Val Gln Pro Gly Arg
1               5               10              15

Ser Leu Arg Leu Ser Cys Ala Ala Ser Gly Phe Thr Phe Asp Asp Tyr
            20              25              30

Ala Met His Trp Val Arg Gln Ala Pro Gly Lys Gly Leu Glu Trp Val
            35              40              45

Ser Ala Ile Thr Trp Asn Ser Gly His Ile Asp Tyr Ala Asp Ser Val
    50              55              60

Glu Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Tyr Cys
            85              90              95

Ala Lys Val Ser Tyr Leu Ser Thr Ala Ser Ser Leu Asp Tyr Trp Gly
            100             105             110

Gln Gly Thr Leu Val Thr Val Ser Ser Ala Ser Thr Lys Gly Pro Ser
            115             120             125

Val Phe Pro Leu Ala Pro Ser Ser Lys Ser Thr Ser Gly Gly Thr Ala
            130             135             140

Ala Leu Gly Cys Leu Val Lys Asp Tyr Phe Pro Glu Pro Val Thr Val
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
            180             185             190

Pro Ser Ser Ser Leu Gly Thr Gln Thr Tyr Ile Cys Asn Val Asn His
            195             200             205

Lys Pro Ser Asn Thr Lys Val Asp Lys Lys Val Glu Pro Lys Ser Cys
    210             215             220

Asp Lys Thr His Thr Cys Pro Pro Cys Pro Ala Pro Glu Leu Leu Gly
225             230             235             240

Gly Pro Ser Val Phe Leu Phe Pro Pro Lys Pro Lys Asp Thr Leu Met
            245             250             255

Ile Ser Arg Thr Pro Glu Val Thr Cys Val Val Val Asp Val Ser His
            260             265             270

Glu Asp Pro Glu Val Lys Phe Asn Trp Tyr Val Asp Gly Val Glu Val
            275             280             285
```

```
His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
    435                 440                 445

Pro Gly Lys
    450

<210> SEQ ID NO 73
<211> LENGTH: 214
<212> TYPE: PRT
<213> ORGANISM: Artificial Sequence
<220> FEATURE:
<223> OTHER INFORMATION: Amino acid sequence of the light chain of
      Adalimumab

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

-continued

```
            180              185              190

Ala Cys Glu Val Thr His Gln Gly Leu Ser Ser Pro Val Thr Lys Ser
        195              200              205

Phe Asn Arg Gly Glu Cys
    210
```